(12) United States Patent
Halazy et al.

(10) Patent No.: US 7,018,988 B2
(45) Date of Patent: Mar. 28, 2006

(54) PHARMACEUTICALLY ACTIVE PYRROLIDINE DERIVATIVES AS BAX INHIBITORS

(75) Inventors: Serge Halazy, Vétraz-Monthoux (FR); Anna Quattropani, Carouge (CH); Agnes Bombrun, Monnetier-Mornex (FR); Mattias Schwarz, Thônex (CH); Russel Thomas, Boars Hill (GB); Anthony Baxter, Abington (GB)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 10/240,000

(22) PCT Filed: Mar. 20, 2001

(86) PCT No.: PCT/EP01/03170

§ 371 (c)(1),
(2), (4) Date: Apr. 28, 2003

(87) PCT Pub. No.: WO01/74769

PCT Pub. Date: Oct. 11, 2001

(65) Prior Publication Data

US 2003/0171309 A1    Sep. 11, 2003

(30) Foreign Application Priority Data

Mar. 27, 2000    (EP)    .................................. 00106033

(51) Int. Cl.
A01N 57/00    (2006.01)
A61K 31/675    (2006.01)

(52) U.S. Cl. .......................................... 514/79; 514/80
(58) Field of Classification Search ................ 548/538, 548/306.1, 126, 517, 527, 138, 139, 141, 548/529, 528; 546/162, 281, 208; 514/42
See application file for complete search history.

(56) References Cited

U.S. PATENT DOCUMENTS

| | | | |
|---|---|---|---|
| 3,555,007 A | 1/1971 | Magerlein | |
| 3,674,647 A | 7/1972 | Visser | |
| 4,278,681 A * | 7/1981 | Haskell et al. ............... | 514/196 |
| 4,734,508 A * | 3/1988 | Thottathil .................... | 548/532 |
| 4,851,514 A * | 7/1989 | Thottathil .................... | 534/15 |
| 5,514,683 A * | 5/1996 | Kalindjian et al. ......... | 514/277 |

FOREIGN PATENT DOCUMENTS

| | | |
|---|---|---|
| DE | 1 932 823 | 1/1970 |
| GB | 1118306 | 6/1968 |
| WO | WO 95/04718 | 2/1995 |
| WO | WO 95/52868 | 10/1999 |
| WO | WO 00/08015 | 2/2000 |

OTHER PUBLICATIONS

Pedersen et al. "Studies on Organophosphorus Compounds XX. Syntheses of Thioketones" *Bull. Soc. Chim. Belg.* vol. 87, No. 3, 1978.
Sufrin et al. "Synthetic Approaches to Peptide Analogs Containing 4, 4-Difluoro-L-Proline and 4-Keto-L-Proline" *Int. J. Pept. Protein Res.* (1982), 20(5), 438-42.
Komai et al. "Structure-activity Relationships of HIV-1 PR Inhibitors Containing AHPBA-II. Modification of Pyrrolidine Ring at P1[1] Proline" *Bioorg. Med Chem.* (1996), 4(8), 1365-1377.
Bray et al. "Rapid Optimization of Organic Reactions on Solid Phase using the Multipin Approach: Synthesis of 4-Aminoproline Analogues by Reductive Amination" *Tetrahedron Letters* (1995), 36(28), 5081-5084.
Nicolaides et al. "Modified Di- and Tripeptides of the C-Terminal Portion of Oxytocini and Vasopressin as Possible Cognition Activation Agents" *Journal of Medicinal Chemistry, American Chemical Society* (1986) 29(6) 959-971.
Jacobson "Apoptosis: Bcl-2-Related Proteins get Connected" *Current Biology* (1977) R277-R281.
Kroemer "The Proto-Oncogene Bcl-2 and its Role in Regulating Apoptosis" *Nature Medicine* 6(1997), 3(6), 614-620.
Reed "Double Identity for Proteins of the Bcl-2 Family" *Nature* 6(1997) 387: 773-776.
Kelekar et al. "Bcl-2-Family Proteins: The Role of the BH3 Domain in Apoptosis" *Trends in Cell Biology* 8(1998) 8: 324-330.

(Continued)

*Primary Examiner*—Johann Richter
*Assistant Examiner*—Chukwuma Nwaonivha
(74) *Attorney, Agent, or Firm*—Browdy and Neimark, PLLC

(57) ABSTRACT

The present invention is related to new substituted pyrrolidine derivatives of formula (I). Said compounds are preferably for use as pharmaceutically active compounds. Specifically, pyrrolidine derivatives of formula (I) are useful in the treatment and/or prevention of neurodegenerative disorders, diseases associated with polygultamine tracts, epilepsy, ischemia, infertility, cardiovascular disorders renal hypoxia, hepatitis and AIDS. Said pyrrolidine derivatives display a modulatory and most notably a down-regulating-up to an inhibitory-activity with respect to the cellular death agonist Bax and/or the activation pathways leading to Bax and allows therefore to block the release of cytochrome (c). The present invention is furthermore related to novel pharmaceutically activity substituted pyrrolidine derivatives as well as to methods of their preparation, wherein X is selected from the group consisting of O, S, CR<6>R<7>, NOR<6>, NNR<6>R<7>; A is selected from the group consisting of —(C=O)—, —(C=O)—O—, —C(=NH)—, —(C=O)—NH—, —(C=S)—NH, —SO2—, —SO2NH—; —CH2—; B is either a group —(C=O)—NR<8>R<9> or represents a heterocyclic residue having the formula (II) wherein Q is NR<10>, O or S; n is an integer selected of 0, 1 or 2; Y, Z and E form together with the 2 carbons to which they are attached a 5–6 membered aryl or heteroaryl ring.

29 Claims, No Drawings

OTHER PUBLICATIONS

Martinou et al. "Viral Proteins E1B19K and p35 Protect Sympathetic Neurons from Cell Death Induced by NGF Deprivation" *The Journal of Cell Biology* 1(1995) 128(1 & 2) 201-208.

Deckwerth et al. "BAX is Required for Neuronal Death after Trophic Factor Deprivation and During Development" *Neuron* 9(1996) 17: 401-411.

Antonsson et al. "Bax Oligomerization is Required for Channel-Forming Activity in Liposomes and to trigger Cytochrome c Release from Mitochondria" *Biochemical Journal* (2000) 345: 271-278.

Desagher et al. "Bid-inducec Conformational Change of BAX is Responsible for Mitochondrial Cytochrome c Release during Apoptosis" *The Journal of Cell Biology* 3(1999) 144(5): 891-901.

Narukawa et al. "General and Efficient Synthesis of 2-Alkylcarbapenems: Synthesis of Dethiacarba Analogs of Clinically Useful Carbapenems via Palladium-Catalyzed Cross-Coupling Reaction" *Tetrahedron* 1(1997) 53(2): 539-556.

Adlington et al. "A radical Route to 2(S)-4-Exomethylene Proline" *Tetrahedron* (1992) 48(31): 6529-6536.

Holmes et al. "The Design and Synthesis of Novel Hydroxyproline Inhibitors of HIV-1 Proteinase" *Bioorganic & Medicinal Chemistry Letters* (1993) 3(8): 1485-1491.

* cited by examiner

PHARMACEUTICALLY ACTIVE PYRROLIDINE DERIVATIVES AS BAX INHIBITORS

FIELD OF THE INVENTION

The present invention is related to new substituted pyrrolidine derivatives of formula I. Said compounds are preferably for use as pharmaceutically active compounds. Specifically, pyrrolidine derivatives of formula I are useful in the treatment and/or prevention of neurodegenerative disorders, diseases associated with polyglutamine tracts, epilepsy, ischemia, infertility, cardiovascular disorders, renal hypoxia, hepatitis and AIDS. Said pyrrolidine derivatives display a modulatory and most notably a down-regulating—up to an inhibitory—activity with respect to the cellular death agonist Bax and/or the activation pathways leading to Bax and allows therefore to block the release of cytochrome c. The present invention is furthermore related to novel pharmaceutically active substituted pyrrolidine derivatives as well as to methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself in a controlled manner or by a self-regulated process. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide. The chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those that have formed multiple synapses. This may reflect a process, which balances the relative number of pre- to postsynaptic neurons in the developing nervous system. Although neuronal cell death was assumed to be apoptotic, it was only recently that neurons in developing rodent brain were conclusively shown to undergo apoptosis as classified by morphology and DNA fragmentation.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are protein members belonging to the Bcl-2 family (see Jacobson, M. D. 1997. *Current Biology* 7:R 277–R281; Kroemer, G. C. 1997. *Nature Medicine:* 614–620; Reed, J. C. 1997. *Nature* 387:773–776).

The entire Bcl-2 family comprises both anti-apoptotic (Bcl-2, Bcl-$x_L$, Bcl-w, Mcl-1, A1, NR-13, BHRF1, LMW5-HL, ORP16, KS-Bcl-2, E1B-19K, CED-9) and pro-apoptotic (Bax, Bak, Bok, Bik, Blk, Hrk, BNIP3, Bim$_L$, Bad, Bid, EGL-1) molecules (see Kelekar, A., and C. B. Thomp-son 1998. *Trends in Cell Biology* 8:324–330). The specific member thereof, i.e. the first found, Bcl-2 is a 26 kDa protein that localizes to the mitochondrial, endoplasmatic reticulum and perinuclear membranes. The Bcl-2 family proteins can form homo- and hetero-dimers that involve amino acid sequences known as Bcl-2 homology (BH) domains. So far, four of said domains (BH1 to 4) have been identified, the BH3 having been attributed a particularly prominent role in view of the death-promoting cascade. Said BH3 domain of the pro-apoptotic members appears to be required for the interaction between anti and pro-apoptotic molecules. The principal site of action of some of the Bcl-2 family members seems to be the mitochondria. Mitochondria have been shown to play a major role in many types of apoptosis. In particular, this organelle has been shown to release Apoptosis Inducing Factor and cytochrome c, a hemoprotein which is bound to the outer surface of the inner mitochondrial membrane. Said cytochrome c has been shown to trigger caspase 9 activation through Apaf-1/caspase 9 complex formation. Bcl-2 family members play a key role in regulating cytochrome c release. While Bcl-2 and Bcl-$x_L$ have been shown to suppress cytochrome c release, Bax has been found to stimulate this event both in vitro using isolated mitochondria as well as in intact cells following heterologous expression (Martinou et al.; *The Journal of Cell Biology*, 128, 1995, 201–208). The mechanisms by which these proteins perform their function are currently unknown. The three-dimensional structure of Bcl-xL and Bid revealed structural similarities between these proteins and the channel-forming domains of the bacterial toxins colicins and diphtheria toxins. Consistent with such structural similarity, some members of this family including Bax were also found able to form ion channels in synthetic lipid membranes.

Studies performed with Bax-deficient mice led to the conclusion that Bax plays a promi-nent role within the apoptosis pathways, notably in neuronal apoptosis. Bax is viewed to be essential for apoptosis induced by NGF deprivation in neonatal sympathetic neurons or for apoptosis induced in cerebellar granule cells by potassium deprivation from the culture medium. Moreover, it was found that in the Bax-deficient mice (knock-out) neonatal moto-neurons from the facial nucleus can survive following axotomy (see Deckwerth, T. L., Elliott J. L., Knudson C. M. et al. 1996. *Neuron* 17,401–41). Hence, the inhibition of the Bax activity leading to the prevention of cytochrome c release from mitochondria during apoptosis, is viewed to be useful to protect neurons and also other cell types from various cell death stimuli.

In WO 97/01635 (Neurex Corp.) the inhibition of apoptosis in an effort to promote cell survival is suggested to be achieved by introducing into the cell a chimeric gene containing a polynucleotide encoding a Bax-ω-polypeptide (a splice variant of the Bax gene, which displays—in contrast to Bax—an anti-apoptotic activity) being operably linked to a promoter effective to cause transcription of the polynucleotide in the cell. It is reported that the expression of the Bax-ω-polypeptide is effective to inhibit apoptosis in the cell. Perez et al. in *Nat. Genet.* 1999, 21(2), 200–203 have indicated that apoptosis plays a fundamental role in follicular atresia and they suggest to selectively disrupt the Bax function in order to extend the ovarian lifespan.

Bax down-regulation up to inhibition could indeed represent an interesting therapy for all diseases associated with apoptosis, including neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

Hence, it is an objective of the present invention to provide compounds enabling the treatment of apoptosis-related disorders, including notably the above mentioned diseases.

It is specifically an objective of the present invention to provide a treatment of apoptosis related disorders by specifically regulating the Bax function, e.g. by modulating, in particular by down-regulating up to inhibiting, the Bax function or by down-regulating, up to inhibiting, the Bax activation.

It is notably an objective of the present invention to provide small molecule pharmaceuticals, more specifically non-protein or non-peptide molecules that avoid essentially all of the drawbacks arising from the use of large peptides or proteins (e.g. restricted bio-availability as well as problems arising from in vivo intolerance thereto), however, which are suitable for the treatment of a number of diseases associated with abnormal apoptosis. It is particularly an objective of the present invention to provide small molecule chemical compounds being suitable Bax modulators (e.g. compounds inhibiting the Bax function or inhibiting the Bax activation) so to be available for a convenient method of treating diseases involving abnormal apoptosis. Moreover, it is an objective of the present invention to provide methods for preparing said small molecule chemical compounds. It is furthermore an objective of the present invention to provide a new category of pharmaceutical formulations for the treatment of a host of diseases. It is finally an objective of the present invention to provide a method of treating diseases that are caused by abnormal apoptosis.

DESCRIPTION OF THE INVENTION

The aforementioned objectives have been met according to the independent claims which are set out hereinafter in the description. Preferred embodiments are set out within the dependent claims.

The following paragraphs provide definitions of the various chemical moieties that make up the compounds according to the invention and are intended to apply uniformly throughout the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotiazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnnolinyl, napthyridinyl, pyrido[3,4 -b]pyridyl, pyrido[3,2-b]pyridyl, pyrido [4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1–2 sites of alkynyl unsaturation, preferred alkynyl groups include ethynyl (—C≡CH), propargyl (—$CH_2$C≡CH), and the like.

"Acyl" refers to the group (O)R where R includes "$C_1$–$C_6$-alkyl", "aryl", "heteroaryl", "$C_1$–$C_6$-alkyl aryl" or "$C_1$–$C_6$-alkyl heteroaryl".

"Acyloxy" refers to the group —OC(O)R where R includes "$C_1$–$C_6$-alkyl", "aryl", "heteroaryl", "$C_1$–$C_6$-alkyl aryl" or "$C_1$–$C_6$-alkyl heteroaryl".

"Alkoxy" refers to the group —O—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred alkoxy groups include by way of example, methoxy, ethoxy, phenoxy and the like.

"Alkoxycarbonyl" refers to the group C(O)OR where R includes "$C_1$–$C_6$-alkyl" or "aryl" or "heteroaryl" or "$C_1$–$C_6$-alkyl aryl" or "$C_1$–$C_6$-alkyl heteroaryl".

"Aminocarbonyl" refers to the group C(O)NRR' where each R, R' includes independently hydrogen or $C_1$–$C_6$-alkyl or aryl or heteroaryl or "$C_1$–$C_6$-alkyl aryl" or "$C_1$–$C_6$-alkyl heteroaryl".

"Acylamino" refers to the group —NR(CO)R' where each R, R' is independently hydrogen or "$C_1$–$C_6$-alkyl" or "aryl" or "heteroaryl" or "$C_1$–$C_6$-alkyl aryl" or "$C_1$–$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$–$C_6$-alkyl", "$C_1$–$C_6$-alkyl" substituted with halogens e.g. an —$SO_2$—$CF_3$ group, "$C_1$–$C_6$-alkyl aryl" or "$C_1$–$C_6$-alkyl heteroaryl".

"Sulfoxy" refers to a group "—S(O)—R" wherein R is selected from H, "$C_1$–$C_6$-alkyl", "$C_1$–$C_6$-alkyl" substituted with halogens e.g. an —SO—$CF_3$ group, "aryl", "heteroaryl", "$C_1$–$C_6$-alkyl aryl" or "$C_1$–$C_6$-alkyl heteroaryl".

"Thioalkoxy" refers to groups —S—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$–$C_6$-alkyl", "$C_1$–$C_6$-alkyl aryl", "$C_1$–$C_6$-alkyl heteroaryl", "$C_2$–$C_6$-alkenyl", "$C_2$–$C_6$-alkynyl", primary, secondary or tertiary amino groups or quater-nary ammonium moieties, "acyl", "acyloxy", "acylamino", "aminocarbonyl", "alkoxycar-bonyl", "aryl", "heteroaryl", carboxyl, cyano, halogen, hydroxy, mercapto, nitro, sulfoxy, sulfonyl, alkoxy, thioalkoxy, trihalomethyl and the like.

Alternatively, said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR,R',R''$^+$Z$^-$, wherein R, R', R'' is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to ally compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as modulators of the Bax function, e.g. Bax inhibitors (antagonists).

Quite surprisingly, it was now found that the pyrrolidine derivatives according to formula I are suitable pharmaceutically active agents, notably by effectively modulating the Bax function or by modulating the Bax activation or expression. The compounds according to formula I are particularly interesting as they are preferably available to oral administration and therefore provide a good bio-availability. They could be prescribed by a physician and require only minor supervision.

The compounds according to the present invention are those of formula I.

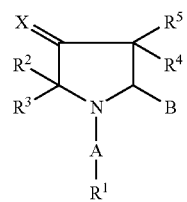

Said formula also comprises its geometrical isomers, its optically active forms as enantiomers, diastereomers and its racemate forms, as well as pharmaceutically acceptable salts thereof. Preferred pharmaceutically acceptable salts of the compound I, are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

In said formula I, X is selected from the group consisting of O, S, $CR^6R^7$, $NOR^6$, $NNR^6R^7$.

A is selected from the group consisting of —(C=O)—, —(C=O)—O—, —C(=NH)—, —(C=O)—NH—, —(C=S)—NH, —$SO_2$—, —$SO_2NH$—, —$CH_2$—.

B is either an amido group of the formula —(C=O)—$NR^8R^9$ or B represents a heterocyclic residue having the formula $B^1$ $$\begin{array}{c} Q-(CH_2)_n \\ \diagup \\ N \diagdown \diagup Y \\ Z-E \diagdown (R^{11})_m \end{array}$$

wherein Q is $NR^{10}$, O or S; n is an integer selected of 0, 1 or 2, preferably 0. m is an integer selected of 0, 1, 2 or 3, preferably 0 or 1.

Y, Z and E form together with the 2 carbons to which they are attached a 5–6 membered aryl or heteroaryl ring.

$R^1$ is selected from the group comprising or consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl group.

$R^2$, $R^3$, $R^4$ and $R^5$ are independently selected from each other from the group consisting of hydrogen, halogen, $C_1$–$C_6$-alkyl, $C_1$–$C_6$-alkoxy, preferably they are all hydrogen.

$R^6$ and $R^7$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, unsubstituted or substituted $C_1$–$C_6$-alkyl heteroaryl.

$R^8$, $R^9$ and $R^{10}$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl.

Alternatively, each pair $R^6$, $R^7$ and/or $R^8$, $R^9$ could form together with the N atom to which they are attached a 3–8 membered saturated or unsaturated substituted or unsubstituted heterocyclic ring which may contain 1–2 further heteroatoms selected from N, S and O and which is optionally fused with an aryl, heteroaryl or 3–8 membered saturated or unsaturated cycloalkyl ring.

$R^{11}$ is selected from the group comprising or consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quarternary ammonium moieties, unsubstituted or substituted saturated or unsaturated 3–8-membered cycloalkyl.

Preferred pyrrolidine derivatives are those compounds according to formula I, wherein B is a group —(C=O)—NHR$^9$, in which R$^9$ is selected from the group consisting of unsubstituted or substituted $C_1$–$C_6$ alkyl, unsubstituted or substituted alkenyl, unsubstituted or substituted alkyl, unsubstituted or substituted saturated or unsaturated 3–6-membered cycloalkyl which optionally contains a N atom, unsubstituted or substituted aryl, unsubstituted or substituted heteroaryl, unsubstituted or substituted $C_1$–$C_2$-alkyl aryl, unsubstituted or substituted $C_1$–$C_2$-alkyl heteroaryl.

Preferred heteroaryls are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzo-furyl, [2,3-dihydro]benzofuryl, isobenzofuryl, benzothienyl, benzotriazolyl, isobenzothienyl, 2,1,3-benzothiadiazolyl, 2,1,3-benzoxadiazolyl, benzodioxolyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, acridinyl or benzoquinolyl and whereby said heteroaryl could be fused with a 3–8-membered cycloalkyl containing optionally 1–3 heteroatoms selected from N, O, S.

According to a further preferred embodiment the pyrrolidine derivatives according to the present invention carry a residue $B^1$ which is a fused heterocycle of the formula

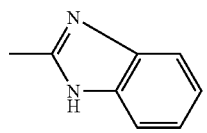

Particularly preferred pyrrolidine derivatives are those compounds according to formula I wherein X is NOR$^6$, and R$^6$ is selected from the group consisting of H, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted acyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-aryl aryl, unsubstituted or substituted $C_1$–$C_6$-alkyl heteroaryl, said cycloalkyl or aryl or heteroaryl groups may be fused with 1–2 further cycloalkyl or aryl or heteroaryl groups. Particularly preferred R$^6$ is H, CH$_3$, unsubstituted or substituted CH$_2$-phenyl or allyl.

Under no circumstances B could be a group COOR or a group —(C=O)NR(OR), whereby R is H, alkyl or acyl.

Such compounds, notably having a group B=hydroxamic acid are described in WO 99/52868 as being potent inhibitors of metalloproteases.

Further particularly preferred pyrrolidine derivatives are those compounds according to formula I wherein X is CHR$^6$, and R$^6$ is selected from the group consisting of halogen, cyano, unsubstituted or substituted $C_3$–$C_6$ allyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, nitro, acyl, alkoxycarbonyl, aminocarbonyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-alkyl aryl, unsubstituted or substituted $C_1$–$C_6$-alkyl heteroaryl, said cycloalkyl or aryl or hetero-aryl groups may be fused with 1–2 further cycloalkyl or aryl or heteroaryl groups. Particularly preferred R$^6$ is halogen, cyano, $C_1$–$C_6$ alkyl or an unsubstituted or substituted phenyl group.

Further preferred pyrrolidine derivatives are those compounds according to formula I, wherein X is O.

According to a further preferred embodiment the pyrrolidine derivatives have a substituent A being —(C=O)—, or —(C=O)—NH—, or —SO$_2$—, most preferred is —(C=O)—.

More preferred groups R$^1$ are unsubstituted or substituted $C_1$–$C_6$-alkyl, $C_2$–$C_6$-alkenyl, unsubstituted or substituted $C_2$–$C_6$-alkynyl, aryl, heteroaryl, saturated or unsaturated 3–8-membered cycloalkyl and still more preferred R$^1$ are $C_1$–$C_6$-alkyl or aryl. A particularly preferred substituent R$^1$ is biphenyl.

According to a most preferred embodiment, the pyrrolidine derivatives according to for-mula I are those wherein X is NOR$^6$ or =CHCl, R$^6$ is a $C_1$–$C_6$-alkyl or aryl or $C_1$–$C_6$-alkyl aryl group, B is an amido group of the formula —(C=O)NHR$^9$), wherein R$^9$ is as above defined, A is C=O and R$^1$ is a $C_1$–$C_6$-alkyl-aryl, an aryl or a $C_1$–$C_6$-alkyl group. Even more preferred are those pyrrolidine derivatives, wherein X is either =CH—Cl, or =NOR$^6$, R$^6$ is a methyl or phenyl group, B is an amido group of the formula —(C=O)NHR$^9$), wherein R$^9$ is a $C_1$–$C_6$-alkyl-aryl, an aryl, a $C_1$–$C_6$-alkyl which is substituted by a primary, secondary or tertiary amine, A is C=O and R$^1$ is a diphenyl methyl or a phenyl group.

The compounds of formula I may contain one or more asymmetric centers and may therefore exist as enantiomers or diasteroisomers. It is to be understood that the invention includes both mixtures and separate individual isomers or enantiomers of the compounds of formula I. In a particularly preferred embodiment the pyrrolidine derivatives according to formula I are obtained in an enantiomeric excess of at least 52% ee, preferably of at least 92–98% ee. Also E/Z isomers with regard to pyrrolidine derivatives having residues X being =CR$^6$R$^7$ whereby both R$^6$R$^7$ are different from each other, and/or with regard to pyrrolidine derivatives having residues X being =NOR$^6$ or =NNR$^6$R$^7$ are comprised by the present invention.

Specific examples of compounds of formula I include the following:

(2S,4EZ)-1-([1,1'-biphenyl]-4-ylcarbonyl)-N-(2-methoxyethyl)-4-(methoxyimino)-2-pyrrolidinecarboxamide (2S,4EZ)-1-([1,1'-biphenyl]-4-ylcarbonyl)-4-(chloromethylene)-N-[(2RS)-2-hydroxy-2-phenethyl]-2-pyrrolidinecarboxamide (2S,4EZ)-1-([1,1'-biphenyl]-4-ylcarbonyl)-N-(2-hydroxyethyl)-4-(methoxyimino)-2-pyrrolidinecarboxamide (2S,4EZ)-1-([1,1'-biphenyl]-4-ylcarbonyl)-N-[(2RS)-2-hydroxy-2-phenethyl]-4-(methoxyimino)-2-pyrrolidinecarboxamide (3EZ,5S)-5-(1H-benzimidazol-2-yl)-1-([1,1'-biphenyl]-4-ylcarbonyl)-3-pyrrolidinone O-methyloxime (2S,4EZ)-N-(2,1,3-benzothiadiazol-4-yl)-1-([1,1'-biphenyl]4-ylcarbonyl)-4-(methoxy-imino)-2-pyrrolidinecarboxamide (2S,4EZ)-1-([1,1'-biphenyl]-4-ylcarbonyl)-4-(methoxyimino)-N-(6-quinolinyl)-2-pyrrolidinecarboxamide (2S,4EZ)-1-acetoacetyl-N-benzyl-4-(methoxyimino)-2-pyrrolidinecarboxamide (2S,4EZ)-1-([1,1'-biphenyl]-4-ylcarbonyl)-4-(chloromethylene)-N-(2-furylmethyl)-2-pyrrolidinecarboxamide (2S,4E)-1-[(4-chlorophenoxy)acetyl]-4-{[(3,4-dichlorobenzyl)oxy]imino}-N-[(2RS)-2-hydroxy-2-phenethyl]-2-pyrrolidinecarboxamide (2S,4EZ)-N-allyl-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-4-(methoxyimino)-N-(2-thienylmethyl)-2-pyrrolidinecarboxamide (2S,4EZ)-4-(cyanomethylene)-N-(2-furylmethyl)-1-[(2-oxo-6-pentyl-2H-pyran-3-yl)carbonyl]-2-pyrrolidinecarboxamide (2S,4EZ)-1-([1,1'-biphenyl]-4-ylcarbonyl)-N-(2-furylmethyl)-4-(methoxyimino)-2-pyrrolidinecarboxamide (2S,4EZ)-1-acetyl-N-cyclopropyl-4-{[(3,4-dichlorobenzyl)oxy]imino}-2-pyrrolidinecarboxamide (2S,4EZ)-N-(2-furylmethyl)-4-(methoxyimino)-1-[(2-oxo-6-pentyl-2H-pyran-3-yl)car-bonyl]-2-pyrrolidinecarboxamide (2S,4EZ)-N-benzyl-1-([1,1'-biphenyl]-4-ylcarbonyl)-4-(methoxyimino)-N-methyl-2-pyrrolidinecarboxamide (2S,4EZ)-1-(diphenylacetyl)-4-(ethoxyimino)-N-(2-thienylmethyl)-2-pyrrolidinecarboxamide (2S,4EZ)-N-(2,1,3-benzothiadiazol-4-yl)-4-(cyanomethylene)-1-(diphenylacetyl)-2-pyrrolidinecarboxamide (3EZ,5S)-5-(1H-benzimidazol-2-yl)-1-(diphenylacetyl)-3-pyrrolidinone O-methyloxime (2S)-2-[1-([1,1'-biphenyl]-4-ylcarbonyl)-4-methylene-2-pyrrolidinyl]-1H-benzimidazole (2S,4EZ)-1-([1,1'-biphenyl]-4-ylcarbonyl)-4-(chloromethylene)-N-(2-methoxyethyl)-2-pyrrolidinecarboxamide (3EZ,5S)-5-(1H-benzimidazol-2-yl)-1-(diphenylacetyl)-3-pyrrolidinone O-allyloxime (2S,4EZ)-1-([1,1'-biphenyl]-4-ylcarbonyl)-N-[2-(diethylamino)ethyl]-4-(methoxyimino)-2-pyrrolidinecarboxamide (2S,4EZ)-1-(diphenylacetyl)-4-{[(4-methoxybenzyl)oxy]imino}-N-(2-thienylmethyl)-2-pyrrolidinecarboxamide (2S,4EZ)-1-([1,1'-biphenyl]-4-ylcarbonyl)-N-(3,4-dimethoxybenzyl)-4-(methoxyimino)-2-pyrrolidinecarboxamide (2S,4EZ)-1-acetoacetyl-4-(methoxyimino)-N-(1-naphthylmethyl)-2-pyrrolidinecarboxamide (2S,4EZ)-N-allyl-4-{[(3,4-dichlorobenzyl)oxy]imino}-1-(diphenylacetyl)-2-pyrrolidinecarboxamide (2S,4EZ)-4-{[(3,4-dichlorobenzyl)oxy]imino}-$N^1$-pentyl-$N^2$-(6-quinolinyl)-1,2-pyrrolidinedicarboxamide (2S,4EZ)-4-(chloromethylene)-1-(diphenylacetyl)-N-[(2RS)-2-hydroxy-2-phenethyl]-2-pyrrolidinecarboxamide (2S)-1-([1,1'-biphenyl]-4-ylcarbonyl)-N-[(2RS)-2-hydroxy-2-phenethyl]-4-methylene-2-pyrrolidine-carboxamide (2S,4EZ)-1-([1,1'-biphenyl]-4-ylcarbonyl)-4-(chloromethylene)-N-6-quinolinyl)-2-pyrrolidinecarboxamide (2S,4EZ)-4-benzylidene-N-[2-(diethylamino)ethyl]-1-(diphenylacetyl)-2-pyrrolidinecarboxamide (2S,4EZ)-1-acetoacetyl-4-(methoxyimino)-N-(2-thienylmethyl)-2-pyrrolidinecarboxamide (2S,4EZ)-1-acetyl-4-{[(3,4-dichlorobenzyl)oxy]imino}-N-[(2RS)-2-hydroxy-2-phenethyl]-2-pyrrolidinecarboxamide (2S,4EZ)-4-{[(3,4-dichlorobenzyl)oxy]imino}-$N^1$-(3,5-dichlorophenyl)-$N^2$-(6-quinolinyl)-1,2-pyrrolidinedicarboxamide (2S,4EZ)-4-(methoxyimino)-N-(1-naphthylmethyl)-1-(phenoxyacetyl)-2-pyrrolidinecarboxamide (2S,4EZ)-4-(chloromethylene)-N-(3,4-dimethoxybenzyl)-1-[(2-oxo-6-pentyl-2H-pyran-3-yl)carbonyl]-2-pyrrolidinecarboxamide (2S,4EZ)-1-(diphenylacetyl)-4-(methoxyimino)-N-(2-thienylmethyl)-2-pyrrolidinecarboxamide (2S,4EZ)-N-benzyl-1-(diphenylacetyl)-4-(methoxyimino)-2-pyrrolidinecarboxamide (2S,4EZ)-1-([1,1'-biphenyl]-4-ylcarbonyl)-4-{[(3,4-dichlorobenzyl)oxy]imino}-N-[2-(diethylamino)ethyl]-2-pyrrolidinecarboxamide (2S,4EZ)-4-{[(3,4-dichlorobenzyl)oxy]imino}-1-[4-(dimethylamino)butanoyl]-N-(6-quinolinyl)-2-pyrrolidinecarboxamide (2S,4EZ)-1-([1,1'-biphenyl]-4-ylcarbonyl)-N-(5-ethyl-1,3,4-thiadiazol-2-yl)-4-(methoxyimino)-2-pyrrolidinecarboxamide (2S,4EZ)-N-benzyl-1-([1,1'-biphenyl]-4-ylcarbonyl)-4-(methoxyimino)-2-pyrrolidinecarboxamide (2S,4EZ)-N-benzyl-1-(diphenylacetyl)-4-(ethoxyimino)-2-pyrrolidinecarboxamide (2S,4EZ)-$N^2$-Cyclopropyl-4-{[(3,4-dichlorobenzyl)oxy]imino}-$N^1$-(3-methoxyphenyl)-1,2-pyrrolidinedicarboxamide (2S,4EZ)-1-(diphenylacetyl)-N-[(2RS)-2-hydroxy-2-phenethyl-4-{[(4-methoxybenzyl)-oxy]imino}-2-pyrrolidinecarboxamide (2S)-N-(2-furylmethyl)-4-methylene-1-[(2-oxo-6-pentyl-2H-pyran-3-yl)carbonyl]-2-pyrrolidine-carboxamide (2S,4EZ)-N-(2,1,3-benzothiadiazol-4-yl)-1-(diphenylacetyl)-4-(methoxyimino)-2-pyrrolidinecarboxamide (2S,4EZ)-N-benzyl-1-(diphenylacetyl)-4-{[(4-methoxybenzyl)oxy]imino}-2-pyrrolidinecarboxamide (2S,4EZ)-1-benzoyl-4-{[(3,4-dichlorobenzyl)oxy]imino}-N-(6-quinolinyl)-2-pyrrolidinecarboxamide (2S,4EZ)-1-acetoacetyl-N-cyclopropyl-4-{[(3,4-dichlorobenzyl)oxy]imino}-2-pyrrolidinecarboxamide (2S,4EZ)-4-{[(3,4-dichlorobenzyl)oxy]imino} $N^2$-[(2RS)-2-hydroxy-2-phenethyl]-$N^1$-pentyl-1,2-pyrrolidinedicarboxamide (2S,4EZ)-4-[(benzyloxy)imino]-N-(1-naphthylmethyl)-1-(phenoxyacetyl)-2-pyrrolidinecarboxamide (2S)-1-([1,1'-biphenyl]-4-ylcarbonyl)-4-methylene-N-(6-quinolinyl)-2-pyrrolidinecarboxamide (2S,4EZ)-N-cyclopropyl-4-{[(3,4-dichlorobenzyl)oxy]imino}-(diphenylacetyl)-2-pyrrolidinecarboxamide (2S,4EZ)-1-(4-Cyanobenzoyl)-4-{[(3,4-dichlorobenzyl)oxy]imino}-N-(6-quinolinyl)-2-pyrrolidinecarboxamide (2S,4EZ)-N-cyclopropyl-4-{[(3,4-dichlorobenzyl)oxy]imino}-1-(methoxyacetyl)-2-pyrrolidinecarboxamide (2S,4EZ)-N-(1,3-benzodioxol-5-ylmethyl)-1-([1,1'-biphenyl]-4-ylcarbonyl)-4-(methoxyimino)-2-pyrrolidinecarboxamide (3EZ,5S)-5-[(4-acetyl-1-piperazinyl)carbonyl]-1-acryloyl-3-pyrrolidinone O-(3,4-dichlorobenzyl)oxime (2S)-1-([1,1'-biphenyl]-4-ylcarbonyl)-N-(2-furylmethyl)-4-methylene-2-pyrrolidinecarboxamide (2S,4EZ)-4-(cyanomethylene)-N-(3,4-dimethoxybenzyl)-1-[(2-oxo-6-pentyl-2H-pyran-3-yl)carbonyl]-2-pyrrolidinecarboxamide (2S,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-3-ylcarbonyl)-N-[(2RS)-2-hydroxy-2-phenylethyl]-4-(methoxyimino)-2-pyrrolidinecarboxamide (2S,4EZ)-1-(4-benzoylbenzoyl)-N-[(2RS)-2-hydroxy-2-phenylethyl]-4-(methoxyimino)-2-pyrrolidinecarboxamide (2S,4EZ)-N-[(2RS)-2-hydroxy-2-phenylethyl]-4-(methoxyimino)-1-(3-phenoxybenzoyl)-2-pyrrolidinecarboxamide (2S,4EZ)-N-[(2RS)-2-hydroxy-2-phenylethyl]-4-(methoxyimino)-1-(2-phenoxybenzoyl)-2-pyrrolidinecarboxamide (2S,4EZ)-N-[(2S)-2-hydroxy-2-phenylethyl]4-(methoxyimino)-1-[(2'-methyl[1,1'-biphenyl]-4-yl)carbonyl]-2-pyrrolidinecarboxamide (2S,4EZ)-N-[(2R)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-N-(2-hydroxyethyl)-4-(methoxyimino)-1-[(2'-methyl[1,1'-biphenyl]-4-yl)carbonyl]-2-pyrrolidinecarboxamide (2S,4EZ)-N-(2-hydroxyethyl)-4-(methoxyimino)-N-methyl-1-[(2'-methyl[1,1'-biphenyl]-4-yl)carbonyl]-2-pyrrolidinecarboxamide (2S,4EZ)-1-([1,1'-biphenyl]-4-ylsulfonyl)-N-[(1S,2S,3R,4R)-3-(hydroxymethyl)bicyclo[2.2.1]hept-2-yl]-4-(methoxyimino)-2-pyrrolidinecarboxamide (2S,4EZ)-1-([1,1'-biphenyl]-4-ylcarbonyl)-N-(trans-4-hydroxycyclohexyl)-4-(methoxyimino)-2-pyrrolidinecarboxamide (2S,4EZ)-1-([1,1'-biphenyl]-4-ylcarbonyl)-N-[(1R,2R)-2-(hydroxymethyl)cyclohexyl]-4-(methoxyimino)-2-pyrrolidinecarboxamide (2S,4EZ)-1-([1,1'-biphenyl]-4-ylcarbonyl)-N-[(2RS)-2-hydroxy-3-phenoxypropyl]-4-(methoxyimino)-2-pyrrolidinecarboxamide (2S,4EZ)-N-[(2RS)-2-hydroxy-3-phenoxypropyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(2RS)-2-hydroxy-3-phenoxypropyl]-4-(methoxyimino)-2-pyrrolidinecarboxamide (2S,4EZ)-1-([1,1'-biphenyl]-4-ylcarbonyl)-N-[(2RS)-2-hydroxy-2-(4-hydroxyphenyl)ethyl)-4-(methoxyimino)-2-pyrrolidinecarboxamide (2S,4EZ)-1-([1,1'-biphenyl]-4-ylsulfonyl)-N-[(2R,S)-2-hydroxy-2-(4-hydroxyphenyl)ethyl]-4-(methoxyimino)-2-pyrrolidinecarboxamide (2S,4EZ)-1-([1,1'-biphenyl]-4-ylcarbonyl)-N-[(]-hydroxycyclohexyl)methyl]-4-(methoxyimino)-2-pyrrolidinecarboxamide (2S,4EZ)-N-[(1-hydroxycyclohexyl)methyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(1-hydroxycyclohexyl)methyl]-4-(methoxyimino)-2-pyrrolidinecarboxamide (2S,4EZ)-1-([1,1'-biphenyl]4-ylcarbonyl)-N-[(2R,)-2-(3,4-dihydroxyphenyl)-2-hydroxyethyl]-4-(methoxyimino)-2-pyrrolidinecarboxamide (2S,4EZ)-N-[(2S)-2-hydroxy-2-phenylethyl]-4-(methoxyimino)-1-[4-(4-pyridinyl)benzoyl]-2-pyrrolidinecarboxamide (2S,4EZ)-N-[(2S)-2-hydroxy-2-phenylethyl]-4-(methoxyimino)-1-[4-(3-pyridinyl)benzoyl]-2-pyrrolidinecarboxamide (2S,4EZ)-N-[(2S)-2-hydroxy-2-phenylethyl]-4-(methoxyimino)-1-[4-(2-pyridinyl)benzoyl]-2-pyrrolidinecarboxamide (2S,4EZ)-1-([1,1'-biphenyl]-4-ylcarbonyl)-N-[(2RS)-2,3-dihydroxypropyl]-4-(methoxyimino)-2-pyrrolidinecarboxamide (2S,4EZ)-1-([1,1'-biphenyl]-4-ylsulfonyl)-N-[(2RS)-2,3-dihydroxypropyl]-4-(methoxyimino)-2-pyrrolidinecarboxamide (2S,4EZ)-1-([1,1'-biphenyl]4-ylcarbonyl)-N-[(2RS)-2-hydroxy-3-(4-methoxyphenoxy)propyl]-4-(methoxyimino)-2-pyrrolidinecarboxamide (2S,4EZ)-N-[(2RS)-2-hydroxy-3-(4-methoxyphenoxy)propyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(2RS)-2-hydroxy-3-(4-methoxyphenoxy)-propyl]-4-(methoxyimino)-2-pyrrolidinecarboxamide (2S,4EZ)-4-([1,1'-biphenyl]-4-ylcarbonyl)-N-[(2RS)-2-hydroxypropyl]-4-(methoxyimino)-2-pyrrolidinecarboxamide (2S,4EZ)-1-([1,1'-biphenyl]4-ylsulfonyl)-N-[(2RS)-2-hydroxypropyl]-4-(methoxyimino)-2-pyrrolidinecarboxamide (2S,4EZ)-1-([1,1'-biphenyl]-4-ylsulfonyl)-N-[(2RS)-2-hydroxy-2-(2-naphthyl)ethyl]4-(methoxyimino)-2-pyrrolidinecarboxamide (2S,4EZ)-1-([1,1'-biphenyl]-4-ylcarbonyl)-N-[(2RS)-2-hydroxy-2-(4-nitrophenyl)ethyl]-4-(methoxyimino)-2-pyrrolidinecarboxamide (2S,4EZ)-N-[(2RS)-2-hydroxy-2-(4-nitrophenyl)ethyl]-4-(methoxyimino)-1-[4-(4-pyridinyl)benzoyl]-2-pyrrolidinecarboxamide (2S,4EZ)-N-[(2RS)-2-hydroxy-2-(4-nitrophenyl)ethyl]-4-(methoxyimino)-1-[4-(3-pyridinyl)benzoyl]-2-pyrrolidinecarboxamide (2S,4EZ)-N-[(2RS)-2-hydroxy-2-(4-nitrophenyl)ethyl]-4-(methoxyimino)-1-[4-(2-pyridinyl)benzoyl]-2-pyrrolidinecarboxamide (2S,4EZ)-1-([1,1'-biphenyl]-4-ylsulfonyl)-N-[(2RS)-2-hydroxy-2-(4-nitrophenyl)ethyl]-4-(methoxyimino)-2-pyrrolidinecarboxamide (2S,4EZ)-N-{(2RS)-3-[4-(acetylamino)phenoxy]-2-hydroxypropyl}-1-([1,1-biphenyl]-4-ylcarbonyl)-4-(methoxyimino)-2-pyrrolidinecarboxamide (2S,4EZ)-N-{(2RS)-3-[4-(acetylamino)phenoxy]-2-hydroxypropyl}-4-(methoxyimino)-1-[4-(4-pyridinyl)benzoyl]-2-pyrrolidinecarboxamide (2S,4EZ)-N-{(2RS)-3-[4-(acetylamino)phenoxy]-2-hydroxypropyl}-4-(methoxyimino)-1-[4-(3-pyridinyl)benzoyl]-2-pyrrolidinecarboxamide (2S,4EZ)-N-{(2RS)-3-[4-(acetylamino)phenoxy]-2-hydroxypropyl}-1-([1,1'-biphenyl]-4-ylsulfonyl)-4-(methoxyimino)-2-pyrrolidinecarboxamide (2S,4EZ)-1-([1,1'-biphenyl]-4-ylcarbonyl)-N-[(2R)-2-hydroxy-2-phenylethyl]-4-(methoxyimino)-2-pyrrolidinecarboxamide (2S,4EZ)-N-[(2R)-2-hydroxy-2-phenylethyl]-4-(methoxyimino)-1-[4-(4-pyridinyl)benzoyl]-2-pyrrolidinecarboxamide (2S,4EZ)-N-[(2R)-2-hydroxy-2-phenylethyl]-4-(methoxyimino)-1-[4-(3-pyridinyl)benzoyl]-2pyrrolidinecarboxamide (2S,4EZ)-N-[(2R)-2-hydroxy-2-phenylethyl]4-(methoxyimino)-1-[4-(2-pyridinyl)benzoyl]-2-pyrrolidinecarboxamide (2S,4EZ)-1-([1,1'-biphenyl]-4-ylsulfonyl)-N[(2R)-2hydroxy-2-phenylethyl]-4(methoxyimino)-2-pyrrolidinecarboxamide (2S,4EZ)-1-([1,1'-biphenyl]-4-ylsulfonyl)-N-(3-hydroxypropyl)-4-(methoxyimino)-2pyrrolidinecarboxamide (3EZ,5S)-1-([1,1'-biphenyl]4-ylcarbonyl)-5-[(4-hydroxy-4-phenyl-1-piperidinyl)carbonyl]-3-pyrrolidinone O-methyloxime (3EZ,5S-5-[(4-hydroxy-4-phenyl-1-piperidinyl)carbonyl]-1-[4-(4-pyridinyl)benzoyl]-3-pyrrolidinone O-methyloxime (3EZ,5S)-5-[(4-hydroxy-4-phenyl-1-piperidinyl)carbonyl]-1-[4(3-pyridinyl)benzoyl]-3pyrrolidinone O-methyloxime (3EZ,5S)-1-([1,1'-biphenyl]-4-ylsulfonyl)-5-[(4-hydroxy-4-phenyl-1-piperidinyl)carbonyl]3-pyrrolidinone O-methyloxime (2S,4EZ)-1-([1,1'-biphenyl]-4-ylcarbonyl)-N-[(1S,2S)-2-hydroxycyclohexyl]-4(methoxyimino)-2-pyrrolidinecarboxamide (2S,4EZ)-1-([1,1'-biphenyl]-4-ylsulfonyl)-N-[(1S,2S)-2-hydroxycyclohexyl]-4-(methoxyimino)-2-pyrrolidinecarboxamide (2S,4EZ)-N-benzyl-1-([1,1'-biphenyl]-4-ylcarbonyl)-N-(2-hydroxyethyl)-4(methoxyimino)-2-pyrrolidinecarboxamide (2S,4EZ)-N-benzyl-N-(2-hydroxyethyl)-4-(methoxyimino)-1-[4-(3-pyridinyl)benzoyl]-2-pyrrolidinecarboxamide (3EZ,5S)-1-([1,1'-biphenyl]-4-ylcarbonyl)-5-{[(3RS)-3-hydroxypiperidinyl]carbonyl}-3-pyrrolidinone O-methyloxime (3EZ,5S)-5-{[(3RS)-3-hydroxypiperidinyl]carbony}-1-[4-(4-pyridinyl)benzoyl]-3-pyrrolidinone O-methyloxime (3EZ,5S)-5-{[(3RS)-3-hydroxypiperidinyl]carbonyl}-1-[4-(3-pyridinyl)benzoyl]-3-pyrrolidinone O-methyloxime (3EZ,5S)-1-([1,1'-biphenyl]-4-ylsulfonyl)-5-{[(3RS)-3-hydroxypiperidinyl]carbonyl}-3-pyrrolidinone O-methyloxime (2S,4EZ)-1-([1,1'-biphenyl]4-ylcarbonyl)-N-[(1S,2S)-2-hydroxy-1-(hydroxymethyl)-2-phenylethyl]-4-(methoxyimino)-2-pyrrolidinecarboxamide (2S,4EZ)-N-[(1S,2S)-2-hydroxy-1-(hydroxymethyl)-2-phenylethyl]-4-(methoxyimino)-1-[4-(4-pyridinyl)benzoyl]-2-pyrrolidinecarboxamide (2S,4EZ)-N-[(1S,2S)-2-hydroxy-1-(hydroxymethyl)-2-phenylethyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(1S,2S)-2-hydroxy-1-(hydroxymethyl)-2-phenylethyl]-4-(methoxyimino)-2-pyrrolidinecarboxamide (2S,4EZ)-N-(2-anilinoethyl)-1-([1,1'-biphenyl]-4-ylcarbonyl)-4-(methoxyimino)-2-pyrrolidinecarboxamide (2S,4EZ)-N-(2-anilinoethyl)-4-(methoxyimino)-1-[4-(4-pyridinyl)benzoyl]-2-pyrrolidinecarboxamide (2S,4EZ)-N-(2-anilinoethyl)-4-(methoxyimino)-1-[4-(3-pyridinyl)benzoyl]-2-pyrrolidinecarboxamide (2S,4EZ)-N-(2-anilinoethyl)-4-(methoxyimino)-1-[4-(2-pyridinyl)benzoyl]-2-pyrrolidinecarboxamide (2S,4EZ)-N-(2-anilinoethyl)-1-([1,1'-biphenyl]-4-ylsulfonyl)-4-(methoxyimino)-2-pyrrolidinecarboxamide (3EZ,5S)-1-([1,1'-biphenyl]-4-ylcarbonyl)-5-[(4-hydroxy-1-piperidinyl)carbonyl]-3-pyrrolidinone O-methyloxime (3EZ,5S)-1-([1,1'-biphenyl]-4-ylsulfonyl)-5-[(4-hydroxy-1-piperidinyl)carbonyl]-3-pyrrolidinone O-methyloxime (2S,4EZ)-N-[(1S,2R,3S,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide (2S,4EZ)-N-(3-amino-3-oxopropyl)-1-([1,1'-biphenyl]-4-ylcarbonyl)-4-(methoxyimino)-2pyrrolidinecarboxamide (2S,4EZ)-N-[(1S,2S,3R,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide (2S,4EZ)-1-([1,1'-biphenyl]-4-ylcarbonyl)-N-(4-hydroxybutyl)-4-(methoxyimino)-2-pyrrolidinecarboxamide (2S,4EZ)-1-([1,1'-biphenyl]-4-ylsulfonyl)-N-(4-hydroxybutyl)-4-(methoxyimino)-2-pyrrolidinecarboxamide (2S,4EZ)-1-([1,1'-biphenyl]-4-ylsulfonyl)-N-[(1R,2R)-2-hydroxymethyl)cyclohexyl]-4-(methoxyimino)-2-pyrrolidinecarboxamide (2S,4EZ)-1-([1,1'-biphenyl]-4-ylsulfonyl)-N-[(1R,2S,3R,4S)-3-(hydroxymethyl)bicyclo-[2.2.1]hept-2-yl]-4-(methoxyimino)-2-pyrrolidinecarboxamide (2S,4EZ)-1-([1,1'-biphenyl]-4-ylsulfonyl)-N-[(1R,2S)-2-(hydroxymethyl)cyclohexyl]-4-(methoxyimino)-2-pyrrolidinecarboxamide (2S,4E and 4Z)-N-[(2RS)-2-hydroxy-2-phenylethyl]4-(methoxyimino)-1-[(2'-methyl[1,1-biphenyl]-4-yl)carbonyl]-2-pyrrolidinecarboxamide (2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (2S,4E and 4Z)-N-[(2R)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(1R,2S)-2-(hydroxymethyl)cyclohexyl-4-(methoxyimino)-2-pyrrolidinecarboxamide (2S,4EZ)-1-([1,1'-biphenyl]-4-ylcarbonyl)-N-[2-hydroxy-1-(hydroxymethyl)ethyl]-4-(methoxyimino)-2-pyrrolidinecarboxamide (2S,4EZ)-N-[(1S,2R,3S,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-N-[(1S,2S,3R,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-[(2S)-2-hydroxy-2-phenylethyl]-4-(methoxyimino)-2-pyrrolidinecarboxamide (2RS)-3-({[(2S,4EZ)-1-([1,1'-biphenyl]-4-ylcarbonyl)-4-(methoxyimino)pyrrolidinyl]-carbonyl}amino)-2-hydroxypropanoic acid (2S,4EZ)-N-[(1R,2S)-2-(aminocarbonyl)cyclohexyl]-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-[(1RS)-2-hydroxy-1-methylethyl)-4-(methoxyimino)-2-pyrrolidinecarboxamide (2S,4EZ)-1-([1,1'-biphenyl]-4-ylcarbonyl)-N-[(1S,2S)-2-hydroxy-1-(hydroxymethyl)-2-(4-nitrophenyl)ethyl]-4-(methoxyimino)-2-pyrrolidinecarboxamide 4-({[(2S,4EZ)-1-([1,1'-biphenyl]-4-ylcarbonyl)-4-(methoxyimino)pyrrolidinyl]carbonyl}-amino)butanoic acid (2S,4EZ)-N-[(2S)-2-hydroxy-2-phenylethyl]-1-[(2'-methoxy[1,1'-biphenyl]-4yl)carbonyl]-4-(methoxyimino)-2-pyrrolidinecarboxamide (2S,4EZ)-N-[(2RS)-2-hydroxy-2-(2-naphthyl)ethyl]-1-[(2'-methoxy[1,1'-biphenyl]-4-yl)carbonyl]4-(methoxyimino)-2-pyrrolidinecarboxamide (2S,4EZ)-N-[(1RS)-2-hydroxy-1-methylethyl]4-(methoxyimino)-1-[(2'-methyl[1,1'-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4-(methoxyimino)-1-[(2'-methyl[1,1'-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4 (methoxyimino)-1-[(2'-methoxy[1,1'-biphenyl]-4-yl)carbonyl]-2-pyrrolidinecarboxamide (3EZ,5S)-5-[(4-hydroxy-1-piperidinyl)carbonyl)-1-[(2'-methyl[1,1'-biphenyl]4-yl)carbonyl]-3-pyrrolidinone O-methyloxime (2S,4EZ)-N-[(1S,2S,3R,4R)-3-(aminocarbonyl)bicyclo[2.2.1]hept-5-en-2-yl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-phenylethyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxypropyl]-4-(methoxyimino)-1-[(2'-methyl[1,1'-biphenyl]-4-yl)carbonyl]-2-pyrrolidinecarboxamide (2S,4EZ)-N-[(2RS)-2,3-dihydroxypropyl]-4-(methoxyimino)-1-[(2'-methyl[1,1'-biphenyl]-4-yl)carbonyl]-2-pyrrolidinecarboxamide (2S,4EZ)-N-(3-hydroxypropyl)-4-(methoxyimino)-1-[(2'-methyl[1,1'-biphenyl]-4-yl)carbonyl]-2-pyrrolidinecarboxamide (2S,4EZ)-N-(2-amino-2-oxoethyl)-1-([1,1'-biphenyl]-4-ylcarbonyl)-4-(methoxyimino)-2-pyrrolidinecarboxamide (2S,4EZ)-N-(2-amino-2-oxoethyl)-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(2RS)-2-hydroxy-2-(3-hydroxyphenyl)ethyl]-4-(methoxyimino)-2-pyrrolidinecarboxamide (2S,4EZ)-1-([1,1'-biphenyl]-4-ylcarbonyl)-N-[(1S,2R,3S,4R)-3-(hydroxymethyl)-bicyclo[2.2.1]hept-2-yl]-4-(methoxyimino)-2-pyrrolidinecarboxamide (2S,4EZ)-N-[(1R,2S,3R,4S)-3-(hydroxymethyl)bicyclo[2.2.1]hept-2-yl]-1-[(2'-methoxy[1,1'-biphenyl]-4-yl)carbonyl]-4-(methoxyimino)-2-pyrrolidinecarboxamide (2S,4EZ)-N-(trans-4hydroxycyclohexyl) 1-[(2'-methoxy[1,1'-biphenyl]-4yl)carbonyl]-4-(methoxyimino)-2-pyrrolidinecarboxamide (2S,4EZ)-N-[(1R,2R)-2-(hydroxymethyl)cyclohexyl]-1-[(2'-methoxy[1,1'-biphenyl]-4-yl)carbonyl]-4(methoxyimino)-2-pyrrolidinecarboxamide (2S,4EZ)-N-[(2RS)-2-hydroxy-3-phenoxypropyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(4-hydroxyphenyl)ethyl]-4-(methoxyimino)-1-[(2'-methyl 1,1'-biphenyl]-4-yl)carbonyl]-2-pyrrolidinecarboxamide (2S,4EZ)-N-[(2R-2-hydroxy-2-(4-hydroxyphenyl)ethyl]-4-(methoxyimino)-1-[(2'-methoxy[1,1'-biphenyl]-4-yl)carbonyl]-2-pyrrolidinecarboxamide (2S,4EZ)-N-[(2RS)-2-hydroxy-2-(4-hydroxy-3-methoxyphenyl)ethyl]1-[(2'-methyl[1,1'-biphenyl]4-yl)carbonyl]-4-(methoxyimino)-2-pyrrolidinecarboxamide (2S,4EZ)-N-[(2RS)-2-hydroxy-2-(4-hydroxy-3-methoxyphenyl)ethyl]-1-[(2'-methoxy[1,1'-biphenyl]-4-yl)carbonyl]-4-(methoxyimino)-2-pyrrolidinecarboxamide (2S,4EZ)-N-[(2RS)-2-(3,4-dihydroxyphenyl)-2-hydroxyethyl]-1-[(2'-methoxy[1,1'-biphenyl]-4-yl)carbonyl]-4-(methoxyimino)-2-pyrrolidinecarboxamide (2R,4EZ)-1-([1,1'-biphenyl]-4-ylcarbonyl)-N-[(2RS)-2-hydroxy-2-phenylethyl]-4-(methoxyimino)-2-pyrrolidinecarboxamide (2R,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-[(2'-cyano[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(3',4'-dichloro[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(2',6'-dimethyl]1,1'-biphenyl]-4-yl)carbonyl]-4-[(2RS)-2-hydroxy-2-phenylethyl]-4-(methoxyimino)-2-pyrrolidinecarboxamide (2S,4EZ)-1-[(2',3-dimethyl[1,1'-biphenyl]4-yl)carbonyl]-N-[(2RS)-2-hydroxy-2-phenylethyl]-4-(methoxyimino)-2-pyrrolidinecarboxamide (2S,4EZ)-N-[(2RS)-2-hydroxy-2-(3-hydroxyphenyl)ethyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(3-hydroxyphenyl)ethyl]-4-(methoxyimino)-1-[(2'-cyano[1,1'-biphenyl]-4-yl)carbonyl]-2-pyrrolidinecarboxamide (2S,4EZ)-N-[(2RS)-2-hydroxy-2-(3-hydroxyphenyl)ethyl]-4-(methoxyimino)-1-[(3',4'-dichloro[1,1-biphenyl]-4-yl)carbonyl]-2-pyrrolidinecarboxamide (2S,4EZ)-N-[(2RS)-2-hydroxy-2-(3-hydroxyphenyl)ethyl]-4-(methoxyimino)-1-[(2',6'-dimethyl[1,1'-biphenyl]-4-yl)carbonyl]-2-pyrrolidinecarboxamide (2S,4EZ)-N-[(2RS)-2-hydroxy-2-(3-hydroxyphenyl)ethyl]-4-(methoxyimino)-1-[(2',3-dimethyl[1,1'-biphenyl]-4-yl)carbonyl]-2-pyrrolidinecarboxamide (2S,4EZ)-1-[(3',4'-dichloro[1,1'-biphenyl]-4-yl)carbonyl]-N-[(2RS)-2-hydroxy-2-(4-hydroxyphenyl)ethyl]4-(methoxyimino)-2-pyrrolidinecarboxamide (2S,4EZ)-1-[(2',6'-dimethyl[1,1'-biphenyl]4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',6'-dimethyl 1,1'-biphenyl]-4-yl)carbonyl]-N-[(2RS)-2-hydroxy-3-(4-methoxyphenoxy)propyl]4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide (2S,4EZ)-N-(2-amino-2-oxoethyl)-1-[(2',6'-dimethyl[1,1'-biphenyl]-4-yl)carbonyl]4-(methoxyimino)-2-pyrrolidinecarboxamide (2S,4EZ)-N-(2-amino-2-oxoethyl)-1-[(2',3-dimethyl[1,1'-biphenyl]-4-yl)carbonyl]-4 (methoxyimino)-2-pyrrolidinecarboxamide (2S,4EZ)-N-(3-amino-3-oxopropyl)-1-[(2',6'-dimethyl[1,1'-biphenyl]-4-yl)carbonyl]-4-(methoxyimino)-2-pyrrolidinecarboxamide (2S,4EZ)-N-(3-amino-3-oxopropyl)-1-[(2',3-dimethyl[1,1'-biphenyl]-4-yl)carbonyl]-4-(methoxyimino)-2-pyrrolidinecarboxamide (2S,4EZ)-1-[(2',6'-dimethyl[1,1'-biphenyl]-4-yl)carbonyl]-N-[2-hydroxy-1-(hydroxymethyl)ethyl]-(methoxyimino)-2-pyrrolidinecarboxamide (2S,4EZ)-1-[(2',3-dimethyl[1,1-biphenyl]-4-yl)carbonyl]-1N-[2-hydroxy-1-(hydroxymethyl)ethyl]-4-(methoxyimino)-2-pyrrolidinecarboxamide (2S,4EZ)-1-[(2'-cyano[1,1'-biphenyl]-4-yl)carbonyl]-N-[(1R,2R)-2-hydroxymethyl)-cyclohexyl]-4-(methoxyimino)-2-pyrrolidinecarboxamide (3EZ,5S)-5-(3,4-dihydro-2(1H)-isoquinolinylcarbonyl)-1-[(2',3-dimethyl[1,1'-biphenyl]-4-yl)carbonyl]-3-pyrrolidinone O-methyloxime (2S,4EZ)-N-[(1R)-2-hydroxy-1-phenylethyl]-4-(methoxyimino)-1-[(2'-methyl[1,1'-biphenyl]-4-yl)carbonyl]-2-pyrrolidinecarboxamide (2S,4EZ)-1-[(2',6'-dimethyl[1,1'-biphenyl]-4-yl)carbonyl]-N-[2-(4-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[2-(4-hydroxyphenyl)ethyl]-4-(methoxyimino)-2-pyrrolidinecarboxamide (2S,4EZ)-1-[(2',6'-dimethyl [1,1'-biphenyl]-4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(1R,2S)-2-hydroxy-1,2-diphenylethyl]-4-(methoxyimino)-2-pyrrolidinecarboxamide (2RS)-2-[({(2S,4EZ)-4-(methoxyimino)-1-[(2'-methyl[1,1'-biphenyl]-4-yl)carbonyl]-pyrrolidinyl}carbonyl)amino]-3-phenylpropanoic acid (2S,4EZ)-N-[(1R,2S)-2-(aminocarbonyl)cyclohexyl]-1-[(2',6'-dimethyl[1,1'-biphenyl]-4-yl)carbonyl]-4-(methoxyimino)-2-pyrrolidinecarboxamide (2S,4EZ)-N-[(1R,2S)-2-(aminocarbonyl)cyclohexyl]-1-[(2',3-dimethyl[1,1'-biphenyl]-4-yl)carbonyl]-4-(methoxyimino)-2-pyrrolidinecarboxamide 4'-{[(2S,4EZ)-2-{[4-(2-hydroxyethyl)-1-piperazinyl]carbonyl})-4-(methoxyimino)-pyrrolidinyl]carbonyl}[1,1'-biphenyl]-2–carbonitrile (3EZ,5S)-1-[(3',4'-dichloro[1,1'-biphenyl]-4-yl)carbonyl]-5-{[4-(2-hydroxyethyl)-1-piperazinyl]carbonyl}-3-pyrrolidinone O-methyloxime (3EZ,5)-1-[(2',6'-dimethyl[1,1'-biphenyl]-4-yl)carbonyl]-5-{[4-(2-hydroxyethyl)-1-piperazinyl]carbonyl}-3-pyrrolidinone O-methyloxime (3EZ,5S)-1-[(2',3-dimethyl[1,1'-biphenyl]-4-yl)carbonyl]-5-{[4-(2-hydroxyethyl)-1-piperazinyl]carbonyl}-3-pyrrolidinone O-methyloxime (3EZ,5S)-1-[(2'-methyl[1,1'-biphenyl]-4-yl)carbonyl]-5-({4-[4-(trifluoromethyl)phenyl]-1-piperazinyl}carbonyl)-3-pyrrolidinone O-methyloxime (3EZ,5S)-1-[(2'-methyl[1,1'-biphenyl]-4-yl)carbonyl]-5-({4-[3-(trifluoromethyl)phenyl]-1-piperazinyl}carbonyl)-3-pyrrolidinone O-methyloxime (2S,4EZ)-4-(methoxyimino)-1-[(2'-methyl[1,1'-biphenyl]-4-yl)carbonyl]-2-pyrrolidinecarboxamide (2S,4EZ)-4-(methoxyimino)-N-methyl-1-[(2'-methyl[1,1'-biphenyl]4-yl)carbonyl]-2-pyrrolidinecarboxamide (2S,4EZ)-4(methoxyimino)-N,N-dimethyl-1-[(2'-methyl[1,1'-biphenyl]-4-yl)carbonyl]-2-pyrrolidinecarboxamide (2S,4EZ)-N-[(3R)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-N-[(3S)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(3R)-3-hydroxy-3-phenylpropyl]-4-(methoxyimino)-2-pyrrolidinecarboxamide (2S,4EZ)-1-([1,1'-biphenyl]-4-ylcarbonyl)-N-[(3S)-3-hydroxy-3-phenylpropyl]-4-(methoxyimino)-2-pyrrolidinecarboxamide (2S,4EZ)-N-[(2S)-2-hydroxy-2-phenylethyl]-4-(methoxyimino)-1-{[2'-(trifluoro-methyl)[1,1'-biphenyl]-4-yl]carbonyl}-2-pyrrolidinecarboxamide (2S,4EZ)-N-[(2S)-2-hydroxy-2-phenylethyl]-4-(methoxyimino)-1-{[2'-chloro[1,1'-biphenyl]-4-yl]carbonyl}-2-pyrrolidinecarboxamide (2S,4EZ)-N-(2-hydroxyphenyl)-4-(methoxyimino)-1-[(2'-methyl[1,1'-biphenyl]-4-yl)carbonyl]-2-pyrrolidinecarboxamide (2S,4EZ)-N-[2-(hydroxymethyl)phenyl]-4-(methoxyimino)-1-[(2'-methyl[1,1'-biphenyl]-4-yl)carbonyl]-2-pyrrolidinecarboxamide (2S,4EZ)-N-[(2S)-2-hydroxy-2-phenylethyl]-4-(methoxyimino)-1-[(2-methyl[1,1'-biphenyl]-4-yl)carbonyl]-2-pyrrolidinecarboxamide (2S,4E and 4Z)-1-([1,1'-biphenyl]-4-ylcarbonyl)-N-[(2S)-2-hydroxy-2-phenylethyl]-4-(methoxyimino)-2-pyrrolidinecarboxamide (2S,4EZ)-4methoxyimino)-1-[(2'-methyl[1,1'-biphenyl]-4-yl)carbonyl]-N-(2-phenylethyl)-2-pyrrolidinecarboxamide (2S)-1-(diphenylacetyl)-N-(1-naphthylmethyl)-4-oxo-2-pyrrolidinecarboxamide (2S)-N1-(3,5-dichlorophenyl)-N2-(3,4-dimethoxybenzyl)-4-oxo-1,2-pyrrolidinedicarboxamide (2S)-4-oxo-1-(phenoxyacetyl)-N-[2-(1H-pyrrol-1-yl)phenyl]-2-pyrrolidinecarboxamide Thereby, the most preferred compounds are those which are selected from the group consisting of:

(4EZ)-1-([1,1'-biphenyl]-4-ylcarbonyl)-N-[2-(diethylamino)ethyl]-4-{[(4-methoxybenzyl)-oxy]imino}-2-pyrrolidinecarboxamide (4EZ)-N$^2$-(2-hydroxyethyl)-4-(methoxyimino)-N$^1$-pentyl-1,2-pyrrolidinedicarboxamide (4EZ)-4-benzylidene-1-([1,1'-biphenyl]-4-ylcarbonyl)-N-[2-(diethylamino)ethyl]-2-pyrrolidinecarboxamide (4EZ)-4-[(alkyloxy)imino]-1-(4–cyanobenzoyl)-N-[2-(1H-pyrrol-1-yl)phenyl]-2-pyrrolidinecarboxamide (4EZ)-4-{[(3,4-dichlorobenzyl)oxy]imino}-N-(2-furylmethyl)-1-[(2-oxo-6-pentyl-2H-pyran-3-yl)carbonyl]-2-pyrrolidinecarboxamide (4EZ)-4-(methoxyimino)-N$^1$-(3-methoxyphenyl)-N$^2$-(2-thienylmethyl)-1,2-pyrrolidinedicarboxamide (4EZ)-2-{[4-(1,3-benzodioxol-5-ylmethyl)-1-piperazinyl]carbonyl}-4-(methoxyimino)-N-pentyl-1-pyrrolidinecarboxamide (2S,4EZ)-N-(2-hydroxyethyl)-4-(methoxyimino)-1-nonanoyl-2-pyrrolidinecarboxamide A further aspect of the present invention is related to the use of the pyrrolidine derivatives according to formula I for the preparation of pharmaceutical compositions for the treatment of diseases including Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

According to a preferred embodiment, the above cited diseases or disease states are treated by the modulation of the Bax function, or the modulation (e.g. the inhibition) of the activation or expression of Bax, respectively, via the use of compounds of formula I, whereby the term Bax function notably comprises the actually active form of Bax as an oligomer (see B. Antonsson et al. in *Biochem. J., Vol.* 345, 2000, pages 271–278). Through the modulation of the Bax function, a convenient method of treatment of disorders mediated by Bax is expected, including in particular neuronal disorders and/or disorders of the immune system. Said modulation could notably involve the inhibition of the activity (activation) and/or of the expression of Bax. Also, said modulation of the Bax function or activity could actually comprise the inhibition or disruption for instance of the Bid interaction with Bax, which has been shown to play a role within the context of the Bax activation leading to cytochrome c release (see J. C. Martinou et al. in *The Journal of Cell Biology*, Vol. 144, No. 5, Mar. 8, 1999, pages 891–901). As a result of the inhibition of the Bax activation by Bid upon using the compounds according to formula I, the cytochrome c release could be inhibited or essentially blocked, thus providing a convenient means to modulate the above described apoptosis pathways. As a result, by said modulation of the apoptosis pathways a whole variety of disorders associated with abnormal apoptosis is expected to be treated.

It is reported herein that the compounds of formula I are suitable to be used as a medicament, i.e. they are suitable for use in treating diseases, like disorders of the autoimmune system and neuronal system of mammals, notably of human beings. More specifically, the compounds according to formula I, alone or in the form of a pharmaceutical composition, are useful for the modulation, in particular for the inhibition, of the Bax function and/or the Bax activation. More specifically, the compounds according to formula I, alone or in the form of a pharmaceutical composition, are useful for the treatment or prevention of disorders associated with abnormal expression or activation of Bax. The compounds according to formula I could be employed alone or in combination with further pharmaceutical agents. The compounds of formula I are suitable to be used as a medicament alone or in the form of a pharmaceutical composition together with suitable carriers, diluents or excipients. The compounds of formula I are suitable to be used for the preparation of orally administrated pharmaceutical compositions.

Thus, according to the present invention, compounds pursuant to formula I are particularly useful for the treatment or prevention of immuno- and/or neuronal-related diseases or pathological states in which preferably the modulation, in particular the inhibition, of the Bax function and/or the Bax activation plays a crucial role, such as neurodegenerative diseases (e.g. Alzheimer's disease, Parkinson's disease, diseases associated with polyglutamine tracts including Huntington's disease, spinocerebellar ataxias and dentatorubral-pallidoluysian atrophy; amyotrophic lateral sclerosis, Crohn's disease, retinitis pigmentosa and multiple sclerosis, epilepsy), ischemia (stroke, myocardial infarction and reperfusion injury), infertility (like premature menopause, ovarian failure or follicular atresia), cardiovascular disorders (arteriosclerosis, heart failure and heart transplantation), renal hypoxia, hepatitis and AIDS.

Still a further aspect of the present invention is related to the actually novel pyrrolidine compounds of formula I. Some very few compounds have actually been disclosed prior to the filing of the present application, without any medical use though. Said known compounds of formula I are those, wherein X is (=$CH_2$), A is —(C=O)—O—, $R^1$ is a t-butyl group and B is —(C=O)—$NMe_2$ (*Tetrahedron* 53(2), 539, 1997); —(C=O)—NHMe (WO 95/47718); —(C=O)—NH—CH(Me)—(C=O)—NH—CH(Me)—COOH (WO 95/47718); or —(C=O)—NH—CH(COO$CH_2$-Ph)—$CH_2$—COOPh (*Tetrahedron* 48(31), 6529, 1992).

X is (=$CHR^6$) with $R^6$ being cyclohexylmethyl, A is —(C=O)—O—, $R^1$ is a t-butyl group and is —(C=O)—NH-t-butyl (*Biorg. Chem. Lett.* 3(8), 1485, 1993).

X is $C_1$–$C_{20}$ alkylidene, A is —(C=O)—O—, $R^1$ is a t-butyl and B is

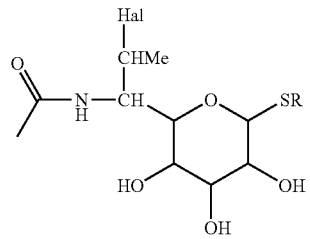

wherein R is $C_1$–$C_{12}$ alkyl and Hal is Cl, Br, J. Said compounds are disclosed in DE-1,932,823 as intermediates.

X is $C_1$–$C_{20}$ alkylidene, A-$R^1$ is a protective group and B is

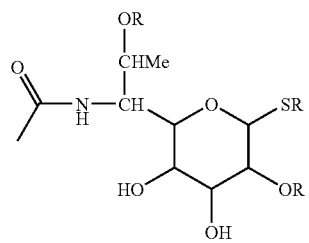

with R being H or $C_1$–$C_{12}$ alkyl (GB-1,118,306)

Also excluded are the following compounds:

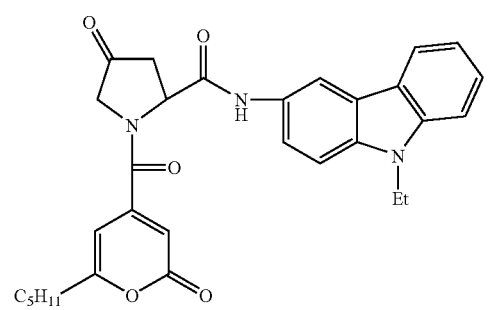

which is disclosed in WO 00/08015 as being an FSH agonist.

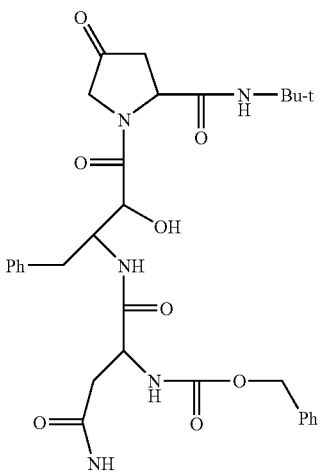

which is disclosed in *Bioorg Med. Chem.* (1996), 4(8), pp.1365–77 as being useful for the treatment of infections.

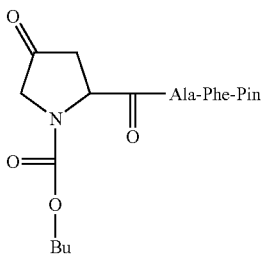

wherein: Pin is —NH—CH[C$_6$H$_3$(OMe)$_2$]C$_6$H$_4$OCHCO-Gly-NH(CH$_2$)$_6$NH-MA/DMA-polyethylene pin (*Tetrahedron Letters*, Vol. 36 (1995) No.28, pp.5081–5084). No biological activity is disclosed for said molecule.

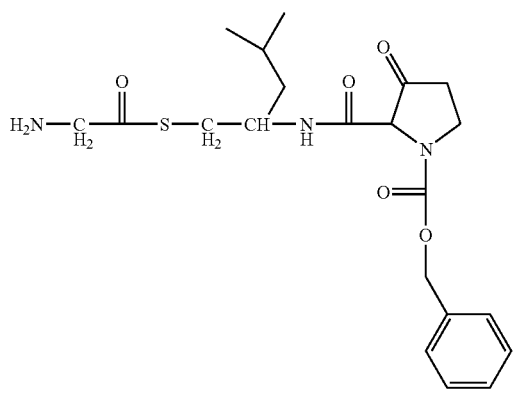

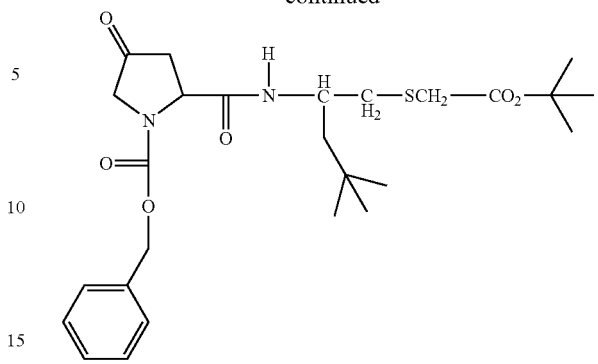

The above two compounds are disclosed in *J. Med. Chem,* 29 (1986) pp.959–971 for their ability to reverse electroconvulsive shock-induced amnesia in rodents.

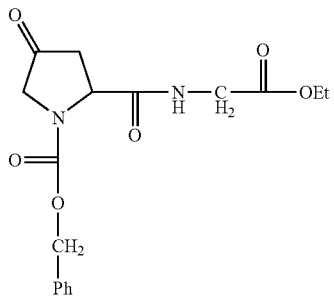

*Int. J. Pept. Protein Res.* (1982), 20(5), pp.438–42.). No biological activity is disclosed for said molecule.

Hence, the novel compounds are those of the formula I, wherein the above mentioned known compounds are excluded.

Still a further object of the present invention is a process for preparing the pyrrolidine derivatives according to formula I.

The pyrrolidine derivatives exemplified in this invention can be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the parti-cular reactants or solvents used, but such conditions can be determined by one skilled in the art by routine optimisation procedures. Generally, the pyrrolidine derivatives according to the general formula I could be obtained by several processes, using both solution-phase and solid-phase chemistry protocols. Depending on the nature of A, B, and X, certain processes will, in some instances, be preferred over others, and it is assumed that the choice of the most suitable process will be obvious to the practitioner skilled in the art.

According to one process, pyrrolidine derivatives according to the general formula I, whereby the substituent B is C(O)—NR$^8$R$^9$, with R$^8$ and R$^9$ being defined as above, are prepared from the corresponding suitably N-protected 4-substituted pyrrolidine derivatives II, whereby the substituent X is as above defined, by solution-phase chemistry protocols such as described in the Examples and shown in Scheme I, below. The suitably N-protected 4-substituted pyrrolidine derivatives II are first reacted with primary or secondary amines III, whereby the substituents $R^8$ and $R^9$ are as above defined, using conditions and methods well known to those skilled in the art to prepare an amide from an amine and a carboxylic acid or a carboxylic acid derivative, using standard peptide coupling agents, such as e.g. DIC, EDC, TBTU, DECP, or others, to yield compounds of formula IV. Removal of the N-protecting group using the appropriate deprotection agents produces deriva-tives of formula V. These can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. from the above mentioned group, to yield the products of general formula I, with B being defined as $C(O)N^8R^9$ (Ia).

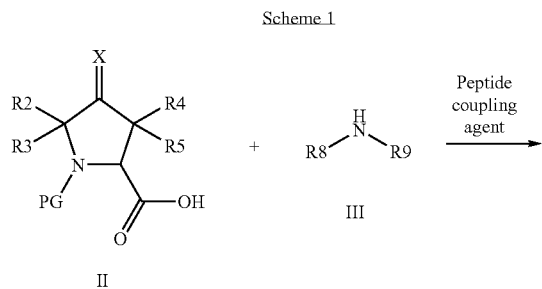

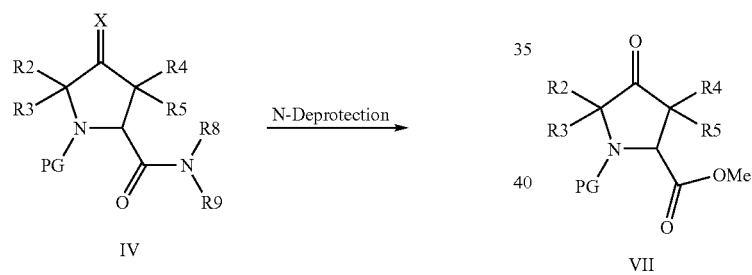

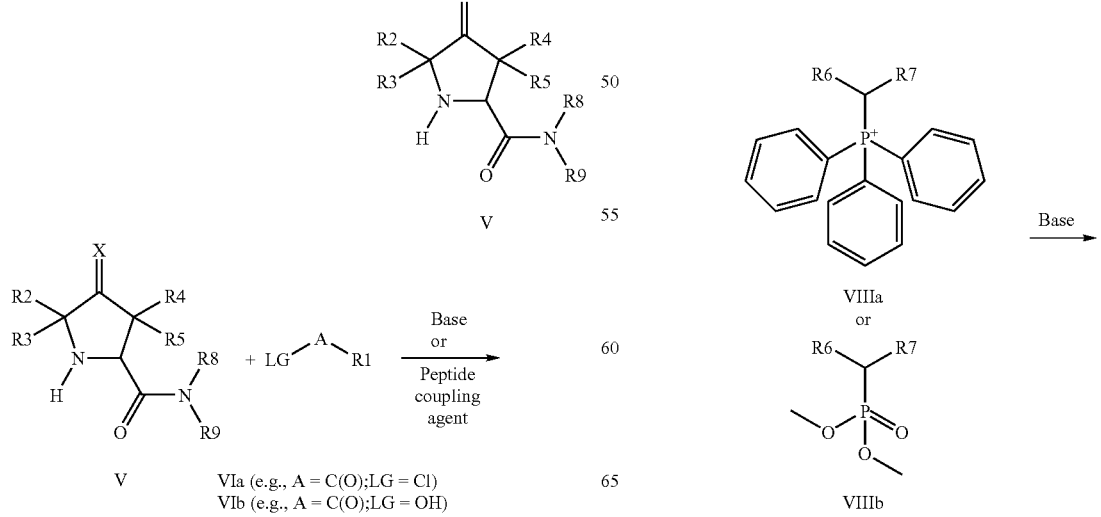

Other derivatives of formula I are prepared using known modifications to the Scheme 1 reaction sequence. Compounds of formula I wherein A is different from the carbonyl functionality are prepared by replacing formula VI compounds with compounds containing the appropriate functional groups, e.g. sulfonyl chlorides, isocyanates, isothiocyanates, chloroformates, substituted alkyl halides, or others to yield sulfonamide, urea, thiourea, carbamate, substituted alkyl derivatives, or others, respectively.

Compounds of formula II, whereby the substituent X is $CR^6R^7$, and $R^6$ and $R^7$ are as above defined, can be prepared from compounds of general formula VII by Wittig-type reactions with anions of phosphoranes such as VIIIa and/or of phosphonates such as VIIIb, followed by saponification of the ester function using standard synthetic techniques, as hereinafter described in the Examples and shown in Scheme 2.

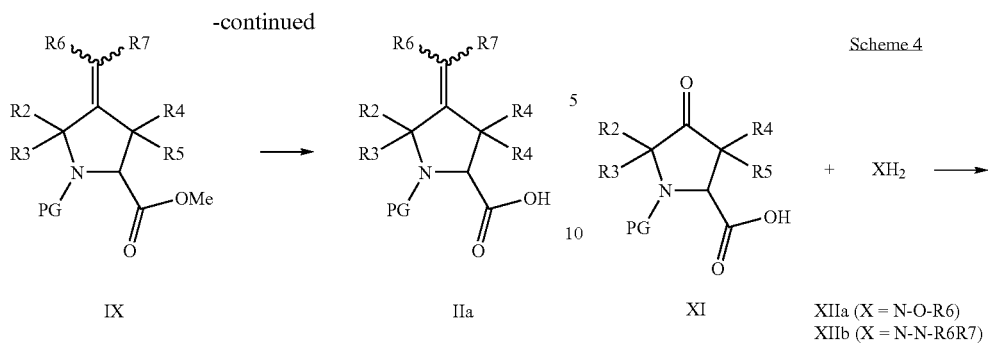

Compounds of general formula VII can be prepared from commercially available, suitably N-protected 4-hydroxyproline X, by a reaction sequence consisting of oxidation and esterification, using standard synthetic techniques as hereinafter described in the Examples and shown in Scheme 3.

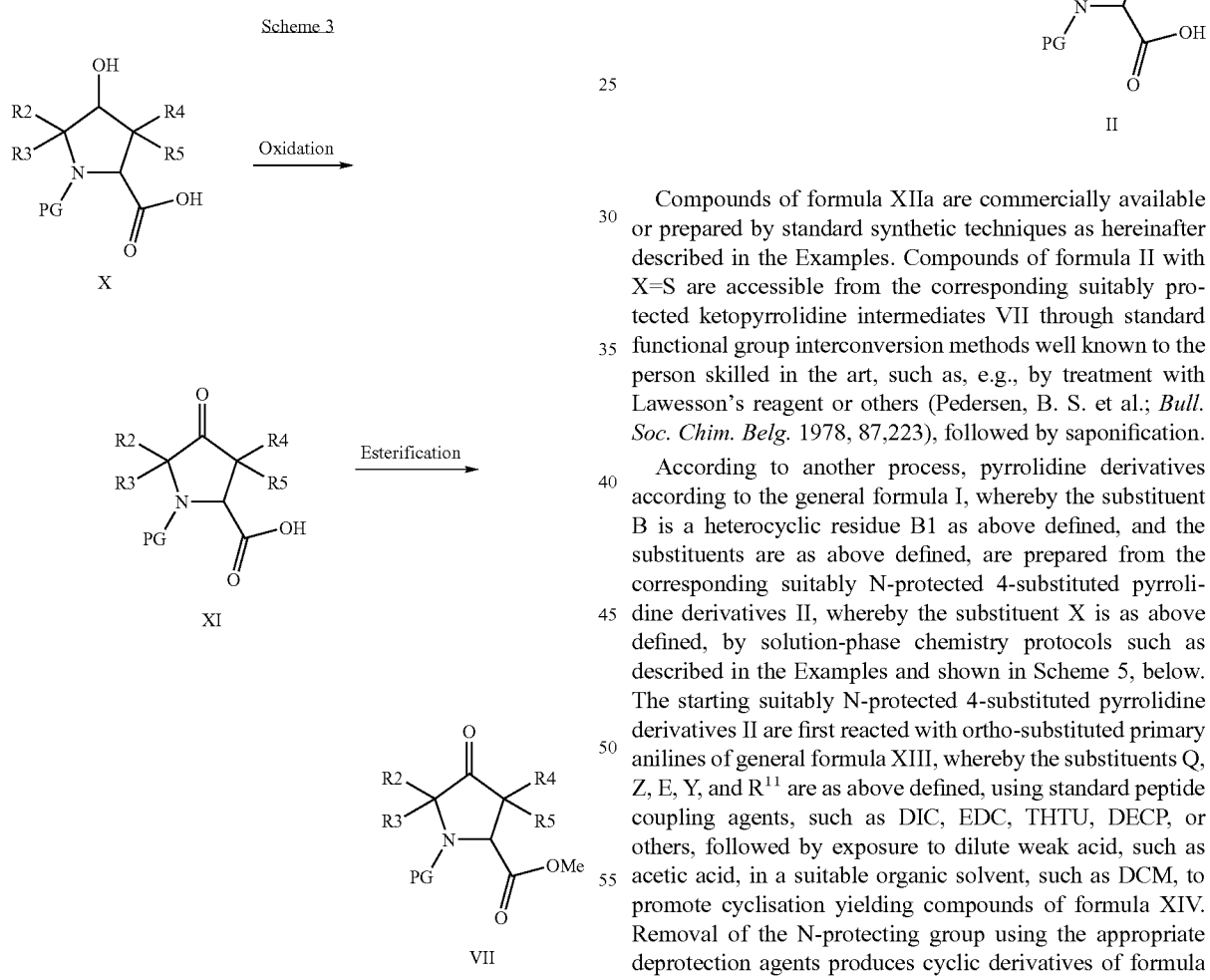

Compounds of formula II, wherein the substituent X is $NOR^6$ or $NNR^6R^7$, and $R^6$ and $R^7$ are as above defined, can be prepared from compounds of general formula XI by reaction with substituted hydroxylamines XIIa and/or substituted hydrazines and/or hydrazides XIIb using standard synthetic techniques as hereinafter described in the Examples and shown in Scheme 4.

Compounds of formula XIIa are commercially available or prepared by standard synthetic techniques as hereinafter described in the Examples. Compounds of formula II with X=S are accessible from the corresponding suitably protected ketopyrrolidine intermediates VII through standard functional group interconversion methods well known to the person skilled in the art, such as, e.g., by treatment with Lawesson's reagent or others (Pedersen, B. S. et al.; *Bull. Soc. Chim. Belg.* 1978, 87,223), followed by saponification.

According to another process, pyrrolidine derivatives according to the general formula I, whereby the substituent B is a heterocyclic residue B1 as above defined, and the substituents are as above defined, are prepared from the corresponding suitably N-protected 4-substituted pyrrolidine derivatives II, whereby the substituent X is as above defined, by solution-phase chemistry protocols such as described in the Examples and shown in Scheme 5, below. The starting suitably N-protected 4-substituted pyrrolidine derivatives II are first reacted with ortho-substituted primary anilines of general formula XIII, whereby the substituents Q, Z, E, Y, and $R^{11}$ are as above defined, using standard peptide coupling agents, such as DIC, EDC, THTU, DECP, or others, followed by exposure to dilute weak acid, such as acetic acid, in a suitable organic solvent, such as DCM, to promote cyclisation yielding compounds of formula XIV. Removal of the N-protecting group using the appropriate deprotection agents produces cyclic derivatives of formula XV. These can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. from the abovementioned group, to yield the products of general formula I, with B being defined as B1 (Ib).

Scheme 5

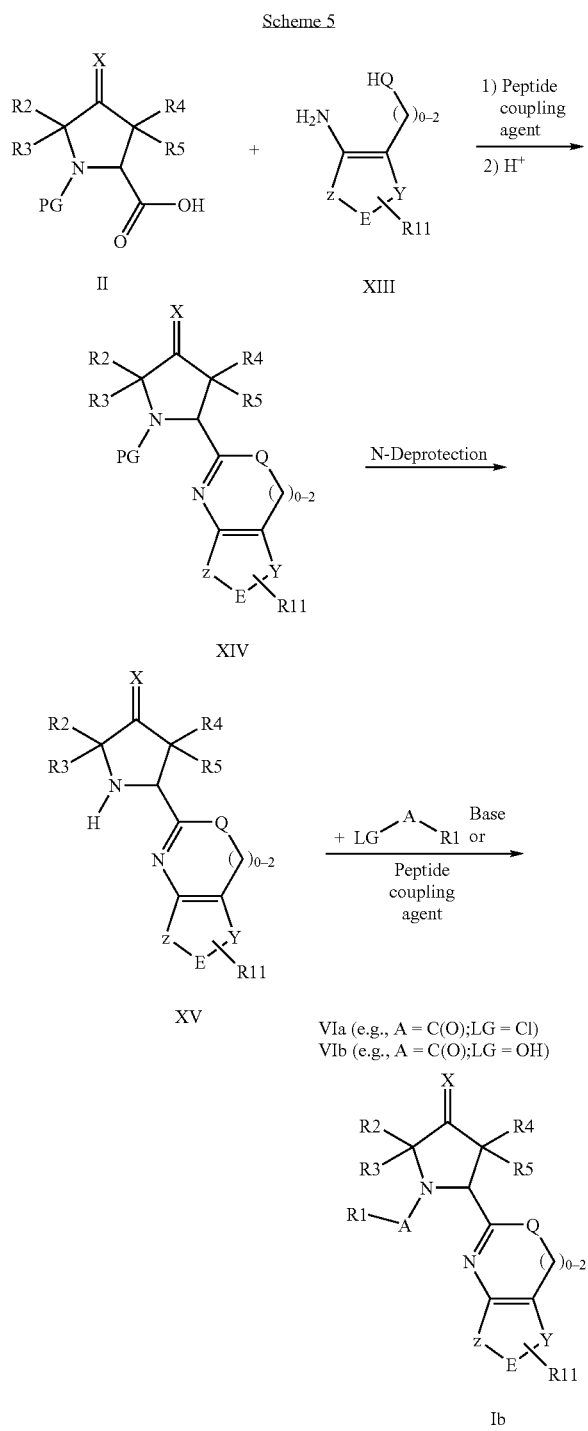

Other derivatives of formula I are prepared using known modifications to the Scheme 5 reaction sequence. Compounds of formula I wherein A is different from the carbonyl functionality are prepared by replacing formula VI with compounds containing the appropriate functional groups, e.g. sulfonyl chlorides, isocyanates, isothiocyanates, chloroformates, substituted alkyl halides, or others to yield sulfonamide, urea, thiourea, carbamate, substituted alkyl derivatives, or others, respectively.

According to another general process, summarized in Scheme 6, pyrrolidine derivatives according to the general formula I, whereby the substituents A, B, X, and $R^1$ are as above defined, are prepared from compounds of formula XVI, using the synthetic techniques as outlined in Schemes 2 and 4. As further shown in Scheme 6, compounds of formula XVI are accessible either from XI, following, e.g., the synthetic methodologies introduced in Schemes 1 and 5, or from Ic through hydrolysis of the methyloxime moiety, e.g. under mild hydrolysis conditions as described hereinafter in the Examples. This present synthetic strategy is most preferred when X is NOH or $NNR^6R^7$, whereby the substituents $R^6$ and $R^7$ are as above defined.

Scheme 6

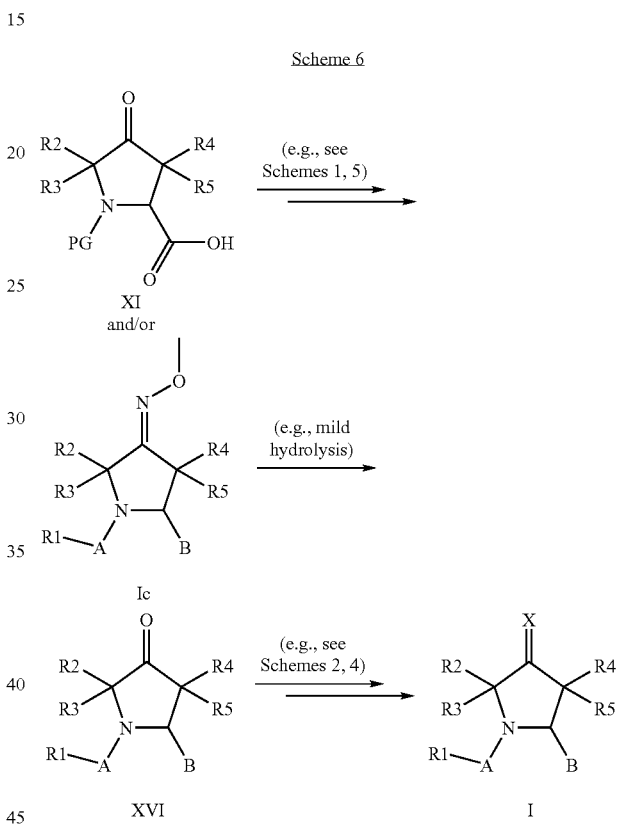

According to yet another process, pyrrolidine derivatives according to the general formula I, whereby the substituents A, B, X, and $R^1$ are as above defined, are prepared from the corresponding suitably N-protected 4-substituted pyrrolidine derivatives II, whereby the substituent X is above defined, by a solid-phase protocol such as described in the examples and shown in Scheme 7, below. The N-Boc-protected 4-substituted pyrrolidine derivative II is reacted e.g. with Kaiser oxime resin using standard carbodiimide-mediated coupling conditions well known to the practitioner skilled in the art, followed by Boc-deprotection with dilute TFA in DCM, or with $BF_3.OEt_2$ in dilute HOAc in DCM, to give compound XIX. The latter compound can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. DIC or EDC, to yield products of general formula XX.

Compounds of formula I wherein A is different from the carbonyl functionality are pre-pared by replacing formula VI with compounds containing the appropriate functional groups, e.g. sulfonyl chlorides, isocyanates, isothiocyanates, chloroformates, substituted allyl halides, or others to yield sulfonamide, urea, thiourea, carbamate, substituted alkyl derivatives, or others respectively.

In order to obtain the final compounds of general formula I, the linkage to the resin is cleaved by prolonged treatment with amines of general formulae III or XIII and low percentages of a weak acid, such as HOAc. The cycles within the below Scheme 7 illustrate the resign beads to which the corresponding compounds are linked during the solid phase synthesis. Other derivatives of formula I are prepared using known modifications to, or variations of, the Scheme 7 reaction sequence. Further to the above mentioned Kaiser oxime resin, other suitable reagents, notably resins, known to a person skilled in the art, could be employed for the solid-phase synthesis of compounds of general formula I.

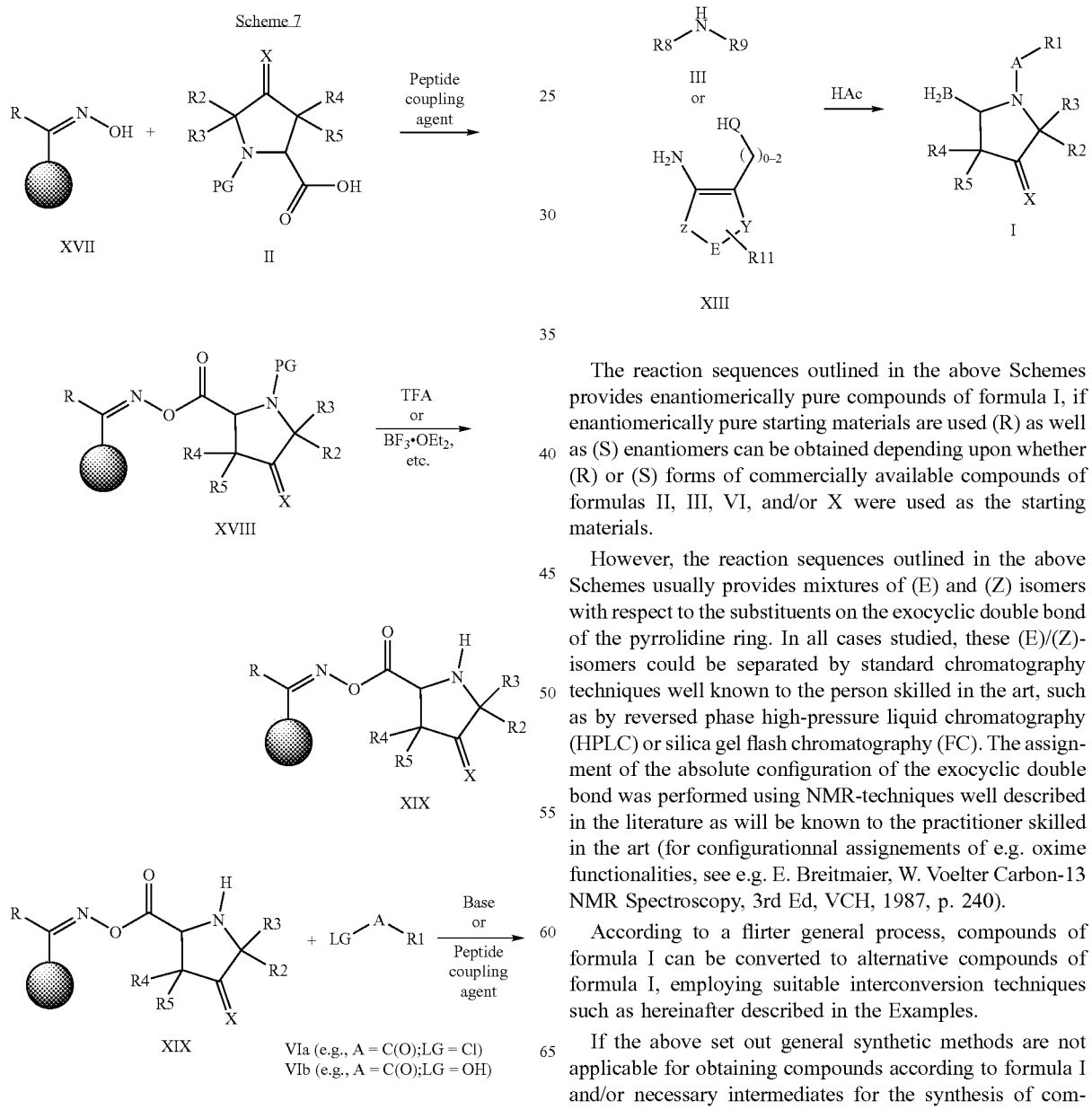

The reaction sequences outlined in the above Schemes provides enantiomerically pure compounds of formula I, if enantiomerically pure starting materials are used (R) as well as (S) enantiomers can be obtained depending upon whether (R) or (S) forms of commercially available compounds of formulas II, III, VI, and/or X were used as the starting materials.

However, the reaction sequences outlined in the above Schemes usually provides mixtures of (E) and (Z) isomers with respect to the substituents on the exocyclic double bond of the pyrrolidine ring. In all cases studied, these (E)/(Z)-isomers could be separated by standard chromatography techniques well known to the person skilled in the art, such as by reversed phase high-pressure liquid chromatography (HPLC) or silica gel flash chromatography (FC). The assignment of the absolute configuration of the exocyclic double bond was performed using NMR-techniques well described in the literature as will be known to the practitioner skilled in the art (for configurationnal assignements of e.g. oxime functionalities, see e.g. E. Breitmaier, W. Voelter Carbon-13 NMR Spectroscopy, 3rd Ed, VCH, 1987, p. 240).

According to a flirter general process, compounds of formula I can be converted to alternative compounds of formula I, employing suitable interconversion techniques such as hereinafter described in the Examples.

If the above set out general synthetic methods are not applicable for obtaining compounds according to formula I and/or necessary intermediates for the synthesis of compounds of formula I, suitable methods of preparation known by a person skilled on the art should be used. In general, the synthesis pathways for any individual compound of formula I will depend on the specific substitutents of each molecule and upon the ready availability of intermediates necessary; again such factors being appreciated by those of ordinary skill in the art. For all the protection, de-protection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

Compounds of this invention can be isolated in association with solvent molecules by crystallization from evaporation of an appropriate solvent. The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salt may be formed or interconverted using ion-exchange resin techniques.

If the above set out general synthetic methods are not applicable for the obtention of compounds of formula I, suitable methods of preparation known by a person skilled in the art should be used.

A final aspect of the present invention is related to the formulations containing the active compounds according to formula I. When employed as pharmaceuticals, the pyrrolidine derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharma-ceutical composition. Also, the present invention provides compounds for use as a medi-cament. In particular, the invention provides the compounds of formula I for use as Bax antagonist, for the treatment of disorders of mammals, notably of human beings associated with inappropriate cell death, including neurodegenerative disorders, diseases associated with polyglutamine tracts, epilepsy, ischemia, infertility, cardiovascular disorders, renal hypoxia, hepatitis and AIDS, either alone or in combination with other medicaments, notably in combination with further Bax inhibitors.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrrolidine compounds of formula I in such compositions is/are typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, $17^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharma-ceutical Sciences*.

In the following the present invention shall be illustrated by means of some examples which are not construed to be viewed as limiting the scope of the invention. The HPLC, NMR and MS data provided in the examples described below were obtained as followed. The following abbreviations are hereinafter used in the accompanying examples: min (minute), hr (hour), g (gram), mmol (millimole), m.p. (melting point), eq (equivalents), mL (milliliter), µL (microliters), mL (milliliters), ACN (Acetonitrile), CDCl$_3$ (deuterated chloroform), cHex (Cyclohexanes), DCM (Dichloromethane), DECP (Diethylcyanophosphonate), DIC (Diisopropyl carbodiimide), DMAP (4 Dimethylaminopyridine) DMF (Dimethylformamide), DMSO (Dimethylsulfoxide), DMSO-d$_6$ (deuterated dimethylsulfoxide), EDC (1-(3-Dimethylamino-propyl)-3-ethylcarbodiimide), EtOAc (Ethyl acetate), Et$_2$O (Diethyl ether), HOBt (1-Hydroxybenzotriazole), K$_2$CO$_3$ (potassium carbonate), NaH (Sodium hydride), NaHCO$_3$ (Sodium bicarbonate), nBuLi (n Butyllithium), TBTU (O-Benzotriazolyl-N,N,N',N'-tetramethyluronium-tetrafluoroborate), TEA (Triethyl amine), TFA (Trifluoro-acetic acid), THF (Tetrahydrofuran), MgSO$_4$ (Magnesium sulfate), PetEther (Petroleum ether), rt (room temperature).

EXAMPLES

Intermediate 1: (2S)-1-(tert-butoxycarbonyl)-4-oxo-2-pyrrolidinecarboxylic acid

Commercial (2S,4R)-1-(tert-butoxycarbonyl)-4-hydroxy-2-pyrrolidinecarboxylic acid (30 g, 0.13 mol) was dissolved in acetone (1500 ml). A mechanical stirrer was placed in the flask and the solution stirred vigorously. A freshly made solution of 8N chromic acid was prepared by dissolving chromium trioxide (66.7 g, 0.667 mol) in water (40 ml), adding concentrated sulphuric acid (53.3 ml) and adding enough water to bring the solution volume to 115 ml. The 8N chromic acid solution (115 ml) was then added dropwise over a period of 30 minutes with continued vigorous stirring, the reaction's exotherm being maintained at the optimal temperature of 25° C. by the use of an ice bath. After the complete addition of the chromic acid, the reac-tion mixture was stirred for a further 15 minutes—maintaining the optimal temperature of 25° C. The reaction mixture was then quenched by the addition of methanol (20 ml). Exotherm controlled by the use of an ice bath and, if necessary, direct addition of a small amount of crushed ice to the reaction mixture itself. The reaction mixture was filtered through a Celite pad and then concentrated in vacuo. The resulting acidic solution was then extracted with ethyl acetate (3×300 ml) and the combined organic layers washed with brine (2×100 ml). Organics then dried with magnesium sulfate and concentrated in vacuo. Crude product recrystallised from ethyl acetate to give the white crystalline product, (2S)-1-(tertbutoxycarbonyl)-4-oxo-2-pyrrolidinecarboxylic acid (22.55 g, 76%). The antipodal intermediate, (2R)-1-(tert-butoxycarbonyl)-4-oxo-2-pyrrolidinecarboxylic acid, was made according to the same protocol, starting from commercial (2R,4S)-1-(tert-butoxycarbonyl)-4-hydroxy-2-pyrrolidinecarboxylic acid.

1H NMR (360 MHz, CDCl3); 1.4 (m, 9H), 2.5–3.0 (m, 2H), 3.7–3.9 (m, 2H), 4.75 (dd, 1H)

Intermediate 2: 1-tert-butyl 2-methyl (2S)-4-oxo-1,2-pyrrolidinedicarboxylate

A solution of (2S)-1-(tert-butoxycarbonyl)-4-oxo-2-pyrrolidinecarboxylic acid (1 g, 4.3 mmol) in a 1:1 mixture of methanol and toluene (60 ml) was made. Trimethylsilyl diazomethane (6.5 ml of a 2M solution in hexanes, 13 mmol) was then added dropwise to the stirred solution at room temperature under nitrogen. After completion of the evolution of nitrogen gas, the resulting yellow solution was evaporated in vacuo, and the residue filtered through a pad of silica gel, eluting with ethyl acetate. Removal of solvent from the filtrate gave a yellow oil (1.05 g, near quantitative yield).

$^1$H NMR (400 MHz, CDCl$_3$); 1.4 (m, 9H), 2.5 (m, 1H), 2.8–2.9 (m, 1H) 3.7 (s, 3H), 3.9 (m, 2H), 4.6–4.8 (m, 1H).

Intermediate 3: 1-tert-butyl 2-methyl (2S,4EZ)-4-(chloromethylene)-1,2-pyrrolidinedicarboxylate Chloromethyltriphenylphosphonium iodide (270 mg, 0.62 mmol) was added to a solution of potassium tert-butoxide (67 mg, 0.59 mmol) in anhydrous diethyl ether (5 ml) under nitrogen and the resulting bright yellow mixture stirred for 30 minutes at ambient temperature. The reaction was then cooled to 0° C. and a solution of 1-tert-butyl 2-methyl (2S)-4-oxo-1,2-pyrrolidinedicarboxylate (100 mg, 0.41 mmol in 2 ml anhydrous diethyl ether) was added dropwise. The reaction was then warmed to room temperature and stirred for 30 minutes before adding saturated aqueous ammonium chloride solution (0.5 ml). The organic layer was removed in vacuo, and the aqueous washed with diethyl ether (3×5 ml). The combined organic layers were dried with brine and magnesium sulfate before filtering and removal of solvent. The desired product was isolated by silica gel chromatography, eluting with 15% ethyl acetate in hexanes to give 105 mg (93% yield) as a off-white wax.

$^1$H NMR (400 MHz, CDCl$_3$); 1.4 (9H, m), 2.6–2.75 (m, 1H), 2.8–3.0 (m, 1H), 3.65 (s, 3H), 4.1 (m, 2H), 4.4–4.5 (m, 1H) 5.9–6.0 (m, 1H).

Intermediate 4: 1-tert-butyl 2-methyl (2S)-4methylene-1,2-pyrrolidinedicarboxylate Methyltriphenylphosphonium bromide (22 g, 61.6 mmol) was added to a solution of potas-sium tert-butoxide (6.5 g, 57.6 mmol) in anhydrous diethyl ether (450 ml) at 0° C. under nitrogen and the resulting bright yellow mixture stirred for 30 minutes. A solution of 1-tert-butyl 2-methyl (2S)-4-oxo-1,2-pyrrolidinedicarboxylate (10 g, 41.1 mmol in 150 ml anhydrous diethyl ether) was added slowly to the reaction mixture, which was then warmed at 35° C. for 3 h. Saturated aqueous ammonium chloride solution (0.5 ml) was then added. The organic layer was removed, and the aqueous washed with diethyl ether (3×5 ml). The combined organic layers were dried with brine and magnesium sulfate before filtering and removal of solvent. Silica gel chromatography, eluting with 15% ethyl acetate in hexanes gave the desired pro-duct 6.9 g (70% yield) as a off-white wax.

$^1$H NMR (400 MHz, CDCl$_3$); 1.4 (9H, m), 2.5 (m, 1H), 2.8 (m, 1H), 3.65 (s, 3H), 4.0 (m, 2H), 4.3–4.5 (m, 1H), 4.9 (m, 2H).

Intermediate 5: 1-tert-butyl 2-methyl (2S,4EZ)-4-(cyanomethylene)-1,2-pyrrolidinedicarboxylate Diethyl cyanomethyl phosphonate (0.86 ml, 4.4 mmol) was dissolved in dry THF (50 ml) and the solution cooled to 0° C. Sodium hydride (205 mg of a 60% suspension in parrafin oil, 5.1 mmol) was then added cautiously and the reaction stirred for 30 min. The reaction mixture was then cooled to −78° C. and a solution of 1-tert-butyl 2-methyl (2S)-4oxo-1,2-pyrrolidinedicarboxylate (1.0 g, 4.1 mmol) in dry THF (5 ml) was added dropwise. The reaction was then allowed to reach room temperature. Saturated aqueous ammonium chloride solution (15 ml) was then added, followed by ethyl acetate (100 ml). (The organic layer was removed, and the aqueous washed with ethyl acetate (3×5 ml). The combined organic layers were dried with brine and magnesium sulfate before filtering and removal of solvent.

Silica gel chromatography, eluting with 35% ethyl acetate in hexanes gave the desired compound (860 mg, 80%) as an off-white wax.

$^1$H NMR (360 MHz, CDCl$_3$); 1.4 (m, 9H), 2.7–3.0 (m, 1H), 3.1–3.3 (m, 1H), 3.7 (m, 3H), 4.2–4.4 (m, 2H), 4.5–4.7 (m, 1H), 5.4 (m, 1H).

Intermediate 6: 1-tert-butyl 2-methyl (2S,4EZ)-4-benzylidene-1,2-pyrrolidinedicarboxylate Potassium tert-butoxide (6.1 g, 54 mmol) was added portionwise to a solution of benzyltriphenylphosphonium chloride (22.45 g, 58 mmol) in anhydrous dichloromethane (400 ml) and the reaction stirred at ambient temperature for 1 h. The solution was then cooled to 0° C. and a solution of 1-tert-butyl 2-methyl (2S)-4-oxo-1,2-pyrrolidinedicarboxylate (9.36 g, 38.5 mmol) in dry dichloromethane (30 ml) was added dropwise. After stirring for a further 1 h at 0° C. the reaction was stirred for a further 3 h at ambient temperature. Saturated aqueous ammonium chloride solution (30 ml) was then added. The organic layer was removed, and the aqueous washed with dichloromethane (3×20 ml). The combined organic layers were dried with brine and magnesium sulfate before filtering and removal of solvent. Silica gel chromatography, eluting with 30% ether in hexanes gave the desired product 8.65 g (71% yield) as a pale yellow wax.

$^1$H NMR (400 MHz, CDCl$_3$);1.5 (m, 9H), 2.8–3.0 (m, 1H), 3.2 (m, 1H), 3.7 (m, 3H), 4.2–4.4 (m, 2H), 4.5–4.6 (m, 1H), 6.3–6.4 (m, 1H), 7.1–7.5 (m, 5H).

Intermediate 7: (2S,4EZ)-1-(tert-butoxycarbonyl)-4-(methoxyimino)-2-pyrrolidinecarboxylic acid A solution was made containing (2S)-1-(tert-butoxycarbonyl)-4-oxo-2-pyrrolidinecarboxylic acid (5.0 g, 21 mmol) and O-methylhydroxylamine hydrochloride (2.7 g, 32.8 mmol) in chloroform (100 ml) containing triethyl-amine (5.5 g, 55 mmol). The reaction mixture was then stirred at ambient temperature over-night, prior to removal of solvent. The resultant crude reaction mixture was dissolved in ethyl acetate (150 ml) and washed rapidly with 1N HCl (40 ml). The acidic layer was then extracted with ethyl acetate (3×20 ml) and the combined organic layers washed with brine before drying over magnesiom sulfate, filtering and removal of solvent in vacuo. The desired product (5.3 g, 94%) was isolated as a pale yellow oil.

$^1$H NMR (400 MHz, CDCl$_3$); 1.45 (m, 91), 2.8–3.2 (m, 2H), 3.9 (s, 3H), 4.2 (m, 2H), 4.5–4.7 (m, 1H).

Intermediate 8: (2S,4EZ)-1-(tert-butoxycarbonyl)-4-(ethoxyimino)-2-pyrrolidinecarboxylic acid A solution was made containing (2S)-1-(tert-butoxycarbonyl)-4-oxo-2-pyrrolidinecarboxylic acid (5.0 g, 22mmol) and O-ethylhydroxylamine hydrochloride (6.4 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesiom sulfate, filtering and removal of solvent in vacuo. The desired product (5.5 g, 93%) was isolated as a pale yellow oil.

$^1$H NMR (400 MHz, DMSO); 1.3 (t, 3H), 1.55 (m, 9H), 2.9–2.7 (m, 1H), 3.4–3.1 (m, 1H), 4.1–4.3 (m, 4H), 4.6 (m, 1H), 12–13.5 (br, 1H).

Intermediate 9: (2S,4EZ)-4-[(allyloxy)imino]-1-(tert-butoxycarbonyl)-2-pyrrolidinecarboxylic acid A solution was made containing (2S)-1-(tert-butoxycarbonyl)-4-oxo-2-pyrrolidinecarboxylic acid (5.0 g, 22 mmol) and O-allylhydroxylamine hydrochloride monohydrate (7.2 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesium sulfate, filtering and removal of solvent in vacuo. The desired product (5.9 g, 94%) was isolated as a pale yellow oil.

$^1$H NMR (400 MHz, CDCl$_3$); 1.5 (m, 9H), 2.8–3.2 (m, 2H), 4.2 (m, 2H), 4.5–4.7 (m, 3H), 5.25 (m, 2H), 5.9 (m, 1H), 11.1 (broad S, 1H).

Intermediate 10: 1-[(aminooxy)methyl]-4-methoxybenzene

A solution was made of Boc hydroxylamine (2.0 g, 17.1 mmol) in dry THF (60 ml). Sodium hydride (1.1 g of a 60% suspension in paraffin oil, 25.7 mmol) was then added and the suspension stirred. A catalytic amount of KI was then added to the reaction prior to the cautious addition of 4-methoxybenzyl chloride (3.2 g, 20.4 mmol). The reaction was then allowed to stir overnight before removal of solvent in vacuo. The residue was taken up with diethyl ether (100 ml) and HCl gas bubbled in for 20 minutes, causing the start of precipitation of the product. The flask was stoppered and left to stand overnight. The product was then filtered off as a off-white wax (39–52% yield according to varying batches).

$^1$H NMR (400 MHz, D$_2$O); 3.8 (s, 3H), 5 (s, 2H), 7.0 (d, 2H), 7.4 (d, 2H).

Intermediate 11: (2S,4EZ)-1-(tert-butoxycarbonyl)-4-{[(4-methoxybenzyl)oxy]imino}-2-pyrrolidine-carboxylic acid The same method as employed in the preparation of Intermediate 7, but starting from (2S)-1-(tert-butoxycarbonyl)-4-oxo-2-pyrrolidinecarboxylic acid (Intermediate 1) and 1-[(aminooxy)methyl]-4-methoxy-benzene (Intermediate 10) gave the title compound as a gum in a 85% yield.

$^1$H NMR (400 MHz, DMSO); 1.5 (m, 9H), 2.7–2.9 (m, 1H) 3.9 (s, 3H), 4.2 (m, 3H), 4.6 (m, 1H), 5.15 (s, 2H), 7.1 (d, 2H), 7.45 (d, 2H).

Intermediate 12: 2-aminoethyl acetate, TFA-salt

A solution was made containing ethanolamine (36.5 ml, 0.6 mol) in chloroform (1000 ml). The Boc$_2$O (13.1 g, 60 mmol) dissolved in chloroform (600 ml) was slowly added dropwise at 0° C. over a 6-hours period (the temperature was maintained all over this period). The reaction was allowed to reach room temperature and was stirred overnight. The organic layer was washed with water (2×500 ml), brine and dried over magnesium sulfate before being concentrated in vacuo. The desired product (9.5 g, >95%) was isolated as a colourless oil and was used without further purification. A solution was made containing the Boc-ethanolamine (1.92 g, 12 mmol) with potassium carbonate (5 g, 36 mmol) in DCM (40 ml). Acetyl chloride (30 ml, 0.42 mol) was added and the reaction stirred for 6 hours at room temperature. The excess of acetyl chloride was removed in vacuo and the crude dissolved in DCM(100 ml). The organic layer was washed with water (50 ml), brine and dried over magnesium sulfate before being concentrated in vacuo. The desired product (1.86 g, 77%) was isolated as a colourless oil and was used without further purification. A solution was made containing the O-acyl, Boc-ethanolamine (1.65 g, 8.1 mmol) in DCM (20 ml) and TFA (20 ml) was added. After one hour at room temperature, the solvent was removed in vacuo. The crude was concentrated from methanol (2–3 times) and from DCM (2–3 times) to give the expected compound (1.75 g, quant.) as an oil used without further purification.

$^1$H NMR (400 MHz, D$_2$O); 2.0 (m, 9H), 3.1–3.2 (m, 2H), 4.15–4.25 (m, 2H).

Intermediate 13: 2'-methyl[1,1'-biphenyl]-4-carboxylic acid

To a mixture of 4-bromobenzoic acid (30 g, 0.15 mol), 2-methylphenylboronic acid (24 g, 0.15 mol), sodium carbonate (250 g) in toluene (500 mL) and water (500 mL) was added tetrakistriphenylphosphine palladium(0) (9 g, 0.0074 mol) under nitrogen atmosphere. The reaction mixture was refluxed for 10 h. After this time, 100 ml of 10% NaOH were added to the reaction mixture, the aqueous layer was separated and washed with toluene (2×200 mL). Acidification of the aqueous layer with 3N HCl solution gave a solid product, which was filtered, washed with water and dried. The crude product was then crystallised from toluene to yield 2'-methyl [1,1'-biphenyl]-4-carboxylic acid (20 g, 62.5%). Conversely, the product could also be obtained from 1-bromo-2-methylbenzene and 4-carboxybenzeneboronic acid, using analogous conditions.

$^1$H NMR (300 MHz, DMSO); 2.2 (s, 3H), 7.2–7.4 (m, 4H), 7.43 (d, J=9 Hz, 2H), 7.99 (d, J=9 Hz, 2H), 13 (b, 1H).

(In Red: No CAS-number)

Similarly, using the appropriate commercial boronic acids and arylbromides, the following, related intermediates were obtained: 4'-methyl[1,1'-biphenyl]-4-carboxylic acid; 2',3-dimethyl[1,1'-biphenyl]-4-carboxylic acid; 2',6'-dimethyl[1, 1'-biphenyl]-4-carboxylic acid; 2-methyl[1,1'-biphenyl]-4-carboxylic acid; 3-methyl[1,1'-biphenyl]-4-carboxylic acid; 2,2'-dimethyl[1,1'-biphenyl]4-carboxylic acid; 2'-methoxy [1,1'-biphenyl]-4-carboxylic acid; 3'-methoxy[1,1'-biphenyl]-4-carboxylic acid; 4'-methoxy[1,1'-biphenyl]-4-carboxylic acid; 2'-chloro[1,1'-biphenyl]-4-carboxylic acid; 3'-chloro[1,1'-biphenyl]-4-carboxylic acid; 4-chloro[1,1'-biphenyl]-4-carboxylic acid; 3',4'-dichloro[1,1'-biphenyl]-4-carboxylic acid; 2' -(trifluoromethyl)[1,1'-biphenyl]-4-carboxylic acid; 3'-(trifluoromethyl)[1,1'-biphenyl]-4-carboxylic acid; 2'-cyano[1,1'-biphenyl]-4-carboxylic acid; 2',4'-difluoro[1,1'-biphenyl]-4-carboxylic acid; 4-(2-pyridinyl)benzoic acid; 4-(3-pyridinyl)benzoic acid; 4-(4-pyridinyl)benzoic acid; 4-(5-pyrimidinyl)benzoic acid; and others.

Intermediate 14: 4-(3-methyl-2-pyridinyl)benzoic acid

A mixture of 2-bromo-3-methylpyridine (22.5 g, 0.1312 mol), 4-(hydroxymethyl)phenylboronic acid (25 g, 0.164 mol), Pd(PPh$_3$)$_4$ (9.5 g, 0.0082 mol), and sodium carbonate (200 g in 500 ml of water) in toluene (750 ml) were refluxed under nitrogen atmosphere for 15 h. Separated the toluene layer and distilled under reduced pressure to give a residue. The residue was then purified by column chromatography to yield [4-(3-methyl-2-pyridinyl)phenyl]methanol (12 g, 47%).

To a solution of [4-(3-methyl-2-pyridinyl)phenyl]methanol (12 g, 0.06 mol) in dry DMF (150 mL) was added pyridiniumdichromate (91 g, 0.24 mol) and stirred at RT for 3days. The reaction mixture was poured into water and extracted with ethyl acetate (250 mL). The organic layer was washed with water, brine, dried and concentrated. The crude was purified by column chromatography over silica gel to give 4-(3-methyl-2-pyridinyl)benzoic acid (3 g, 25%) as white solid.

$^1$H NMR (300 MHz, DMSO); 2.3 (s, 3H), 7.33 (dd, J=7.5 Hz, 5 Hz, 1H), 7.67 (d, J=8 Hz, 2H), 7.75 (d, J=7.5 Hz, 1H), 8.01 (d, J=8 Hz, 2H), 8.50 (d, J=5 Hz, 1H), 13 (b, 1H).

Intermediate 15: 4-(1-oxido-3-pyridinyl)benzoic acid

To a mixture of 4-tolylboronic acid (38 g, 0.28 mol), 3-bromopyridine (44 g, 0.28 mol), Na$_2$CO$_3$ (200 g) in toluene (500 ml) and water (500 ml) was added Pd(PPh$_3$)$_4$ (16 g, 0.014 mol), and refluxed for 16 h. The reaction mixture was cooled, and the separated organic layer was washed with water and brine, and dried. The solvent was removed to give 4-(3-pyridyl)toluene (42 g, 90%). To a mixture of 4-(3-pyridyl)toluene (35 g, 0.207 mol) in pyridine (400 ml) and water (400 ml) was added KMnO$_4$ (163 g, 1.03 mol) in portions and refluxed for 12 h. The reaction mixture was filtered through celite and acidified with conc. HCl. The product was washed with water and dried to give 4-(3-pyridyl)benzoic acid (32 g, 76%) as a white solid. To a mixture of 4-(3-pyridyl)benzoic acid (22 g, 0.11 mol) in THF (2.51), mCPBA (152 g, 0.44 mol, 50%) was added and stirred at RT for 12 h. The solid was filtered, and washed with THF to give 4-(1-oxido-3-pyridinyl)benzoic acid (20 g, 86%).

$^1$H NMR (300 MHz, DMSO); 7.5–7.8 (m, 5H), 7.9 (d, J=8Hz, 2H), 8.33 (d, J=5Hz, 2H.

Similarly, starting from 4-tolylboronic acid (45 g, 0.33 mol) and 2-bromopyridine (52 g, 0.33 mol), the related intermediate 4-(1-oxido-2-pyridinyl)benzoic acid was obtained.

Example 1

General Procedure for the Saponification of the Olefin-type Proline Methyl Esters, Such as Intermediates 3–6

A solution of sodium hydroxide (4.5 g, 112 mmol) in water (70 ml) was added to the relevant proline olefin methyl ester (66 mmol) in 3:1 dioxane:water (500 ml) and the reaction stirred for 3 h. The reaction mixture was then washed with diethyl ether (2×50 ml), and the aqueous phase acidified to pH 2 (0.1N HCl) and extracted into ethyl acetate. The ethyl acetate layer was then dried over magnesium sulfate, filtered and the solvent was then removed in vacuo to give the desired product in near quantitative yields as an oil which was used without further purification.

Example 2

General Protocol for the Solution-phase Synthesis of Oximether Pyrrolidine Derivatives of General Formula Ia (Scheme 1)

Method A: e.g. (2S,4EZ)-1-([1,1'-biphenyl]-4-ylcarbonyl)-N-(2-methoxyethyl)-4-(methoxyimino)-2-pyrrolidinecarboxamide a) Protocol for the Formation of the Amide Bond A solution was made containing the central building block, e.g. (2S,4EZ)-1-(tert-butoxycarbonyl)-4-(methoxyimino)-2-pyrrolidinecarboxylic acid (Intermediate 7) (1.5 g, 5.8 mmol), an amine or an amine salt, e.g. 2-methoxyethylamine (0.51 ml, 5.81 mmol) and DMAP (780 mg, 5.8 mmol) in DCM (30 ml). At 0° C., EDC (1.1 g, 5.8 mmol) was slowly added portion-wise. The reaction was slowly allowed to reach room temperature and was stirred overnight. The DCM was evaporated and the crude purified by column chromatography using EtOAc (100%) to collect the desired product, e.g. tert-butyl (2S,4EZ)-2-{[(2-meth-oxyethyl)amino]carbonyl}-4-(methoxyimino)-1-pyrrolidinecarboxylate (1.5 g, 80%) as a colourless oil.

¹H NMR (400 MHz, CDCl₃); 1.25 (m, 9H), 2.5–2.9 (m, 2H), 3.1 (s, 3H), 3.2–3.3 (m, 4H), 3.65 (s, 3H), 3.8–4.4 (m, 3H), 6.7 (s broad, 1H).

b) Protocol for the N-deprotection Step

A solution was made containing the amide compounds from the previous step, e.g. tert-butyl (2S,4EZ)-2-{[(2-methoxyethyl)amino]carbonyl}-4-(methoxyimino)-1-pyrrolidine-carboxylate (1.5 g, 0.4 mmol), in anhydrous ether (35 ml). HCl gas was bubbled slowly through the reaction and the deprotection was followed by TLC. After approximately 20 minutes, the ether was evaporated. The product was concentrated in vacuo from DCM (2–3 times) to remove the HCl. The desired product, e.g. (2S,4EZ)-N-(2-methoxyethyl)-4-(methoxyimino)-2-pyrrolidinecarboxamide (1.2 g, quant.) was isolated as a yellow oil and used without further purification.

c) Protocol for the N-capping Step

A solution was made containing the free NH-compound from the previous step, e.g. (2S,4EZ)-N-(2-methoxyethyl)-4-(methoxyimino)-2-pyrrolidinecarboxamide (940 mg, 3.7 mmol), a carboxylic acid, e.g. [1,1'-biphenyl]-4-carboxylic acid (740 mg, 3.7 mmol) and DMAP (960 mg, 7.8 mmol) in DCM (30 ml). At 0° C., EDC (715 mg, 3.7 mmol) was slowly added portionwise. The reaction was slowly allowed to reach room temperature and was stirred overnight. The DCM was evaporated and the crude purified by column chromato-graphy using EtOAc (100%) to collect the desired product, e.g. (2S,4EZ)-1-([1,1'-biphe-nyl]-4-ylcarbonyl)-N-(2-methoxyethyl)-4-(methoxyimino)-2-pyrrolidinecarboxamide as a mixture of two isomers as an off-white solid.

1H NMR (400 MHz, CDCl3); 2.75–2.85 (m, 1H), 3.1–3.3 (m, 4H), 3.4–3.5 (m, 4H), 3.8 (m, 3H), 4.1–4.3 (m, 2H), 5.1 (m, 1H), 6.9 (m, 1H), 7.2–7.7 (m, 10H). M⁺ (APCI⁺); 396.

Method B: e.g. (2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide a) Protocol for the Formation of the Amide Bond To a solution of the central building block, e.g. (2S,4EZ)-1-(tert-butoxycarbonyl)-4-(methoxyimino)-2-pyrrolidin-ecarboxylic acid (Intermediate 7) (24.2 mmol, 6.24 g) in dry THF (125 ml) at −25° C. was added NMM (2.5 eq, 60.4 mmol, 6.64 ml) followed by isobutylchloroformate (1.05 eq, 25.4 mmol, 3.3 ml). The resulting mixture was stirred at −25° C. for 30 min and an amine or an amine salt, e.g. (S)-2-amino-1-phenylethanol (1.51 eq, 36.5 mmol, 5 g) was then added. The mixture was allowed to gradually warm to rt. After 16 h, the solvents were removed. The residue was dissolved in AcOEt, washed twice with NH₄Cl saturated solution, then twice with 10% NaHCO₃ solution. The organic layer was dried over Na₂SO₄, filtrated and concentrated to afford the desired product, e.g. tert-butyl (2S,4EZ)-2-({[(2S)-2-hydroxy-2-phenylethyl]amino}carbonyl)-4-(methoxyimino)-1-pyrrolidinecarboxylate (8.76 g, 96%) as a pale yellow oil in 88.5% purity by HPLC.

¹H NMR (CDCl₃: 300 MHz) δ 1.44 (s, 9H, N-Boc), 3.23–2.85 (m, 4H), 3.72 (m, 1H), 3.85 (s, 3H, O—CH₃), 4.10 (m, 2H), 4.49 (m, 1H), 4.83 (m, 1H), 7.34 (m, 5H, Ar—H); [M+Na⁺] (ESI⁺): 400.

b) Protocol for the N-deprotection Step

A solution was made containing the amide compounds from the previous step, e.g. tert-butyl (2S,4EZ)-2-({[(2S)-2-hydroxy-2-phenylethyl]amino}carbonyl)-4-(methoxyimino)-1-pyrrolidinecarboxylate (2.64 g, 7 mmol), in anhydrous DCM (35 ml). At 0° C., HCl gas was bubbled slowly through the reaction and the deprotection was followed by TLC. After approximately 20 minutes, the DCM was evaporated. The product was concentrated in vacuo from DCM (2–3 times) to remove the HCl. The desired product, e.g. (2S,4EZ)-N-[(2S)-2 -hydroxy-2-phenylethyl]-4-(methoxyimino)-2-pyrrolidinecarboxamide (1.94 g, quant.) was isolated as a yellow solid and used without further purification.

c) Protocol for the N-capping Step

To a suspension of 4-(2-methylphenyl)benzoic acid (1.49 g, 7 mmol.) in 35 ml DCM, was added oxalyl chloride and DMF (3 ml) under ice cooling. The mixture was stirred for 2 h at rt. The solvent was removed affording the corresponding acyl chloride as a yellow solid. It was dissolved in DCM (30 mL) and added slowly on a 0° C. solution containing the free NH-compound from the previous step, e.g. (2S,4EZ)-N-[(2S)-2-hydroxy-2-phenylethyl]-4-(methoxyimino)-2-pyrrolidinecarboxamide (1.94 g, 7 mmol), and triethylamine (5 eq, 35 mmol, 4.9 ml) in dry DCM (35 ml). The reaction mixture was stirred overnight at r.t. Poltrisamine was added (2.12 g, 3.45 mmol/g) in order to scavenge excess of acyl chloride. The mixture was shaken 3 h, filtered and the resulting solution was washed with NH₄Cl sat, brine, and dried over Na₂SO₄. After filtration and evaporation of the solvents, the resulting dark oil (3.26 g) was purified by flash chromatography (Biotage system, column 40M, 90 g SiO2, with gradients of DCM and MeOH as eluent), affording (2S,4EZ)-N-[(2S)-2-hydroxy-2-phenylethyl]-4-(methoxyimino)-1-[(2'-methyl[1,1'-biphenyl]-4-yl)carbonyl]-2-pyrrolidinecarboxamide. Separation of the E/Z-isomers was achieved by several chromatographies, affording (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (230 mg, colorless powder, 98.7% purity by HPLC) and (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (266 mg, colorless powder, 98.3% purity by HPLC).

(2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide: Map. 74° C.; IR (neat) ν 3318, 2932, 1613, 1538, 1416, 1239, 1047, 848 cm⁻¹; ¹H NMR (300 MHz, CDCl₃): 2.27 (s, 3H, ArCH₃), 2.89 (dd, J=6, 12 Hz, 1H), 3.18 (br d, J=12 Hz, 1H), 3.27 (m, 1H), 3.76 (m, 1H), 3.88 (s, 3H, NOCH₃), 4.28 (d, J=10 Hz, 1H), 4.47 (d, J=10 Hz, 1H), 4.59 (br s, 1H), 4.88 (m, 1H), 5.20 (m, 1H), 7.03–7.42 (m, 11H, H arom.), 7.45–7.54 (m, 2H, H arom.); M⁺(APCI⁺): 472; M⁻(APCI⁻): 470. Analysis calculated for C₂₈H₂₉N₃O₄ 0.3 H₂O: C, 70.51; H, 6.26; N, 8.81. Found: C, 70.53; H, 6.30; N, 8.87.

(2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide: M.p. 78° C.; IR (neat) ν 3318, 2938, 1622, 1538, 1416, 1233, 1045, 852 cm⁻¹; ¹H NMR (300 MHz, CDCl₃): 2.28 (s, 3H, ArCH₃), 2.69 (dd, J=6, 10 Hz, 1H), 3.02–3.22 (m, 2H), 3.25 (br s, 1H), 3.60 (m, 1H), 3.86 (s, 3H, NOCH₃), 4.14 (m, 2H), 4.71 (m, 1H), 4.96 (m, 1H), 7.03–7.42 (m, 11H, H arom.), 7.45–7.54 (m, 2H, H arom.); M⁺(APCI⁺): 472; M⁻(APCI⁻): 470. Analysis calculated for C₂₈H₂₉N₃O₄ 0.9 H₂O: C, 68.95; H, 6.36; N, 8.61. Found: C, 68.87; H, 6.25; N, 8.77.

d) E/Z-isomerisation

The pure E-isomer was isomerized to a mixture of the E/Z-isomers by the following procedure: the E-isomer was dissolved in dioxane/water 3:1 mixture. NaOH (1.7 eq; 0.52 mL of NaOH 1.6N) was added and the resulting solution was stirred 2 h at r.t. The mixture was neutralysed with HCl 0.1

N and lyophilised. The components of the resulting E/Z-mixture were separated and purified by flash chromatography using same conditions as described above.

Example 3

(2S,4EZ)-1-([1,1'-biphenyl]-4-ylcarbonyl)-N-[2-(diethylamino)ethyl]-4-{[(4-methoxybenzyl)oxy]imino}-2-pyrrolidinecarboxamide Following the general method as outlined in Example 2, starting from (2S,4EZ)-1-(tert-butoxycarbonyl)-4-{[(4-methoxybenzyl)oxy]imino}-2-pyrrolidinecarboxylic acid, [1,1'-biphenyl]-4carboxylic acid, and $N^1,N^1$-diethyl-1,2-ethanediamine the title compound was obtained after column chromatography as an off-white solid as a mixture of E/Z-isomers.

1H NMR (400 MHz, CDCl3); 1.05–1.15 (m, 6H), 2.7–2.8 (m, 1H), 2.9–3.2 (m, 6H), 3.4 (m, 1H), 3.6 (s, 3H), 4.0–4.1 (m, 1H), 4.3–4.4 (m, 1H), 3.75 (m, 1H), 3.8 (m, 2H), 6.65 (m, 2H), 7.0–7.1 (m, 2H), 7.2–7.3 (m, 3H), 7.35–7.45 (m, 6H), 8.8 (s/br, 0.5H). M$^+$(APCI$^+$); 543.

Example 4

(2S,4EZ)-1-([1,1'-biphenyl]-4-ylcarbonyl)-4-(chloromethylene)-N-[(2RS)-2-hydroxy-2-phenethyl]-2-pyrrolidinecarboxamide Following the general method as outlined in Example 2, starting from (2S,4EZ)-1-(tert-butoxycarbonyl)-4-(chloromethylene)-2-pyrrolidinecarboxylic acid, [1,1'-biphenyl]-4-carboxylic acid, and (1RS)-2-amino-1-phenylethanol, the title compound was obtained after column chromatography as a mixture of E/Z-isomers as a off-white solid. The two isomers could be separated by another flash chromatographic purification step.

(2S,4E)-1-([1,1'-biphenyl]-4-ylcarbonyl)-4-(chloromethylene)-N-[(2RS)-2-hydroxy-2-phenethyl]-2-pyrrolidinecarboxamide: 1H NMR (400 MHz, CDCl3); 2.6–2.7 (m, 1H), 2.8–3.0 (m, 3H), 3.2 (m, 1H), 3.4–3.6 (m, 1H), 3.9 (m, 1H), 4.15 (t, 1H), 4.6 (m, 1H), 4.85 (m, 1H), 5.75 (s, 1H), 7.0–7.4 (m, 14H). M$^+$(APCI$^+$); 461.

(2S,4Z)-1-([1,1'-biphenyl]-4-ylcarbonyl)-4-(chloromethylene)-N-[(2RS)-2-hydroxy-2-phenethyl]-2-pyrrolidinecarboxamide: 1H NMR (400 MHz, CDCl3); 2.5–2.6 (m, 1H), 2.7–2.9 (m, 1H), 3.0 (m, 1H), 3.1–3.4 (m, 1H), 3.4–3.6 (m, 1H), 3.9–4.0 (m, 1H), 4.2–4.4 (m, 2H), 4.6 (m, 1H), 4.8–4.9 (m, 1H), 5.75 (s, 1H), 7.0–7.5 (m, 14H). M$^+$(APCI$^+$); 461.

Example 5

(2S,4EZ)-N-[2-(diethylamino)ethyl]-1-(diphenylacetyl-4-(methoxyimino)-2-pyrrolidinecarboxamide Following the general method as outlined in Example 2, starting from (2S,4EZ)-1-(tert-butoxycarbonyl)-4-(methoxyimino)-2-pyrrolidinecarboxylic acid, diphenylacetic acid, and $N^1,N^1$-diethyl-1,2-ethanediamine the title compound was obtained after column chromatography as an off-white solid as a mixture of E/Z-isomers.

1H NMR (400 MHz, CDCl3); 0.9 (t, 3H), 1.0 (m, 3H), 2.6–3.1 (m, 7H), 3.15 (m, 1H), 3.4 (m, 1H), 3.75 (s, 3H), 3.95 (t, 1H), 4.4–4.7 (m, 4H), 5.1 (m, 1H), 7.0–7.3 (m, 10H), 9.1 (m, 1H). M$^+$(APCI$^+$); 451.

Example 6

(2S,4EZ)-4-(ethoxyimino)-N-(9-ethyl-9H-carbazol-3-yl)-1-(phenoxyacetyl)-2-pyrrolidinecarboxamide Following the general method as outlined in Example 2, starting from (2S,4EZ)-1-(tert-butoxycarbonyl)-4-(ethoxyimino)-2-pyrrolidinecarboxylic acid, phenoxyacetic acid, and 9-ethyl-9H-carbazol-3-amine the title compound was obtained after column chromatography as an off-white solid as a mixture of E/Z-isomers. The isomers were then separated using column chromatography.

(2S,4E)-4-(ethoxyimino)-N-(9-ethyl-9H-carbazol-3-yl)-1-(phenoxyacetyl)-2-pyrrolidinecarboxamide: 1H NMR (360MHz, CDCl$_3$); 1.2 (m, 6H), 2.7 (m, 1H), 3.35 (d, 1H), 4.1 (m, 4H), 4.3 (d, 1H), 4.45 (d, 1H), 4.7 (m, 2H), 5.15 (d, 1H), 6.9–7.3 (m, 10H), 7.9 (d, 1H), 8.15 (m, 1H), 9.0 (br s, 1H). M$^+$(APCI$^+$); 499.

(2S,4Z)-4-(ethoxyimino)-N-(9-ethyl-9H-carbazol-3-yl)-1-(phenoxyacetyl)-2-pyrrolidinecarboxamide: 1H NMR (360MHz, CDCl$_3$); 1.2 (m, 6H), 2.7 (m, 1H), 3.2 (m, 1H), 4.1 (m, 4H), 4.35 (m, 2H), 4.7 (m, 2H), 5.1 (m, 1H), 6.9–7.3 (m, 10H), 7.9 (d, 1H), 8.15 (m, 1H), 9.0 (br s, 1H). M$^+$(APCI$^+$); 499.

Example 7

(2S,4EZ)-N-(9-ethyl-9H-carbazol-3-yl)-4-(methoxyimino)-1-[(2-oxo-6-pentyl-2H-pyran-3-yl)carbonyl]-2-pyrrolidinecarboxamide Following the general method as outlined in Example 2, starting from (2S,4EZ)-1-(tert-butoxycarbonyl)-4-(methoxyimino)-2-pyrrolidinecarboxylic acid, 2-oxo-6-pentyl-2H-pyran-3-carboxylic acid, and 9-ethyl-9H-carbazol-3-amine the title compound was obtained after column chromatography as an off-white solid as a mixture of E/Z-isomers. The isomers were separated by column chromatography.

(2S,4E)-N-(9-ethyl-9H-carbazol-3-yl)-4-(methoxyimino)-1-[(2-oxo-6-pentyl-2H-pyran-3-yl)carbonyl]-2-pyrrolidinecarboxamide: 1H NMR (360MHz, CDCl$_3$); 0.8 (m, 6H), 1.2 (m. 6H), 2.5 (m, 2H), 3.0 (m, 1H), 3.3 (m, 1H), 3.8 (s, 3H), 4.2 (m, 3H), 4.45 (m, 1H), 5.3 (m, 1H), 6.1 (d, 1H), 7.1 (m, 1H), 7.2 (m, 1H), 7.3 (d, 1H), 7.35 (m, 1H), 7.55 (m, 1H), 7.65 (m, 1H), 8.0 (d, 1H), 8.5 (m, 1H), 9.1 (br S, 1H). M$^+$(ES$^+$); 543.

(2S,4Z)-N-(9-ethyl-9H-carbazol-3-yl)-4-(methoxyimino)-1-[(2-oxo-6-pentyl-2H-pyran-3-yl)carbonyl]-2-pyrrolidinecarboxamide: 1H NMR (360MHz, CDCl$_3$); 0.8 (m, 6H), 1.2 (m. 6H), 2.5 (m, 2H), 3.05 (m, 1H), 3.25 (m, 1H), 3.75 (s, 3H), 4.1 (m, 3H), 4.45 (d, 1H), 5.3 (d, 1H, 6.1 (d, 1H), 7.1 (t, 1H), 7.2 (m, 1H), 7.3 (m, 1H), 7.4 (m, 1H), 7.6 (m, 1H), 7.7 (m, 1H), 8.0 (d, 1H), 8.45 (m, 1H), 9.1 (m, 1H). M$^+$(ES$^+$); 543.

Example 8

(2S,4EZ)-4-[(allyloxy)imino]-1-benzoyl-N-(9-ethyl-9H-carbazol-3-yl)-2-pyrrolidinecarboxamide Following the general method as outlined in Example 2, starting from (2S,4EZ)-4-[(allyloxy)imino]-1-(tert-butoxycarbonyl)-2-pyrrolidinecarboxylic acid, benzoic acid, and 9-ethyl-9H-carbazol-3-amine the title compound was obtained after column chromatography as an off-white solid as a mixture of E/Z-isomers.

1H NMR (360MHz, CDCl₃); 1.2 (m, 3H), 2.8 (m, 1H), 3.35 (m, 1H), 4.2 (m, 4H), 4.4 (m, 3H), 5.2 (m, 2H), 5.35 (m, 1H), 5.85 (m, 1H), 7.0–7.5 (m, 5H), 7.9 (m, 3H), 8.1 (m, 2H), 8.3 (m, 1H), 9.2 (br s, 1H). M⁺(APCI⁺); 481.

Example 9

General Protocol for the Solution-phase Synthesis of Oximether Pyrrolidine Derivatives of General Formula I Containing Additional Reactive Groups; (2S,4EZ)-1-([1,1'-biphenyl]-4-ylcarbonyl)-N-(2-hydroxyethyl)-4-(methoxyimino)-2-pyrrolidinecarboxamide a) Protocol for the Formation of the Amide Bond A solution was made containing the central building block, e.g. (2S,4EZ)-1-(tert-butoxycarbonyl)-4-(methoxyimino)-2-pyrrolidinecarboxylic acid (Intermediate 7) (575 mg, 2.2 mmol), the amine or amine salt containing the suitably protected reactive group, e.g. 2-aminoethyl acetate (Intermediate 12) (480 mg, 2.2 mmol) and DMAP (870 mg, 7.1 mmol) in DCM (20 ml). At 0° C., EDC (427 mg, 2.2 mmol) was slowly added portion-wise. The reaction was slowly allowed to reach room temperature and was stirred overnight. The DCM was evaporated and the crude purified by column chromatography using EtOAc/Hexane: 55/45 to collect the desired amide compound, e.g. tert-butyl (2S,4EZ)-2-({[2-(acetyloxy)ethyl]-amino}carbonyl)-4-(methoxyimino)-1-pyrrolidinecarboxylate (373 mg, 49%) as an oil.

1H NMR (400MHz, CDCl3); 1.7 (m, 9H), 2.1–2.2 (m, 3H), 2.8–3.3 (m, 2H), 3.7–3.8 (m, 2H), 4.0–4.1 (m, 3H), 4.2–4.8 (m, 5H), 7.3 (s broad, 1H).

b) Protocol for the N-deprotection Step

A solution was made containing the Boc-protected compound from the previous step, e.g. tert-butyl (2S,4EZ)-2-({[2-(acetyloxy)ethyl]amino}carbonyl)-4-(methoxyimino)-1-pyrrolidinecarboxylate (373 mg, 1.2 mmol) in anhydrous ether (40 ml). HCl gas was bubbled slowly through the reaction and the deprotection was followed by TLC. After approximately 20 minutes, the ether was evaporated. The product was concentrated in vacuo from DCM (2–3 times) to remove the HCl. The desired free NH product, e.g. 2-({[(2S,4EZ)-4-(methoxyimino)pyrrolidinyl]carbonyl}amino)ethyl acetate (300 mg, quant.) was isolated as a yellow oil and used without further purification.

1H NMR (400MHz, D₂O); 1.75 (s, 3H), 2.55–2.65 (m, 1H), 2.8–3.3 (m, 3H), 3.45–3.55 (m, 3H), 3.8–4.0 (m, 4H), 4.25–4.35 (m, 1H).

c) Protocol for the N-capping Step

A solution was made containing the amine-hydrochloride from the previous step, e.g. 2-({[(2S,4EZ)-4-(methoxyimino)pyrrolidinyl]carbonyl}amino)ethyl acetate (560 mg, 2 mmol) and an acid chloride, e.g. [1,1'-biphenyl]-4-carbonyl chloride (433 mg, 2 mmol) in DCM (20 ml). Triethylamine (0.7 ml, 5 mmol) was added and the reaction stirred overnight at room temperature. The DCM was evaporated and the crude purified by column chromatography using EtOAc (100%) to collect the desired amide compound, e.g. 2-({[(2S,4EZ)-1-([1,1'-biphenyl]-4-ylcarbonyl)-4-(methoxyimino)pyrrolidinyl]carbonyl}amino)ethyl acetate (457 mg, 54%) as an oil.

1H NMR (400MHz, CDCl3); 1.9 (s, 3H), 2.7–2.8 (m, 1H), 3.2–3.6 (m, 3H), 3.75–3.85 (m, 3H), 4.0–4.4 (m, 4H), 5.15–5.25 (m, 1H), 7.2–7.6 (m, 9H).

d) Protocol for the Deprotection of the Reactive Group

A solution was made containing the side-chain protected compound from the previous step, e.g. 2-({[(2S,4EZ)-1-([1,1'-biphenyl]-4-ylcarbonyl)-4-(methoxyimino)pyrrolidinyl]carbonyl}amino)ethyl acetate (450 mg, 10.6 mmol) in THF (10 ml). An aqueous solution (10 ml) of sodium hydroxide (75 mg, 19 mmol) with methanol (5 ml) was added and the reaction stirred at room temperature for three hours. The solvent was removed in vacuo and the crude purified by column chromatography using THF (100%) to give the expected final product, e.g. (2S,4EZ)-1-([1,1'-biphenyl]-4-ylcarbonyl)-N-(2-hydroxyethyl)-4-(methoxyimino)-2-pyrrolidinecarboxamide (300 mg, 75%) as a white solid.

1H NMR (400MHz, CDCl3); 2.85–3.0 (m, 1H), 3.3–3.6 (m, 3H), 3.7–3.8 (2H), 3.85–3.95 (m, 3H), 4.2–4.5 (m, 2H), 5.15–5.25 (m, 1H), 7.2–7.9 (m, 9H). M⁺(APCI⁺); 382.

Example 10

(2S,4EZ)-1-([1,1'-biphenyl]-4-ylcarbonyl)-N-[(2RS)-2-hydroxy-2-phenethyl]-4-(methoxyimino)-2-pyrrolidinecarboxamide Following the general method as outlined in Example 9, starting from (2S,4EZ)-1-(tert-butoxycarbonyl)-4-(methoxyimino)-2-pyrrolidinecarboxylic acid, [1,1'-biphenyl]-4-carbonyl chloride, and 2-amino-1-phenylethyl acetate, the title compound was obtained after column chromatography as a mixture of E/Z-isomers as an off-white solid. The two isomers could be separated by another flash chromatographic purification step.

(2S,4E)-1-([1,1'-biphenyl]-4-ylcarbonyl)-N-[(2RS)-2-hydroxy-2-phenethyl]-4-(methoxyimino)-2-pyrrolidinecarboxamide: 1H NMR (400MHz, CDCl3); 2.75–2.9 (m, 1H), 3.1–3.25 (m, 2H), 3.35–3.6 (m, 1H), 3.7–3.8 (m, 1H), 3.75 (s, 3H), 4.1–4.3 (m, 2H), 4.8 (m, 1H), 5.1 (dd, 1H), 7.1–7.6 (m, 15H). M⁺(APCI⁺); 458.

(2S,4Z)-1-([1,1'-biphenyl]-4-ylcarbonyl)-N-[(2RS)-2-hydroxy-2-phenethyl]-4-(methoxyimino)-2-pyrrolidinecarboxamide: 1H NMR (400MHz, CDCl3); 2.7–2.85 (m, 1H), 3.05–3.25 (m, 2H), 3.35 (m, 1H), 3.65–3.8 (m, 1H), 3.8 (s, 3H), 4.15–4.25 (d, 1H), 4.25–4.4 (m, 1H), 4.75 (m, 1H), 5.1 (dd, 1H), 7.15–7.6 (m, 15H). M⁺(APCI⁺); 458.

Example 11

General Protocol for the Solution-Phase Synthesis of Oximether Pyrrolidine Derivatives of General Formula Ib (Scheme 5); (3EZ,5S)-5-(1H-benzimidazol-2-yl)-1-([1,1'-biphenyl]-4-ylcarbonyl)-3-pyrrolidinone O-methyloxime a) Protocol for the Formation of the Amide Bond A solution was prepared containing the central building block, e.g. (2S,4EZ)-1-(tert-butoxycarbonyl)-4-(methoxyimino)-2-pyrrolidinecarboxylic acid (Intermediate 7) (2.1 g, 8.1 mmol), an ortho-substituted aromatic amine or amine salt, e.g. 1,2-benzenediamine (0.88 g, 8.1 mmol) and DMAP (1.59 g, 13.0 mmol). in dry dichloromethane (30 ml). This solution was cooled to 0° C. and treated with EDC (1.56 g, 8.2 mmol) before warming to room temperature and stirring for 2 days. The solvent was removed in vacuo and the product purified by silica gel chromatography, eluting with a gradient of 30–80% ethyl acetate in hexane to give the desired anilide product, e.g. tert-butyl (2S,4EZ)-2-[(2-aminoanilino)carbonyl]-4-(methoxyimino)-1-pyrrolidinecarboxylate 2.8 g, 97% as a colourless foam.

1H NMR (360MHz, CDCl3); 1.7, (m, 9H), 2.5–3.5 (br, 4H), 3.4 (m, 1H), 4.0 (m, 3H), 4.2–4.4 (m, 2H), 4.9 (m, 1H), 6.9–7.5 (m, 4H), 8.5 (br, 1H).

b) Protocol for the Formation of the Fused Heterocyclic Ring

A solution of the anilide compound from the previous step, e.g. tert-butyl (2S,4EZ)-2-[(2-aminoanilino)carbonyl]-4-(methoxyimino)-1-pyrrolidinecarboxylate (0.8 g, 2.3 mmol) in dichloromethane (30 ml) and acetic acid (3 ml) was stirred at room temperature for 3 days. Saturated aqueous sodium bicarbonate (7 ml) was added to the reaction, the organic phase collected and dried over magnesium sulfate before filtering and removal of solvent in vacuo to give the desired product, e.g. tert-butyl (2S,4EZ)-2-(1H-benzimidazol-2-yl)-4-(methoxyimino)-1-pyrrolidinecarboxylate (740 mg, 97%) as an off-white foam.

1H NMR (360MHz, CDCl3); 1.5 (m, 9H), 3.1 (m, 1H), 3.8 (m, 3H) 3.9–4.3 (m, 3H), 5.3 (m, 1H), 7.1–7.6 (m, 4H), 10–10.5 (br, 1H).

c) Protocol for the N-deprotection Step

Hydrogen chloride gas was bubbled into a solution of the fused heterocyclic product from the previous step, e.g. tert-butyl (2S,4EZ)-2-(1H-benzimidazol-2-yl)-4-(methoxyimino)-1-pyrrolidinecarboxylate (740 mg, 2.2 mmol) in dry DCM (20 ml) for 30 min. The solvent was removed in vacuo to give the desired product, e.g. (3EZ,5S)-5-(1H-benzimidazol-2-yl)-3-pyrrolidinone O-methyloxime (0.58 g, 99%), as a brown amorphous powder which was used without further purification.

d) Protocol for the N-capping Step

A solution of the free NH product from the previous step, e.g. (3EZ,5S)-5-(1H-benzimida-zol-2-yl)-3-pyrrolidinone O-methyloxime (0.58 g, 2.2 mmol) in dry dichloromethane (25 ml) was treated with an acid chloride, e.g. [1,1'-biphenyl]-4-carbonyl chloride (0.48 g, 2.2 mmol) and triethylamine (0.9 ml, 6.6 mmol). The resulting solution was then stirred for 3 h at room temp before removal of solvent in vacuo and the desired isomers were isolated by flash chromatography on silica gel, eluting with a gradient of ethyl acetate (10–80%) in hexane to give the two isomers (120 mg of the less polar and 400 mg of the more polar) of the desired product, e.g. (3E,5S)- and (3Z,5S)-5-(1H-benzimidazol-2-yl)-1-([1,1'-biphenyl]-4-ylcarbonyl)-3-pyrrolidinone O-methyloxime, as off-white powders.

(3E,5S)-5-(1H-benzimidazol-2-yl)-1-([1,1'-biphenyl]-4-ylcarbonyl)-3-pyrrolidinone O-methyloxime: 1H NMR (360MHz, CDCl3); 3.2, (m, 1H), 3.8 (s, 3H), 4.0 (m, 1H), 4.3 (m, 2H), 6.0 (m, 1H), 6.0 (m, 1H), 7.2–7.7 (m, 13H), 10–11 (br, 1H). M+(APCI+); 411.

(3Z,5S)-5-(1H-benzimidazol-2-yl)-1-([1,1'-biphenyl]-4-ylcarbonyl)-3-pyrrolidinone O-methyloxime: 1H NMR (360MHz, CDCl$_3$); 3.1, (m, 1H), 3.8 (s, 3H), 3.9 (m, 1H), 4.3 (m, 2H), 6.0 (m, 1H), 6.0 (m, 1H), 7.2–7.7 (m, 13H), 10–11 (br, 1H). M+(APCI+); 411.

Example 12

(3EZ,5S)-5-(1H-benzimidazol-2-yl)-1-[(2'-methyl[1,1'-biphenyl]-4-yl)carbonyl]-3-pyrrolidinone O-methyloxime Following the general method as outlined in Example 1, starting from (2S,4EZ)-1-(tert-butoxycarbonyl)-4-(methoxyimino)-2-pyrrolidinecarboxylic acid, 2'-methyl[1,1'-biphenyl]-4 -carboxylic acid, and 1,2-benzenediamine, the title compound was obtained in 91% purity by HPLC. MS(ESI+): m/z=425.

Example 13

(3EZ,5S)-5-(1-methyl-1H-benzimidazol-2-yl)-1-[(2'-methyl[1,1'-biphenyl]-4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and N$^1$-methyl-1,2-benzenediamine, the title compound was obtained in 83% purity by HPLC. MS(ESI+): m/z=439.

Example 14

(3EZ,5S)-5-(7-hydroxy-1H-benzimidazol-2-yl)-1-[(2'-methyl[1,1'-biphenyl]4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2,3-diaminophenol, the title compound was obtained in 91% purity by HPLC. MS(ESI+): m/z=441.

Example 15

(3EZ,5S)-5-(3,4-dihydro-2-quinazolinyl)-1-[(2'-methyl[1,1'-biphenyl]-4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-(aminomethyl)aniline, the title compound was obtained in 77% purity by HPLC. MS(ESI+): m/z=439.

Example 16

(3EZ,5S)-1-([1,1'-biphenyl]-4-ylcarbonyl)-5-(1-methyl-1H-benzimidazol-2-yl)-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, [1,1'-biphenyl]-4-carbonyl chloride, and N$^1$-methyl-1,2-benzenediamine, the title compound was obtained in 88% purity by HPLC. MS(ESI+): m/z=425.

Example 17

General Protocol for the Solution-Phase Synthesis of Oxime or Hydrazone Pyrrolidine Derivatives of General Formula I (Scheme 6); (2S 4EZ)-1-([1,1'-biphenyl]-4-ylcarbonyl)-4-(hydroxyimino)-N-[(2RS)-2-hydroxy-2phenethyl]-2-pyrrolidinecarboxamide a) Protocol for the Hydrolysis of the Oximether Group.

The starting oximether compounds, e.g. (2S,4EZ)-1-([1,1'-biphenyl]-4-ylcarbonyl)-N-[(2RS)-2-hydroxy-2-phenethyl]-4-(methoxyimino)-2-pyrrolidinecarboxamide, were obtained following the general methods as outlined, e.g., in Example 2, 11 or 22. A solution was made containing the oximether compound, e.g. (2S,4EZ)-1-([1,1'-biphenyl]-4-ylcarbonyl)-N-[(2RS)-2-hydroxy-2-phenethyl]-4-(methoxyimino)-2-pyrrolidinecarboxamide (64 mg, 0.14 mmol), paraformaldehyde powder (95%, 42 mg, 1.41 mmol) and Amberlyst 15 (30 mg) in acetone containing 10% of water (2 mL). The reaction was stirred 4 h at 60° C. Insoluble materials were filtered off and washed with a small amount of acetone. The filtrate was concentrated and the residue was diluted with DCM (15 mL). The organic solution was washed with brine (10 mL), dried over Na2SO4, and concentrated. The desired ketocarbonyl product, e.g. (2S)-1-([1,1 biphenyl]-4-ylcarbonyl)-N-[(2RS)-hydroxy-2-phenylethyl]-4-oxo-2-pyrrolidinecarboxamide (56 mg, 92%) was isolated as a yellow oil and used without further purification.

b) Protocol for the formation of Oxime and/or Hydrazone Compounds

A solution was made containing the keto-pyrrolidine derivative from the previous step, e.g. (2S)-1-([1,1'-biphenyl]-4-ylcarbonyl)-N-[(2RS)-2-hydroxy-2-phenethyl]-4-oxo-2-pyrrolidinecar-boxamide (46 mg, 0.1 mmol) and hydroxylamine hydrochloride (12 mg, 0.17 mmol) in chloroform (1 ml) containing triethylamine (29 mg, 0.29 mmol). The reaction mixture was then stirred at ambient temperature for one day, prior to removal of solvent. The resultant crude reaction mixture was purified by column chromatography using DCM/MeOH (25:1) to collect the desired product, e.g. (2S, 4EZ)-1-([1,1'-biphenyl]-4-ylcarbonyl)-4 -(hydroxy-imino)-N-[(2RS)-2-hydroxy-2-phenethyl]-2-pyrrolidinecarboxamide as a mixture of two isomers as an off-white solid (46 mg, 96% yield).

$^1$H NMR (300MHz, CDCl$_3$); 2.6–3.3 (m, 4H), 4.0–4.7 (m, 4H), 4.9 (m, 1H), 5.5 (m, 1H), 7.1–7.5 (m, 8H), 7.6–7.8 (m, 5H), 8.1 (m, 1H), 10.9 (m, 1H). M$^+$(APCI$^+$); 444.

Example 18

(2S,4EZ)-1-([1,1'-biphenyl]-4-ylcarbonyl)-4-(dimethylhydrazono)-N-[(2RS)-2-hydroxy-2-phenylethyl]-2-pyrrolidinecarboxamide Following the general method as outlined in Example 17, starting from (2S)-1-([1,1'-biphenyl]-4-ylcarbonyl)-N-[(2RS)-2-hydroxy-2-phenylethyl]4-oxo-2-pyrrolidinecarboxamide and N,N-dimethylhydrazine, the resultant crude reaction mixture was purified by column chromatography using DCM/MeOH (30:1) to collect the desired product, e.g. (2S,4EZ)-1-([1,1'-biphenyl]-4-ylcarbonyl)-4-(dimethylhydrazono)-N-[(2RS)-2-hydroxy-2-phenylethyl]-2-pyrrolidinecarboxamide as a mixture of two isomers as a light yellow oil in 56% yield (90.2% purity by HPLC).

$^1$H NMR (300MHz, CDCl$_3$); 2.35–2.55 (br s, 3H), 2.40–2.60 (m, 1H), 2.75–3.55 (m, 5H), 3.55–3.82 (m, 1H), 3.90–4.4 (m, 2H), 4.83 (m, 1H), 4.93–5.35 (m, 1H), 7.18–7.49 (m, 9H), 7.49–7.68 (m, 5H). M$^+$(APCI$^+$); 471. M$^-$(APCI$^-$); 469.

Example 19

(2S,4EZ)-1-(([1,1'-biphenyl]-4-ylcarbonyl)-N-[(2RS)-2-hydroxy-2-phenylethyl-4-methylhydrazono)-2-pyrrolidinecarboxamide Following the general method as outlined in Example 17, staring from (2S)-1-([1,1'-biphenyl]-4-ylcarbonyl)-N-[(2RS)-2-hydroxy-2-phenylethyl]-4-oxo-2-pyrrolidinecarboxamide and N-methylhydrazine, the resultant crude reaction mixture was purified by column chromatography using DCM/MeOH (30:1) to collect the desired product, e.g. (2S,4EZ)-1-([1,1'-biphenyl]-4-ylcarbonyl)-N-[(2RS)-2-hydroxy-2-phenylethyl]-(methylhydrazono)-2-pyrrolidinecarboxamide as a mixture of two isomers as a colorless solid in 57% yield (95.2% purity by HPLC).

$^1$H NMR (300MHz, CDCl$_3$); 2.45–2.70 (m, 1H), 2.85 (br s, 3H, NNHCH$_3$), 2.85–3.5 (m, 2H), 3.51–4.4 (m, 4H), 4.84 (br s, 1H, NNHMe), 4.95–5.35 (m, 1H), 7.18–7.67 (m, 14H). M$^+$(APCI$^+$); 457. M$^-$(APCI$^-$); 455.

Example 20

(2S,4EZ)-1-([1,1'-biphenyl]-4-ylcarbonyl)-4-hydrazono-N-[(2RS)-2-hydroxy-2-phenylethyl]-2-pyrrolidinecarboxamide Following the general method as outlined in Example 17, starting from (2S)-1-([1,1'-biphenyl]-4-ylcarbonyl)-N-[(2RS)-2-hydroxy-2-phenylethyl]-4-oxo-2-pyrrolidinecarboxamide and hydrazine hydrate (4% in EtOH), the resultant crude reaction mixture was purified by column chromatography using DCM/MeOH (30:1) to collect the desired product, e.g. (2S,4EZ)-1-([1,1'-biphenyl]-4-ylcarbonyl)-4-hydrazono-N-[(2RS)-2-hydroxy-2-phenylethyl]-2-pyrrolidinecarboxamide as a mixture of two isomers as a colorless solid in 63% yield (95.3% purity by HPLC).

$^1$H NMR (300MHz, DMSO-d$_6$, 80° C.); 2.55 (dd, J=9.8; 17.6 Hz, 1H), 2.73 (dd, J=9.8; 18.2 Hz, 1H), 3.28 (m, 2H), 4.12 (m, 2H), 4.61 (m, 1H), 4.85 (m, 1H), 5.15 (m, 1H), 5.70 (br s, 2H, NH$_2$N=C), 7.17–7.43 (m, 6H), 7.44–7.60 (m, 4H), 7.66–7.77 (m, 5H). M(APCI$^+$); 443. M$^-$(APCI$^-$); 441.

Example 21

(2S,4EZ)-4-(acetylhydrazono)-1-([1,1'-biphenyl]-4-ylcarbonyl)-N-[(2RS)-2-hydroxy-2-phenylethyl]-2-pyrrolidinecarboxamide A hydrazono pyrrolidine derivative obtained by the general method outlined in Example 17, e.g. (2S,4EZ)-1-([1,1'-biphenyl]-4ylcarbonyl)-4-hydrazono-N-[(2RS)-2-hydroxy-2-phenylethyl]-2-pyrrolidinecarboxamide (51 mg, 0.111 mmol) was dissolved in pyridine (1 mL). Acetic anhydride (3 eq, 32 µl, 0.35 mmol) was added, and the mixture was stirred overnight. The solvent was evaporated and the resultant crude reaction mixture was purified by column chromatography using DCM/MeOH (20:1) to collect the desired product, e.g. (2S,4EZ)-4-(acetylhydrazono)-1-([1,1'-biphenyl]-4-ylcarbonyl)-N-[(2RS)-2-hydroxy-2-phenylethyl]-2- pyrrolidinecarboxamide as a mixture of two isomers as a colorless solid in 73% yield (98.4% purity by HPLC).

$^1$H NMR (300MHz, DMSO-d$_6$, 80° C.); 1.99 (br s, 3H, CH$_3$CON), 2.7–3.4 (m, 5H), 4.26 (m, 2H), 4.63 (m, 1H), 4.89 (m, 1H), 5.15 (m, 1H), 7.18–7.44 (m, 6H), 7.45–7.62 (m, 4H), 7.66–7.85 (m, 5H), 9.97 (br s, 1H, MeCONHN, major isomer), 10.04 (br s, 1H, MeCONHN, minor isomer). M$^+$(ESI$^+$); 485. M$^-$(ESI$^-$); 483.

Example 22

General Protocol for the Solid-phase Synthesis of Pyrrolidine Derivatives of General Formula I.

a) Loading Step

Kaiser oxime resin (16.5 g, loading 1.57 mmol/g) was added to a solution of the relevant pyrrolidine carboxylic acid building block (51.8 mmol) and diisopropylcarbodiimide (8.1 ml, 51.8 mmol) in dry dichloromethane (150 ml). The resulting suspension was shaken over-night before filtering at the pump and washing sequentially with DMF, DCM and finally diethyl ether before drying at room temperature in vacuo.

b) N-deprotection Step

The resin obtained in the loading step was shaken with a 20% solution of trifluoroacetic acid in dichloromethane (200 ml) for 30 minutes prior to filtering at the pump and washing sequentially with aliquots of DMF, DCM and finally diethyl ether before drying at room temperature in vacuo.

c) N-capping Step

The resin from the previous step was transferred into a 96-well filter-plate (approx. 50 mg of dry resin/well) and each well treated with an N-reactive derivatising agent, e.g. with either of the following solutions:

a) an acid chloride (0.165 mmol) and diisopropylethylamine (0.165 mmol) in dry dichloromethane (1 ml), overnight
b) an acid (0.165 mmol) and DIC (0.165 mmol) in, depending on the solubility of the carboxylic acid, dry dichloromethane or NMP (1 ml) overnight.
c) an isocyanate (0.165 mmol) in dry THF (1 ml), overnight
d) a sulfonyl chloride (0.165 mmol) and diisopropylethylamine (0.165 mmol) in NMP (1 ml), overnight
e) a benzyl (alkyl) bromide (0.165 mmol) and diisopropylethylamine (0.165 mmol) in NMP, (1 ml), overnight.
f) a vinyl ketone (0.165 mmol) in THF, overnight
g) diketene (0.165 mmol) in THF, overnight The plate was then sealed and shaken overnight at ambient temperature. The resins were then filtered, washing the resin sequentially with aliquots of DMF, DCM and finally diethyl ether before drying at room temperature in vacuo.

d) Cleavage Step

A solution of amine (0.05 mmol) in 2% AcOH in dichloromethane (1 ml) was added to each well containing the resin from the previous step. The plate was then sealed and shaken for two days at ambient temperature. The wells were then filtered into a collection plate and the solvent removed in a vacuum centrifuge to yield 2–3 mg of the corresponding products, generally obtained as oils. The products were characterised by LC (205 nm) and mass spectrometry (ES+). All of the following examples were identified based on the observation of the correct molecular ion in the mass spectrum, and were shown to be at least 40% pure (usually 60–95% pure) by LC.

Example 23

(2S,4EZ)-N$^2$-(2-hydroxyethyl)-4-(methoxyimino)-N$^1$-pentyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 2-aminoethanol the title compound was obtained in 100% purity by LC/MS. MS(ESI+): m/z=315.2.

Example 24

(2S,4EZ)-4-benzylidene-1-([1,1'-biphenyl]-4-ylcarbonyl)-N-[2-(diethylamino)-ethyl-2-pyrrolidinecarboxamide Following the general method as outlined in Example 22, starting from (2S,4EZ)-4-benzylidene-1-(tert-butoxycarbonyl)-2-pyrrolidinecarboxylic acid, [1,1'-biphenyl]-4-carbonyl chloride, and N1,N1-diethyl-1,2-ethanediamine the title compound was obtained in 90% purity by LC/MS. MS(ESI+): m/z=482.4.

Example 25

(2S,4EZ)-4-[(allyloxy)imino]-1-(4-cyanobenzoyl)-N-[2-(1H-pyrrol-1-yl)phenyl]-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-cyanobenzoyl chloride, and 2-(1H-pyrrol-1-yl)phenylamine the title compound was obtained in 51% purity by LC/MS. MS(ESI+): m/z=454.4.

Example 26

(2S,4EZ)-4-{[(3,4-dichlorobenzyl)oxy]imino}-N-(2-furylmethyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2-oxo-6-pentyl-2H-pyran-3-carbonyl chloride, and 2-furylmethylamine the title compound was obtained in 92% purity by LC/MS. MS(ESI+): m/z=574.4.

Example 27

(2S,4EZ)-4methoxyimino)-N$^1$-(3-methoxyphenyl)-N$^2$-thienylmethyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methoxybenzene, and 2-thienylmethylamine the title compound was obtained in 79% purity by LC/MS. MS(ESI+): m/z=403.2.

Example 28

(2S,4EZ)-2-{[4-(1,3-benzodioxol-5-ylmethyl)-1-piperazinyl]carbonyl}-4-(methoxyimino)-N-pentyl-1-pyrrolidinecarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 1-(1,3-benzodioxol-5-ylmethyl)piperazine the title compound was obtained in 72% purity by LC/MS. MS(ESI+): m/z=474.4.

Example 29

(2S,4EZ)-4-[(benzyloxy)imino]-1-(4-cyanobenzoyl)-N-(2-furylmethyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 2-furylmethylamine the title compound was obtained in 49% purity by LC/MS. MS(ESI+): m/z=443.4.

Example 30

(2S,4EZ)-4-[(benzyloxy)imino]-N-[2-(diethylamino)ethyl]-1-(4-phenoxybenzoyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-phenoxybenzoyl chloride, and N1,N1-diethyl-1,2-ethanediamine the title compound was obtained in 86% purity by LC/MS. MS(ESI+): m/z=529.6.

Example 31

4-[(((2S,4EZ)-4-[(benzyloxy)imino]-2-{[4-(3,4-dichlorophenyl)-1-piperazinyl]-carbonyl}pyrrolidinyl)carbonyl]benzonitrile Following the general method as outlined in Example 22, starting from (2S,4EZ)-4-[(benzyloxy)imino]-1-(tert-butoxycarbonyl)-2-pyrrolidinecarboxylic acid, 4cyanobenzoyl chloride, and 1-(3,4-dichlorophenyl)piperazine the title compound was obtained in 43% purity by LC/MS. MS(ESI+): m/z=576.6.

Example 32

(2S,4EZ)-4-(methoxyimino)-$N^1$-pentyl-$N^2$-[2-(1H-pyrrol-1-yl)phenyl]-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 2-(1H-pyrrol-1-yl)phenylamine the title compound was obtained in 74% purity by LC/MS. MS(ESI+): m/z=412.2.

Example 33

(2S,4EZ)-1-acryloyl-4-{[(3,4-dichlorobenzyl)oxy]imino}-N-(2-furylmethyl-2-pyrrolidinecarboxamide Following the general method as outlined in Example 22, starting from (2S,4EZ)-1-(tert-butoxycarbonyl)-4-{[(3,4-dichlorobenzyl)oxy]imino }-2-pyrrolidinecarboxylic acid, acryloyl chloride, and 2-furylmethylamine the title compound was obtained in 74% purity by LC/MS. MS(ESI+): m/z=436.8.

Example 34

(2S,4EZ)-4-(tert-butoxyimino)-$N^2$-cyclopropyl-$N^1$-(3,5-dichlorophenyl)-1,2-pyrrolidinedicarboxamide Following the general method as outlined in Example 22, starting from (2S,4EZ)-1-(tertbutoxycarbonyl)-4-(tert-butoxyimino)-2-pyrrolidinecarboxylic acid, 1,3-dichloro-5-isocyanatobenzene, and cyclopropylamine the title compound was obtained in 48% purity by LC/MS. MS(ESI+): m/z=427.6.

Example 35

(2S,4EZ)-4-[(allyloxy)imino]-N-[2-(diethylamino)ethyl]-1-l(2-oxo-6-pentyl-2H-pyran-3-yl)carbonyl]-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 2-oxo-6-pentyl-2H-pyran-3-carbonyl chloride, and N1,N1-diethyl-1,2-ethanediamine the title compound was obtained in 93% purity by LC/MS. MS(ESI+): m/z=475.4.

Example 36

(2S,4EZ)-$N^2$-[(2RS)-2-hydroxy-2-phenethyl]-4-(methoxyimino)-$N^1$-(3-methylphenyl)-1,2-pyrrolidinedicarboxamide Following the general method as outlined in Example 22, starting from (2S,4EZ)-1-(tertbutoxycarbonyl)-4-(methoxyimino)-2-pyrrolidinecarboxylic acid, 1-isocyanato-3-methylbenzene, and (1RS)-2-amino-1-phenylethanol the title compound was obtained in 100% purity by LC/MS. MS(ESI+): m/z=411.2.

Example 37

(2S,4EZ)-1-[(benzoylamino)carbonyl]-N-benzyl-4-[(benzyloxy)imino]-N-methyl-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, benzoyl isocyanate, and N-benzyl-N-methylamine the title compound was obtained in 40% purity by LC/MS. MS(ESI+): m/z=485.4.

Example 38

(2S,4EZ)-1-(4-cyanobenzoyl)-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-cyanobenzoyl chloride, and 9-ethyl-9H-carbazol-3-amine the title compound was obtained in 72% purity by LC/MS. MS(ESI+): m/z=480.4.

Example 39

(2S,4EZ)-4-(methoxyimino)-$N^1$-(3-methylphenyl)-$N^2$-(2-thienylmethyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methylbenzene, and 2-thienylmethylamine the title compound was obtained in 98% purity by LC/MS. MS(ESI+): m/z=387.2.

Example 40

(2S,4EZ)-4-(tert-butoxyimino)-N-(2-methoxyethyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 2-methoxyethylamine the title compound was obtained in 75% purity by LC/MS. MS(ESI+): m/z=450.2.

Example 41

(3EZ,5S)-5-{[4-(1,3-benzodioxol-5-ylmethyl)-1-piperazinyl]carbonyl}-1-benzoyl-3-pyrrolidinone O-(3,4-dichlorobenzyl)oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, benzoyl chloride, and 1-(1,3-benzodioxol-5-ylmethyl)piperazine the title compound was obtained in 71% purity by LC/MS. MS(ESI+): m/z=609.8.

Example 42 tert-butyl 3-[({(2S,4EZ)-4-(ethoxyimino)-1-(2-oxo-6-pentyl-2H-pyran-3-yl)carbonyl]pyrrolidinyl}carbonyl)amino]-1-azetidinecarboxylate Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and tert-butyl 3-amino-1-azetidinecarboxylate the title compound was obtained in 100% purity by LC/MS. MS(ESI+): m/z=519.6.

Example 43

(2S,4EZ)-4-{[(4-methoxybenzyl)oxy]imino}-N-(3-methylphenyl)-2-(4-morpholinylcarbonyl)-1-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanato-3-methylbenzene, and morpholine the title compound was obtained in 41% purity by LC/MS. MS(ESI+): m/z=467.4.

Example 44

(2S,4EZ)-$N^2$-cyclopropyl-4-{[(4-methoxybenzyl)oxy]imino}-$N^1$-pentyl-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and cyclopropylamine the title compound was obtained in 75% purity by LC/MS. MS(ESI+): m/z=417.2.

Example 45

(3EZ,5S)-5-{4-(3,4-dichlorophenyl)-1-piperazinyl]carbonyl}-1-[(2-oxo-6-pentyl-2H-pyran-3-yl)carbonyl]-3-pyrrolidinone O-benzyloxime Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 1-(3,4-dichlorophenyl)piperazine the title compound was obtained in 47% purity by LC/MS. MS(ESI+): m/z=639.8.

Example 46

(2S,4EZ)-4-(tert-butoxyimino)-N-[2-(1H-pyrrol 1-yl)phenyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, and 2-(1H-pyrrol-1-yl)phenylamine the title compound was obtained in 83% purity by LC/MS. MS(ESI+): m/z=341.2.

Example 47

1-({(2S,4EZ)-4-(chloromethylene)-1-[(4-chlorophenoxy)acetyl]pyrrolidinyl}carbonyl)-4-(3,4-dichlorophenyl)piperazine Following the general method as outlined in Example 22, starting from (2S,4EZ)-1-(tert-butoxycarbonyl)-4-(chloromethylene)-2-pyrrolidinecarboxylic acid, (4-chlorophenoxy)acetyl chloride, and 1-(3,4-dichlorophenyl)piperazine the title compound was obtained in 64% purity by LC/MS. MS(ESI+): m/z=543.6.

Example 48

(2S,4EZ)-4-[(benzyloxy)imino]-N-(4,6-dimethoxy-2-pyrimidinyl)-1-[(2-oxo-6-pentyl-2H-pyran-3-yl)carbonyl]-2-pyrrolidinecarboxamide Following the general method as outlined in Example 22, staring from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 4,6-dimethoxy-2-pyrimidinamine the title compound was obtained in 62% purity by LC/MS. MS(ESI+): m/z=564.6.

Example 49

(2S,4EZ)-4-{[(3,4-dichlorobenzyl)oxy]imino}-1-[4-(dimethylamino)butanoyl]-N-(1-naphthylmethyl)-2-pyrrolidinecarboxamide Following the general method as outlined in Example 22, starting from (2S,4EZ)-1-(tert-butoxycarbonyl)-4-{[(3,4dichlorobenzyl)oxy]imino})-2-pyrrolidinecarboxylic acid, 4-(dimethylamino)butanoyl chloride, and 1-naphthylmethylamine the title compound was obtained in 62% purity by LC/MS. MS(ESI+): m/z=555.6.

Example 50

(2S)-$N^2$-(2,1,3-benzothiadiazol-4-yl)-$N^1$-(3,5-dichlorophenyl)-4-oxo-1,2-pyrrolidinedicarboxamide Following the general method as outlined in Example 22, starting from 1-(tert-butoxycarbonyl)-4-oxoproline, 1,3-dichloro-5-isocyanatobenzene, and 2,1,3-benzothiadiazol-1-amine the title compound was obtained in 47% purity by LC/MS. MS(ESI+): m/z=450.6.

Example 51

(2S,4EZ)-N-benzyl-4-(chloromethylene)-N-methyl-1-(4-phenoxybenzoyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, 4-phenoxybenzoyl chloride, and N-benzyl-N-methylamine the title compound was obtained in 61% purity by LC/MS. MS(ESI+): m/z=461.4.

Example 52

(2S,4EZ)-$N^2$-(9-ethyl-9H-carbazol-3-yl)-4-{[(4-methoxybenzyl)oxy]imino}-$N^1$-(3-methylphenyl)-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocya-nato-3-methylbenzene, and 9-ethyl-9H-carbazol-3-amine the title compound was obtained in 72% purity by LC/MS. MS(ESI+): m/z=590.8.

Example 53

(2S)-N-(tert-butyl)-4-methylene-1-[(2-oxo-6-pentyl-2H-pyran-3-yl)carbonyl]-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and tert-butylamine the title compound was obtained in 100% purity by LC/MS. MS(ESI+): m/z=375.4.

Example 54

(2S,4EZ)-4-benzylidene-1-[4-(dimethylamino)butanoyl]-N-(6-quinolinyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, 4-(dimethylamino)butanoyl chloride, and 6-quinolinamine the title compound was obtained in 71% purity by LC/MS. MS(ESI+): m/z=443.6.

Example 55

(2S)-1-[4-(dimethylamino)butanoyl]-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, 4-(dimethylamino)butanoyl chloride, and 9-ethyl-9H-carbazol-3-amine the title compound was obtained in 51% purity by LC/MS. MS(ESI+): m/z=433.6.

Example 56

(2S,4EZ)-N-(1,3-benzodioxol-5-ylmethyl)-4-[benzyloxy)imino]-1-(4-cyanobenzoyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 1,3-benzodioxol-5-ylmethylamine the title compound was obtained in 51% purity by LC/MS. MS(ESI+): m/z=497.6.

Example 57

(2S)-1-({1-[4-(dimethylamino)butanoyl]-4-methylene-2-pyrrolidinyl}carbonyl)-3-azetidinol Following the general method as outlined in Example 22, starting from 1-(tert-butoxycarbonyl)-4-methyleneproline, 4-(dimethylamino)butanoyl chloride, and 3-azetidinol the title compound was obtained in 100% purity by LC/MS. MS(ESI+): m/z=296.4.

Example 58

(2S,4EZ)-1-([1,1'-biphenyl]-4-ylcarbonyl)-4-{[(3,4-dichlorobenzyl)oxy]imino}-N-[2-(1H-pyrrol-1-yl)phenyl]-2-pyrrolidinecarboxamide Following the general method as outlined in Example 22, starting from (2S,4EZ)-1-(tert-butoxycarbonyl)-4-{[(3,4- dichlorobenzyl)oxy]imino}-2-pyrrolidinecarboxylic acid, [1,1'-biphenyl]-4-carbonyl chloride, and 2-(1H-pyrrol-1-yl)phenylamine the title compound was obtained in 54% purity by LC/MS. MS(ESI+): m/z=623.6.

Example 59

(2S,4EZ)-4-benzylidene-1-[(4-chlorophenoxy)acetyl]-N-(3,4dimethoxybenzyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, (4-chlorophenoxy)acetyl chlo-ride, and 3,4-dimethoxybenzylamine the title compound was obtained in 49% purity by LC/MS. MS(ESI+): m/z=521.6.

Example 60

(2S,4EZ)-4-{[(3,4-dichlorobenzyl)oxy]imino}-1-(diphenylacetyl)-N-(2-thienylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, diphenylacetyl chloride, and 2-thienylmethylamine the title compound was obtained in 51% purity by LC/MS. MS(ESI+): m/z=592.6.

Example 61

(2S,4EZ)-N-(3,4-dimethoxybenzyl)-1-(diphenylacetyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 3,4-dimethoxybenzylamine the title compound was obtained in 74% purity by LC/MS. MS(ESI+): m/z=502.6.

Example 62

(2S,4EZ)-N$^1$-(3,5-dichlorophenyl)-4-(ethoxyimino)-N$^2$-[2-(1H-pyrrol-1-yl)phenyl]-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1,3-dichloro-5-isocyanatobenzene, and 2-(1H-pyrrol-1-yl)phenylamine the title compound was obtained in 54% purity by LC/MS. MS(ESI+): m/z=500.6.

Example 63

(2S,4EZ)-N$^2$-(1,3-benzodioxol-5-ylmethyl)-4-{[(4-methoxybenzyl)oxy]imino}-N$^1$-pentyl-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and 1,3-benzodioxol-5-ylmethylamine the title compound was obtained in 63% purity by LC/MS. MS(ESI+): m/z=511.4.

Example 64

(2S,4EZ)-N-benzyl-4-[(benzyloxy)imino]-1-(diphenylacetyl)-N-methyl-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, diphenylacetyl chloride, and N-benzyl-N-methylamine the title compound was obtained in 42% purity by LC/MS. MS(ESI+): m/z=532.4.

Example 65

(2S,4EZ)-N-(2,1,3-benzothiadiazol-4-yl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2,1,3-benzothiadiazol-4-amine the title compound was obtained in 66% purity by LC/MS. MS(ESI+): m/z=472.4.

Example 66

(2S,4EZ)-1-([1,1'-biphenyl]-4-ylcarbonyl)-4-(methoxyimino)-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 6-quinolinamine the title compound was obtained in 79% purity by LC/MS. MS(ESI+): m/z=465.4.

Example 67

(2S,4EZ)-1-acetoacetyl-N-benzyl-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, 2,4-oxetanedione, and benzylamine the title compound was obtained in 45% purity by LC/MS. MS(ESI+): m/z=332.2.

Example 68

(2S,4EZ)-1-(1,1'-biphenyl]-4-ylcarbonyl)-4-(chloromethylene)-N-(2-furylmethyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and 2-furylmethylamine the title compound was obtained in 70% purity by LC/MS. MS(ESI+): m/z=421.4.

Example 69

(2S,4EZ)-1-[(4-chlorophenoxy)acetyl]-4-{[(3,4-dichlorobenzyl)oxy]imino}-N-[(2RS)-2-hydroxy-2-phenethyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, (4-chlorophenoxy)acetyl chloride, and (1RS)-2-amino-1-phenylethanol the title compound was obtained in 62% purity by LC/MS. MS(ESI+): m/z=590.8.

Example 70

(2S,4EZ)-N-allyl-1-([1,1'-biphenyl]-4-ylcarbonyl)-4-(methoxyimino -2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and allylamine the title compound was obtained in 87% purity by LC/MS. MS(ESI+): m/z=378.2.

Example 71

(2S,4EZ)-1-([1,1'-biphenyl]-4-ylcarbonyl)-4-(methoxyimino)-N-(2-thienylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-thienylmethylamine the title compound was obtained in 78% purity by LC/MS. MS(ESI+): m/z=434.4.

Example 72

(2S,4EZ)-4-(cyanomethylene)-N-(2-furylmethyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 2-oxo-6-pentyl-2H-pyran-3-carbonyl chloride, and 2-furylmethylamine the title compound was obtained in 34% purity by LC/MS. MS(ESI+): m/z=424.4.

Example 73

(2S,4EZ)-1-([1,1'-biphenyl]-4-ylcarbonyl)-N-(2-furylmethyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-furylmethylamine the title compound was obtained in 75% purity by LC/MS. MS(ESI+): m/z=418.4.

Example 74

(2S,4EZ)-1-acetyl-N-cyclopropyl-4-{[(3,4-dichlorobenzyl)oxy]imino}-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and cyclopropylamine the title compound was obtained in 52% purity by LC/MS. MS(ESI+): m/z=384.4.

Example 75

(2S,4EZ)-N-(2-furylmethyl)-4-(methoxyimino)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-oxo-6-pentyl-2H-pyran-3-carbonyl chloride, and 2-furylmethylamine the title compound was obtained in 62% purity by LC/MS. MS(ESI+): m/z=430.4.

Example 76

(2S,4EZ)-N-benzyl-1-([1,1'-biphenyl]-4-ylcarbonyl)-4-(methoxyimino)-N-methyl-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and N-benzyl-N-methylamine the title compound was obtained in 67% purity by LC/MS. MS(ESI+): m/z=442.4.

Example 77

(2S,4EZ)-1-(diphenylacetyl)-4-(ethoxyimino)-N-(2-thienylmethyl-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, diphenylacetyl chloride, and 2-thienylmethylamine the title compound was obtained in 74% purity by LC/MS. MS(ESI+): m/z=462.4.

Example 78

(2S,4EZ)-N-(2,1,3-benzothiadiazol-4-yl-4-(cyanomethylene)-1-(diphenylacetyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, diphenylacetyl chloride, and 2,1,3-benzothiadiazol-4-amine the title compound was obtained in 42% purity by LC/MS. MS(ESI+): n/z=480.4.

Example 79

(2S)-1-(diphenylacetyl)-N-(1-naphthylmethyl)-4-oxo-2-pyrrolidinecarboxamide

Following the general method as outlined in Example 22, starting from 1-(tert-butoxycarbonyl)-4-oxoproline, diphenylacetyl chloride, and 1-naphthylmethylamine the title com-pound was obtained in 60% purity by LC/MS. MS(ESI+): m/z=463.4.

Example 80

(3EZ,5S)-5-(1H-benzimidazol-2-yl)-1-(diphenylacetyl-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, diphenylacetyl chloride, and 1,2-benzenediamine the title compound was obtained in 72% purity by LC/MS. MS(ESI+): m/z=425.4.

Example 81

(2S)-2-[1-([1,1'-biphenyl]-4-ylcarbonyl)-4-methylene-2-pyrrolidinyl]-1H-benzimidazole Following the general method as outlined in Example 22, starting from 1-(tert-butoxycarbonyl)-4-methyleneproline, [1,1'-biphenyl]-4-carbonyl chloride, and 1,2-benzenediamine the title compound was obtained in 73% purity by LC/MS. MS(ESI+): m/z=380.4.

Example 82

(2S,4EZ)-1-([1,1'-biphenyl]-4-ylcarbonyl)-4-(chloromethylene)-N-(2-methoxyethyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbonyl chloride, and 2-methoxyethylamine the title compound was obtained in 55% purity by LC/MS. MS(ESI+): m/z=399.6.

Example 83

(3EZ,5S)-5-(1H-benzimidazol-2-yl)-1-(diphenylacetyl)-3-pyrrolidinone O-allyloxime Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 1,2-benzenediamine the title compound was obtained in 63% purity by LC/MS. MS(ESI+): m/z=451.4.

Example 84

(2S,4EZ)-1-([1,1'-biphenyl]-4-ylcarbonyl)-N-[2-(diethylamino)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and N1,N1-diethyl-1,2-ethanediamine the title compound was obtained in 90% purity by LC/MS. MS(ESI+): mz=437.4.

Example 85

(2S,4EZ)-1-(diphenylacetyl)-4-{[(4-methoxybenzyl)oxy]imino}-N-(2-thienylmethyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and 2-thienylmethylamine the title compound was obtained in 63% purity by LC/MS. MS(ESI+): m/z=554.4.

Example 86

(2S,4EZ)-1-([1,1'-biphenyl]-4-ylcarbonyl)-N-(3,4-dimethoxybenzyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3,4-dimethoxybenzylamine the title compound was obtained in 58% purity by LC/MS. MS(ESI+): m/z=488.4.

Example 87

(2S,4EZ)-1-acetoacetyl-4-(methoxyimino)-N-(1-naphthylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 1-naphthylmethylamine the title compound was obtained in 40% purity by LC/MS. MS(ESI+): m/z=382.2.

Example 88

(2S,4EZ)-N-allyl-4-{[(3,4-dichlorobenzyl)oxy]imino}1-(diphenylacetyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, diphenylacetyl chloride, and allylamine the title compound was obtained in 54% purity by LC)MS. MS(ESI+): m/z=536.6.

Example 89

(2S,4EZ)-4-{[(3,4-dichlorobenzyl)oxy]imino}-$N^1$-pentyl-$N^2$-(6-quinolinyl)-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1-isocyanatopentane, and 6-quinolinamine the title compound was obtained in 54% purity by LC/MS. MS(ESI+): m/z=542.6.

Example 90

(2S,4EZ)-4-(chloromethylene)-1-(diphenylacetyl)-N-[(2RS)-2-hydroxy-2-phenethyl]-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, diphenylacetyl chloride, and (1RS)-2-amino-1-phenylethanol the title compound was obtained in 87% purity by LC/MS. MS(ESI+): m/z=475.4.

Example 91

(2S)-1-([1,1'-biphenyl]-4-ylcarbonyl)-N-[(2RS)-2-hydroxy-2-phenethyl]-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 2-amino-1-phenylethanol the title compound was obtained in 74% purity by LC/MS. MS(ESI+): m/z=427.4.

Example 92

(2S,4EZ)-1-([1,1'-biphenyl]-4-ylcarbonyl)-4-(chloromethylene)-N-(6-quinolinyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and 6-quinolinamine the title compound was obtained in 73% purity by LC/MS. MS(ESI+): m/z=468.4.

Example 93

(2S,4EZ)-4-benzylidene-N-[2-(diethylamino)ethyl]-1-(diphenylacetyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, diphenylacetyl chloride, and N1,N1-diethyl-1,2-ethanediamine the title compound was obtained in 71% purity by LC/MS. MS(ESI+): m/z=496.4.

Example 94

(2S,4EZ)-1-acetoacetyl-4-(methoxyimino)-N-(2-thienylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 2-thienylmethylamine the title compound was obtained in 42% purity by LC/NS. MS(ESI+): m/z=338.2.

Example 95

(2S,4EZ)-1-acetyl-4-{[(3,4-dichlorobenzyl)oxy]imino}-N-(2-hydroxy-2-phenylethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and (1RS)-2-amino-1-phenylethanol the title compound was obtained in 48% purity by LC/MS. MS(ESI+): m/z=464.6.

Example 96

(2S,4EZ)-4-{[(3,4-dichlorobenzyl)oxy]imino}-$N^1$-(3,5-dichlorophenyl)-$N^2$-(6-quinolinyl)-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1,3-dichloro-5-isocyanatobenzene, and 6-quinolinamine the title compound was obtained in 66% purity by LC/MS. MS(ESI+): m/z=617.2.

Example 97

(2S,4EZ)-4-(methoxyimino)-N-(1-naphthylmethyl)-1-(phenoxyacetyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, phenoxyacetyl chloride, and 1-naphthylmethylamine the title compound was obtained in 99% purity by LC/MS. MS(ESI+): m/z=432.2.

Example 98

(2S,4EZ)-4-(chloromethylene)-N-(3,4-dimethoxybenzyl)-1-[(2-oxo-6-pentyl-2H-pyran-3-yl)carbo-nyl]-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, 2-oxo-6-pentyl-2H-pyran-3-carbonyl chloride, and 3,4-dimethoxybenzylamine the title compound was obtained in 51% purity by LC/MS. MS(ESI+): m/z=503.4.

Example 99

(2S,4EZ)-1-(diphenylacetyl)-4-(methoxyimino)-N-(2-thienylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 2-thienylmethylamine the title compound was obtained in 88% purity by LC/MS. MS(ESI+): m/z=448.4.

Example 100

(2S,4EZ)-N-benzyl-1-(diphenylacetyl)-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, diphenylacetyl chloride, and benzylamine the title compound was obtained in 82% purity by LC/MS. MS(ESI+): m/z=442.4.

Example 101

(2S,4EZ)-1-([1,1'-biphenyl]-4-ylcarbonyl)-4-{[(3,4-dichlorobenzyl)oxy]imino}-N-[2-(diethylamino)ethyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, [1,1'-biphenyl]-4-carbonyl chloride, and N1,N1-diethyl-1,2-ethanediamine the title compound was obtained in 74% purity by LC/MS. MS(ESI+): m/z=581.6.

Example 102

(2S,4EZ)-4-{[(3,4-dichlorobenzyl)oxy]imino}-1-[4-(dimethylamino)butanoyl]-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4(dimethylamino)butanoyl chloride, and 6-quinolinamine the title compound was obtained in 95% purity by LC/MS. MS(ESI+): m/z=542.6.

Example 103

(2S,4EZ)-1-([1,1'-biphenyl]-4-ylcarbonyl)-N-(5-ethyl-1,3,4-thiadiazol-2-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 5-ethyl-1,3,4-thiadiazol-2-amine the title compound was obtained in 89% purity by LC/MS. MS(ESI+): m/z=450.2.

Example 104

(2S,4EZ)-N-benzyl-1-([1,1'-biphenyl]-4-ylcarbonyl)-4(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-carbonyl chloride, and benzylamine the title compound was obtained in 72% purity by LC/MS. MS(ESI+): m/z=428.2.

Example 105

(2S,4EZ)-N-benzyl-1-(diphenylacetyl)-4-(ethoxyimino)-2-pyrrolidinecarboxamide

Following the general method as outlined in Example 22, starting from (2S,4EZ)-1-(tert-butoxycarbonyl)-4-(ethoxyimino)-2-pyrrolidinecarboxylic acid, diphenylacetyl chloride, and benzylamine the title compound was obtained in 53% purity by LC/MS. MS(ESI+): m/z=456.4.

Example 106

(2S,4EZ)-$N^2$-cyclopropyl-4-{[(3,4-dichlorobenzyl)oxy]imino}-$N^1$-(3-methoxyphenyl)-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1-isocyanato-3-methoxybenzene, and cyclopropylamine the title compound was obtained in 45% purity by LC/MS. MS(ESI+): m/z=491.6.

Example 107

(2S,4EZ)-1-(diphenylacetyl)-N-[(2RS)-2-hydroxy-2-phenethyl]-4-{[(4-methoxyben-zyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and (1RS)-2-amino-1-phenylethanol the title compound was obtained in 66% purity by LC/MS. MS(ESI+): m/z=578.4.

Example 108

(2S)-N-(2-furylmethyl)-4-methylene-1-[(2-oxo-6-pentyl-2H-pyran-3-yl)carbonyl-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and 2-furylmethylamine the title compound was obtained in 43% purity by LC/MS. MS(ESI+): m/z=399.2.

Example 109

(2S,4EZ)-N-(2,1,3-benzothiadiazol-4-yl)-1-(diphenylacetyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 2,1,3-benzothiadiazol-4-amine the title compound was obtained in 69% purity by LC/MS. MS(ESI+): mz=486.4.

Example 110

(2S)-N1-(3,5-dichlorophenyl)-N2-(3,4-dimethoxybenzyl)-4-oxo-1,2-pyrrolidine-dicarboxamide Following the general method as outlined in Example 22, starting from 1-(tert-butoxycarbonyl)-4-oxoproline, 1,3-dichloro-5-isocyanatobenzene, and 3,4-dimethoxybenzylamine the title compound was obtained in 48% purity by LC/MS. MS(ESI+): m/z=466.6.

Example 111

(2S,4EZ)-N-benzyl-1-(diphenylacetyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and benzylamine the title compound was obtained in 60% purity by LC/MS. MS(ESI+): m/z=548.4.

Example 112

(2S,4EZ)-1-benzoyl-4-{[(3,4-dichlorobenzyl)oxy]imino}-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, benzoyl chloride, and 6-quinolinamine the title compound was obtained in 67% purity by LC/MS. MS(ESI+): m/z=533.6.

Example 113

(2S,4EZ)-1-acetoacetyl-N-cyclopropyl-4-{[(3,4-dichlorobenzyl)oxy]imino}-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2,4-oxetanedione, and cyclopropylamine the title compound was obtained in 76% purity by LC/MS. MS(ESI+): m/z=426.6.

Example 114

(2S,4EZ)-4-{[(3,4-dichlorobenzyl)oxy]imino}-N²-[(2RS)-2-hydroxy-2-phenethyl]-N¹-pentyl-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1-isocyanatopentane, and (1RS)-2-amino-1-phenylethanol the title compound was obtained in 47% purity by LC/MS. MS(ESI+): m/z=535.6.

Example 115

(2S,4EZ)-4-[(benzyloxy)imino]-N-(1-naphthylmethyl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and 1-naphthylmethylamine the title compound was obtained in 74% purity by LC/MS. MS(ESI+): m/z=508.4.

Example 116

(2S)-1-([1,1'-biphenyl]-4-ylcarbonyl)-4methylene-N-(6-quinolinyl)-2-pyrrolidinecarboxamide Following the general method as outlined in Example 22, starting from 1-(tert-butoxycarbonyl)-4-methyleneproline, [1,1'-biphenyl]-4-carbonyl chloride, and 6-quinolinamine the title compound was obtained in 88% purity by LC/MS. MS(ESI+): m/z=434.2.

Example 117

(2S,4EZ)-N-cyclopropyl-4-{[(3,4-dichlorobenzyl)oxy]imino}-1-(diphenylacetyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, diphenylacetyl chloride, and cyclopropylamine the title compound was obtained in 49% purity by LC/MS. MS(ESI+): m/z=536.6.

Example 118

(2S,4EZ)-1-(4-cyanobenzoyl)-4-{[(3,4-dichlorobenzyl)oxy]imino}-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-cyanobenzoyl chloride, and 6-quinolinamine the title compound was obtained in 52% purity by LC/MS. MS(ESI+): m/z=558.6.

Example 119

(2S)-4-oxo-1-(phenoxyacetyl)-N-[2-(1H-pyrrol-1-yl)phenyl]-2-pyrrolidinecarbox-amide Following the general method as outlined in Example 22, starting from 1-(tert-butoxycarbonyl)-4-oxoproline, phenoxyacetyl chloride, and 2-(1H-pyrrol-1-yl)phenylamine the title compound was obtained in 42% purity by LC/MS. MS(ESI+): m/z=404.2.

Example 120

(2S,4EZ)-N-cyclopropyl-4-{[(3,4-dichlorobenzyl) oxy]imino}-1-(methoxyacetyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, methoxyacetyl chloride, and cyclopropylamine the title compound was obtained in 54% purity by LC/MS. MS(ESI+): m/z=414.6.

Example 121

(2S,4EZ)-N-(1,3-benzodioxol-5-ylmethyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-carbonyl chloride, and 1,3-benzodioxol-5-ylmethylamine the title compound was obtained in 64% purity by LC/MS. MS(ESI+): m/z=472.4.

Example 122

(3EZ,5S)-5-[(4-acetyl-1-piperazinyl)carbonyl]-1-acryloyl-3-pyrrolidinone O-(3,4-dichlorobenzyl) oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acryloyl chloride, and 1-acetylpiperazine the title compound was obtained in 79% purity by LC/MS. MS(ESI+): m/z=467.6.

Example 123

(2S)-1-([1,1'-biphenyl]-4-ylcarbonyl)-N-(2-furylmethyl)-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 2-furylmethylamine the title compound was obtained in 94% purity by LC/MS. MS(ESI+): m/z=387.2.

Example 124

(2S,4EZ)-4-(cyanomethylene)-N-(3,4-dimethoxybenzyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 2-oxo-6-pentyl-2H-pyran-3-yl)carbonyl chloride, and 3,4-dimethoxybenzylamine the title compound was obtained in 65% purity by LC/MS. MS(ESI+): m/z=494.4.

Example 125

(2S,4EZ)-1-[(benzoylamino)carbonyl]-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, benzoyl isocyanate, and 9-ethyl-9H-carbazol-3-amine the title compound was obtained in 74% purity by LC/MS. MS(ESI+): m/z=492.4.

Example 126

(2S,4EZ)-1-benzoyl-N-[2-(diethylamino)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, benzoyl chloride, and N1,N1-diethyl-1,2-ethanediamine the title compound was obtained in 80% purity by LC/MS. MS(ESI+): m/z=361.2.

Example 127

(2S,4EZ)-N-[2-(diethylamino)ethyl]-1-(diphenylacetyl)-4-(ethoxyimino)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, diphenylacetyl chloride, and N1,N1-diethyl-1,2-ethanediamine the title compound was obtained in 50% purity by LC/MS. MS(ESI+): m/z=465.4.

Example 128

(2S,4EZ)-N-(2,1,3-benzothiadiazol-4-yl)-4-[(benzyloxy)imino]-1-(4-cyanobenzoyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 2,1,3-benzothiadiazol-4-amine the title compound was obtained in 55% purity by LC/MS. MS(ESI+): m/z=497.4.

Example 129

(2EZ)-[5-(1H-benzimidazol-2-yl)-1-([1,1'-biphenyl]-4-ylcarbonyl)-3-pyrrolidinylidene]ethanenitrile Following the general method as outlined in Example 22, starting from (2S,4EZ)-1-(tert-butoxycarbonyl)-4-(cyanomethylene)-2-pyrrolidinecarboxylic acid, [1,1'-biphenyl]4-carbonyl chloride, and 1,2-benzenediamine the title compound was obtained in 70% purity by LC/MS. MS(ESI+): m/z=405.2.

Example 130

(2S,4EZ)-4-(chloromethylene)-N-(9-ethyl-9H-carbazol-3-yl)-1-(phenoxyacetyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, phenoxyacetyl chloride, and 9-ethyl-9H-carbazol-3-amine the title compound was obtained in 63% purity by LC/MS. MS(ESI+): m/z=488.6.

Example 131

(2S)-$N^2$-(9-ethyl-9H-carbazol-3-yl)-$N^1$-(3-methoxyphenyl)-4-methylene-1,2-pyrrolidinedicarboxamide Following the general method as outlined in Example 22, starting from 1-(tert-butoxycarbonyl)-4-methyleneproline, 1-isocyanato-3-methoxybenzene, and 9-ethyl-9H-carbazol-3-amine the title compound was obtained in 47% purity by LC/MS. MS(ESI+): m/z=469.4.

Example 132

(2S,4EZ)-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, and 9-ethyl-9H-carbazol-3-amine the title compound was obtained in 36% purity by LC/MS. MS(ESI+): m/z=345.2.

Example 133

(2S,4EZ)-1-(4-cyanobenzoyl)-N-[2-(diethylamino)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-cyanobenzoyl chloride, and N1,N1-diethyl-1,2-ethanediamine the title compound was obtained in 58% purity by LC/MS. MS(ESI+): m/z=386.2.

Example 134

4-{[(2S,4EZ)-2-(1H-benzimidazol-2-yl)-4-(cyanomethylene)pyrrolidinyl]carbonyl}benzonitrile Following the general method as outlined in Example 22, starting from (2S,4EZ)-1-(tert-butoxycarbonyl)-4-(cyanomethylene)-2-pyrrolidinecarboxylic acid, 4-cyanobenzoyl chloride, and 1,2-benzenediamine the title compound was obtained in 84% purity by LC/MS. MS(ESI+): m/z=354.2.

Example 135

(2S,4EZ)-4-[(allyloxy)imino]-1-[4-(dimethylamino)butanoyl]-N-(9-ethyl-9H-carbazol-3-yl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-(dimethylamino)butanoyl chloride, and 9-ethyl-9H-carbazol-3-amine the title compound was obtained in 40% purity by LC/MS. MS(ESI+): m/z=490.4.

Example 136

(2S,4EZ)-4-benzylidene-N-(9-ethyl-9H-carbazol-3-yl)-2-pyrrolidinecarboxamide

Following the general method as outlined in Example 22, starting from (2S,4EZ)-4-benzylidene-1-(tert-butoxycarbonyl)-2-pyrrolidinecarboxylic acid, and 9-ethyl-9H-carbazol-3-amine the title compound was obtained in 53% purity by LC/MS. MS(ESI+): m/z=396.2.

Example 137

(2S,4EZ)-4-benzylidene-1-[4-(dimethylamino)butanoyl]-N-(9-ethyl-9H-carbazol-3-yl)-2-pyrrolidinecarboxamide Following the general method as outlined in Example 22, starting from (2S,4EZ)-4-benzylidene-1-(tert-butoxycarbonyl)-2-pyrrolidinecarboxylic acid, 4-(dimethylamino)butanoyl chloride, and 9-ethyl-9H-carbazol-3-amine the title compound was obtained in 74% purity by LC/S. MS(ESI+): m/z=509.4.

Example 138

(2S,4EZ)-4-(chloromethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, and 9-ethyl-9H-carbazol-3-amine the title compound was obtained in 73% purity by LC/MS. MS(ESI+): m/z=354.4.

Example 139

(2S)-N-(9-ethyl-9H-carbazol-3-yl)-4-methylene-2-pyrrolidinecarboxamide

Following the general method as outlined in Example 22, starting from 1-(tert-butoxycarbonyl)-4-methyleneproline, and 9-ethyl-9H-carbazol-3-amine the title compound was obtained in 71% purity by LC/MS. MS(ESI+): m/z=320.2.

Example 140

(2S,4EZ)-4-(cyanomethylene)-N-(9-ethyl-9H-carbazol-3-yl)-1-(4-phenoxybenzoyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 4-phenoxybenzoyl chlo-ride, and 9-ethyl-9H-carbazol-3-amine the title compound was obtained in 37% purity by LC/MS. MS(ESI+): m/z=541.4.

Example 141

N-{[(2S,4EZ)-2-(1H-benzimidazol-2-yl)-4-(chloromethylene)pyrrolidinyl]carbon}benzamide Following the general method as outlined in Example 22, starting from (2S,4EZ)-1-(tert-butoxycarbonyl)-4-(chloromethylene)-2-pyrrolidinecarboxylic acid, benzoyl isocyanate, and 1,2-benzenediamine the title compound was obtained in 51% purity by LC/MS. MS(ESI+): m/z=381.4.

Example 142

(2S)-$N^1$-(3,5-dichlorophenyl)-$N^2$-(9-ethyl-9H-carbazol-3-yl)-4-methylene-1,2-pyrrolidinedicarboxamide Following the general method as outlined in Example 22, starting from 1-(tert-butoxycarbonyl)-4-methyleneproline, 1,3-dichloro-5-isocyanatobenzene, and 9-ethyl-9H-carbazol-3-amine the title compound was obtained in 40% purity by LC/MS. MS(ESI+): m/z=507.6.

Example 143

(2S)-1-(diphenylacetyl)-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, diphenylacetyl chloride, and 9-ethyl-9H-carbazol-3-amine the title compound was obtained in 42% purity by LC/MS. MS(ESI+): m/z=514.4.

Example 144

(2S,4EZ)-1-benzoyl-4-(chloromethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and 9-ethyl-9H-carbazol-3-amine the title compound was obtained in 48% purity by LC/MS. MS(ESI+): m/z=458.4.

Example 145

(2S,4EZ)-1-([1,1'-biphenyl]-4-ylcarbonyl)-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, [1,1'-biphenyl]-4-carbonyl chloride, and 9-ethyl-9H-carbazol-3-amine the title compound was obtained in 32% purity by LC/MS. MS(ESI+): m/z=525.4.

Example 146

(2S,4EZ)-4-(cyanomethylene)-N-(9-ethyl-9H-carbazol-3-yl)-1-(3-oxobutyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 3-buten-2-one, and 9-ethyl-9H-carbazol-3-amine the title compound was obtained in 59% purity by LC/MS. MS(ESI+): m/z=415.2.

Example 147

(2S)-1-[(4-chlorophenoxy)acetyl]-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, (4-chlorophenoxy)acetyl chloride, and 9-ethyl-9H-carbazol-3-amine the title compound was obtained in 100% purity by LC/MS. MS(ESI+): m/z=488.4.

Example 148

(2S)-1-([1,1'-biphenyl]-4-ylcarbonyl)-N-(9-ethyl-9H-carbazol-3-yl)-4-methylene-2-pyrrolidinecarboxamide Following the general method as outlined in Example 22, staring from 1-(tert-butoxycarbonyl)-4-methyleneproline, [1,1'-biphenyl]-4-carbonyl chloride, and 9-ethyl-9H-carbazol-3-amine the title compound was obtained in 46% purity by LC/MS. MS(ESI+): m/z=500.4.

Example 149

2-[(2S,4EZ)-4-(chloromethylene),prolidinyl]-1H-benzimidazole

Following the general method as outlined in Example 22, starting from (2S,4EZ)-1-(tert-butoxycarbonyl)-4-(chloromethylene)-2-pyrrolidinecarboxylic acid, and 1,2-benzenediamine the title compound was obtained in 43% purity by LC/MS. MS(ESI+): m/z=234.4.

Example 150

(2S,4EZ-4-(ethoxyimino)-N-(9-ethyl-9H-carbazol-3-yl)-2-pyrrolidinecarboxamide

Following the general method as outlined in Example 22, starting from (2S,4EZ)-1-(tert-butoxycarbonyl)-4-(ethoxyimino)-2-pyrrolidinecarboxylic acid, and 9-ethyl-9H-carbazol-3-amine the title compound was obtained in 91% purity by LC/MS. MS(ESI+): m/z=365.2.

Example 151

(2S)-1-benzoyl-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, benzoyl chloride, and 9-ethyl-9H-carbazol-3-amine the title compound was obtained in 52% purity by LC/MS. MS(ESI+): m/z=424.2.

Example 152

(2S,4EZ)-N-[2-(diethylamino)ethyl]-1-(diphenylacetyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and N1,N1-diethyl-1,2-ethanediamine the title compound was obtained in 56% purity by LC/MS. MS(ESI+): m/z=557.4.

Example 144153

(2S,4EZ)-1-benzoyl-N-(2-furylmethyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, benzoyl chloride, and 2-furylmethylamine the title compound was obtained in 40% purity by LC/MS. MS(ESI+): m/z=448.2.

Example 154

(2S,4EZ)-4-(tert-butoxyimino)-N-[2-(diethylamino)ethyl]-1-(diphenylacetyl)-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, diphenylacetyl chloride, and N1,N1-diethyl-1,2-ethanediamine the title compound was obtained in 80% purity by LC/MS. MS(ESI+): m/z=493.4.

Example 155

(2S)-1-([1,1'-biphenyl]-4-ylcarbonyl)-N-(3,4-dimethoxybenzyl)-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 3,4-dimethoxybenzylamine the title compound was obtained in 72% purity by LC/MS. MS(ESI+): m/z=457.2.

Example 156

(2S,4EZ)-4-(cyanomethylene)-$N^1$-(3,5-dichlorophenyl)-$N^2$-(9-ethyl-9H-carbazol-3-yl)-1,2-pyrrolidinedicarboxamide Following the general method as outlined in Example 22, starting from (2S,4EZ)-1-(tert-butoxycarbonyl)-4-(cyanomethylene)-2-pyrrolidinecarboxylic acid, 1,3-dichloro-5-isocyanatobenzene, and 9-ethyl-9H-carbazol-3-amine the title compound was obtained in 60% purity by LC/MS. MS(ESI+): m/z=532.8.

Example 157

(2S,4EZ)-4-[(allyloxy)imino]-$N^2$-(9-ethyl-9H-carbazol-3-yl)-$N^1$-phenyl-1,2-pyrrolidinedicarboxamide Following the general method as outlined in Example 22, starting from (2S,4EZ)-4-[(allyloxy)-imino]-1-(tert-butoxycarbonyl)-2-pyrrolidinecarboxylic acid, isocyanatobenzene, and 9-ethyl-9H-carbazol-3-amine the title compound was obtained in 67% purity by LC/MS. MS(ESI+): m/z=496.4.

Example 158

(2S)-$N^2$-(9-ethyl-9H-carbazol-3-yl)-4-methylene-$N^1$-phenyl-1,2-pyrrolidinedicar-boxamide Following the general method as outlined in Example 22, starting from 1-(tert-butoxycarbonyl)-4-methyleneproline, isocyanatobenzene, and 9-ethyl-9H-carbazol-3-amine the title compound was obtained in 66% purity by LC/MS. MS(ESI+): m/z=439.2.

Example 159

(2S,4EZ)-$N^2$-(2,1,3-benzothiadiazol-4-yl)-$N^1$-(3,5-dichlorophenyl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1,3-dichloro-5-isocyanatobenzene, and 2,1,3-benzothiadiazol-4-amine the title compound was obtained in 55% purity by LC/MS. MS(ESI+): m/z=479.6.

Example 160

(2EZ)-[5-(1H-benzimidazol-2-yl)-1-(4-phenoxybenzoyl)-3-pyrrolidinyldene]ethanenitrile Following the general method as outlined in Example 22, starting from (2S,4EZ)-1-(tert-butoxycarbonyl)-4-(cyanomethylene)-2-pyrrolidinecarboxylic acid, 4-phenoxybenzoyl chloride, and 1,2-benzenediamine the title compound was obtained in 90% purity by LC/MS. MS(ESI+): m/z=421.2.

Example 161

(2S,4EZ)-4-(tert-butoxyimino)-1-(2-ethoxy-1-naphthoyl)-N-(9-ethyl-9H-carbazol-3-yl)-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-ethoxy-1-naphthoyl chloride, and 9-ethyl-9H-carbazol-3-amine the title compound was obtained in 47% purity by LC/MS. MS(ESI+): m/z=591.4.

Example 162

(2S,4EZ)-1-benzoyl-N-[2-(diethylamino)ethyl]-4-(ethoxyimino)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, benzoyl chloride, and N1,N1-diethyl-1,2-ethanediamine the title compound was obtained in 84% purity by LC/MS. MS(ESI+): m/z=375.2.

Example 163

(2S,4EZ)-$N^2$-(2,1,3-benzothiadiazol-4-yl)-4-[(benzyloxy)imino]-$N^1$-phenyl-1,2-pyrrolidinedicarboxamide Following the general method as outlined in Example 22, starting from (2S,4EZ)-4-[(benzyloxy)imino]-1-(tert-butoxycarbonyl)-2-pyrrolidinecarboxylic acid, isocyanatobenzene, and 2,1,3-benzothiadiazol-4-amine the title compound was obtained in 57% purity by LC/MS. MS(ESI+): m/z=487.4.

Example 164

(2S,4EZ)-1-(4-cyanobenzoyl)-4-{[(3,4dichlorobenzyl)oxy]imino}-N-(1-naphthylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-cyanobenzoyl chloride, and 1-naphthylmethylamine the title compound was obtained in 39% purity by LC/MS. MS(ESI+): m/z=571.6.

Example 165

(2S,4EZ)-N-(2,1,3-benzothiadiazol-4-yl)-1-benzoyl-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, benzoyl chloride, and 2,1,3-benzothiadiazol-4-amine the title compound was obtained in 61% purity by LC/MS. MS(ESI+): m/z=502.4.

Example 166

(2S,4EZ)-4-[(allyloxy)imino]-N-(2,1,3-benzothiadiazol-4-yl)-1-(diphenylacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 2,1,3-benzothiadiazol-4-amine the title compound was obtained in 46% purity by LC/MS. MS(ESI+): m/z=512.4.

Example 167

(2S,4EZ)-4(ethoxyimino)-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and 9-ethyl-9H-carbazol-3-amine the title compound was obtained in 75% purity by LC/MS. MS(ESI+): m/z=557.4.

Example 168

(2S,4EZ)-1-benzoyl-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, benzoyl chloride, and 9-ethyl-9H-carbazol-3-amine the title compound was obtained in 74% purity by LC/MS. MS(ESI+): m/z=469.4.

Example 169

(2S,4EZ)-4-(ethoxyimino)-N-(9-ethyl-9H-carbazol-3-yl)-1-(methoxyacetyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, methoxyacetyl chloride, and 9-ethyl-9H-carbazol-3-amine the title compound was obtained in 88% purity by LC/MS. MS(ESI+): m/z=437.2.

Example 170

(2S,4EZ)-4-[(benzyloxy)imino]-N$^2$-(9-ethyl-9H-carbazol-3-yl)-N$^1$-pentyl-1,2-pyrrolidinedicarboxamide Following the general method as outlined in Example 22, starting from (2S,4EZ)-4-[(benzyloxy)imino]-1-(tert-butoxycarbonyl)-2-pyrrolidinecarboxylic acid, 1-isocyanatopentane, and 9-ethyl-9H-carbazol-3-amine the title compound was obtained in 63% purity by LC/MS. MS(ESI+): m/z=540.4.

Example 171

(3EZ,5S)-1-benzoyl-5-{[4-(3,4-dichlorophenyl)-1-piperazinyl]carbonyl}-3-pyrrolidinone O-ethyloxime Following the general method as outlined in Example 22, starting from (2S,4EZ)-1-(tert-butoxycarbonyl)-4-(ethoxyimino)-2-pyrrolidinecarboxylic acid, benzoyl chloride, and 1-(3,4-dichlorophenyl)piperazine the title compound was obtained in 51% purity by LC/MS. MS(ESI+): m/z=489.6.

Example 172

(2S,4EZ)-4-[(allyloxy)imino]-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 48% purity by LC/MS. MS(ESI+): m/z=569.4.

Example 173

(2S,4EZ)-4-{[(4-methoxybenzyl)oxy]imino}-N-(2-methoxyethyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, and 2-methoxyethylamine the title compound was obtained in 52% purity by LC/MS. MS(ESI+): m/z=322.2.

Example 174

(2S,4EZ)-4-[(allyloxy)imino]-N-(3,4-dimethoxybenzyl)-1-(diphenylacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 3,4-dimethoxybenzylamine the title compound was obtained in 63% purity by LC/MS. MS(ESI+): m/z=528.4.

Example 175

(2S,4EZ)-4-[(allyloxy)imino]-1-(4-cyanobenzoyl)-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-cyanobenzoyl chloride, and 9-ethyl-9H-carbazol-3-amine the title compound was obtained in 43% purity by LC/MS. MS(ESI+): m/z=506.4.

Example 176

(2S,4EZ)-4-{[(4-methoxybenzyl)oxy]imino}-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 2-oxo-6-pentyl-2H-pyran-3-carbonyl chloride, and 6-quinolinamine the title compound was obtained in 61% purity by LC/MS. MS(ESI+): m/z=583.4.

Example 177

(2S,4EZ)-N-(9-ethyl-9H-carbazol-3-yl)-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, and 9-ethyl-9H-carbazol-3-amine the title compound was obtained in 46% purity by LC/MS. MS(ESI+): m/z=351.2.

Example 178

(2S,4EZ)-$N^2$-(9-ethyl-9H-carbazol-3-yl)-4-(methoxyimino)-$N^1$-(3-methoxyphenyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methoxybenzene, and 9-ethyl-9H-carbazol-3-amine the title compound was obtained in 100% purity by LC/MS. MS(ESI+): m/z=500.4.

Example 179

(2S,4EZ)-4-(ethoxyimino)-$N^2$-(9-ethyl-9H-carbazol-3-yl)-$N^1$-(3-methoxyphenyl)-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1-isocyanato-3-methoxybenzene, and 9-ethyl-9H-carbazol-3-amine the title compound was obtained in 60% purity by LC/MS. MS(ESI+): m/z=514.4.

Example 180

(2S,4EZ)-1-[(4-chlorophenoxy)acetyl]-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, (4-chlorophenoxy)acetyl chloride, and 9-ethyl-9H-carbazol-3-amine the title compound was obtained in 100% purity by LC/MS. MS(ESI+): m/z=533.4.

Example 181

(2S,4EZ)-4-[(allyloxy)imino]-N-(9-ethyl-9H-carbazol-3-yl)-1-(4-phenoxybenzoyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-phenoxybenzoyl chloride, and 9-ethyl-9H-carbazol-3-amine the title compound was obtained in 63% purity by LC/MS. MS(ESI+): m/z=573.4.

Example 182

(2S,4EZ)-$N^1$-benzoyl-$N^2$-(9-ethyl-9H-carbazol-3-yl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, benzoyl isocyanate, and 9-ethyl-9H-carbazol-3-amine the title compound was obtained in 59% purity by LC/MS. MS(ESI+): m/z=498.4.

Example 183

(2S,4EZ)-4-[(benzyloxy)imino]-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 93% purity by LC/MS. MS(ESI+): m/z=619.6.

Example 184

(2S,4EZ)-1-acetyl-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, acetyl chloride, and 9-ethyl-9H-carbazol-3-amine the title compound was obtained in 87% purity by LC/MS. MS(ESI+): m/z=407.2.

Example 185

(2S,4EZ)-1-([1,1'-biphenyl]-4-ylcarbonyl)-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, [1,1'-biphenyl]-4-carbonyl chloride, and 9-ethyl-9H-carbazol-3-amine the title compound was obtained in 70% purity by LC/MS. MS(ESI+): m/z=545.4.

Example 186

(2S,4EZ)-1-acetyl-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, acetyl chloride, and 9-ethyl-9H-carbazol-3-amine the title compound was obtained in 69% purity by LC/MS. MS(ESI+): m/z=393.2.

Example 187

(2S,4EZ)-1-(diphenylacetyl)-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 9-ethyl-9H-carbazol-3-amine the title compound was obtained in 77% purity by LC/MS. MS(ESI+): m/z=545.4.

Example 188

(2S,4EZ)-4-[(allyloxyimino]-$N^1$-benzoyl-$N^2$-(9-ethyl-9H-carbazol-3-al)-1,2-pyrrolidinedicarboxamide Following the general method as outlined in Example 22, starting from (2S,4EZ)-4-[(allyloxy)imino]-1-(tert-butoxycarbonyl)-2-pyrrolidinecarboxylic acid, benzoyl isocyanate, and 9-ethyl-9H-carbazol-3-amine the title compound was obtained in 63% purity by LC/MS. MS(ESI+): m/z=524.4.

Example 189

(2S,4EZ)-$N^2$-(9-ethyl-9H-carbazol-3-yl)-4-(methoxyimino)-$N^1$-(3-methylphenyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methylbenzene, and 9-ethyl-9H-carbazol-3-amine the title compound was obtained in 89% purity by LC/MS. MS(ESI+): m/z=484.4.

Example 190

(2S,4EZ)-4-{[(4-methoxybenzyl)oxy]imino}-$N^1$-pentyl-$N^2$-(2-thienylmethyl)-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and 2-thienylmethylamine the title compound was obtained in 86% purity by LC/MS. MS(ESI+): m/z=473.2.

Example 191

(2S,4EZ)-4-(ethoxyimino)-1-(methoxyacetyl)-N-(6-quinolinyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, methoxyacetyl chloride, and 6-quinolinamine the title compound was obtained in 81% purity by LC/MS. MS(ESI+): m/z=371.2.

Example 192

(2S,4EZ)-4-[(allyloxy)imino]-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, and 9-ethyl-9H-carbazol-3-amine the title compound was obtained in 80% purity by LC/MS. MS(ESI+): m/z=377.2.

Example 193

(2S,4EZ)-4-[(benzyloxy)imino]-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 6-quinolinamine the title compound was obtained in 48% purity by LC/MS. MS(ESI+): m/z=553.4.

Example 194

(2S,4EZ)-4-[(allyloxy)imino]-N-[2-(diethylamino)ethyl]-2-pyrrolidinecarboxamide

Following the general method as outlined in Example 22, starting from (2S,4EZ)-4-[(allyloxy)-imino]-1-(tert-butoxycarbonyl)-2-pyrrolidinecarboxylic acid, and N1,N1-diethyl-1,2-ethanediamine the title compound was obtained in 78% purity by LC/MS. MS(ESI+): m/z=283.0.

Example 195

(2S,4EZ)-1-[4-(dimethylamino)butanoyl]-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(dimethylamino)-butanoyl chloride, and 9-ethyl-9H-carbazol-3-amine the title compound was obtained in 42% purity by LC/MS. MS(ESI+): m/z=464.2.

Example 196

(2S)-2-[(3-hydroxy-1-azetidinyl)carbonyl]-N-(3-methoxyphenyl)-4-oxo-1-pyrrolidinecarboxamide Following the general method as outlined in Example 22, starting from 1-(tert-butoxycarbonyl)-4-oxoproline, 1-isocyanato-3-methoxybenzene, and 3-azetidinol the title compound was obtained in 87% purity by LC/MS. MS(ESI+): m/z=334.2.

Example 197

(2S,4EZ)-4-[(benzyloxy)imino]-N-(9-ethyl-9H-carbazol-3-yl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and 9-ethyl-9H-carbazol-3-amine the title compound was obtained in 65% purity by LC/MS. MS(ESI+): m/z=561.4.

Example 198

(2S)-N-(9-ethyl-9H-carbazol-3-yl)-4-methylene-1-[(2-oxo-6-pentyl-2H-pyran-3-yl)carbonyl]-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and 9-ethyl-9H-carbazol-3-amine the title compound was obtained in 70% purity by LC/MS. MS(ESI+): m/z=512.4.

Example 199

(2S,4EZ)-N-(9-ethyl-9H-carbazol-3-yl)-1-(methoxyacetyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, methoxyacetyl chloride, and 9-ethyl-9H-carbazol-3-amine the title compound was obtained in 73% purity by LC/MS. MS(ESI+): m/z=423.4.

Example 200

(2S,4EZ)-$N^2$-(9-ethyl-9H-carbazol-3-yl)-4-(methoxyimino)-$N^1$-pentyl-1,2-pyrrolidinedicarboxamide Following the general method as outlined in Example 22, starting from (2S,4E)-1-(tert-butoxycarbonyl)-4-(methoxyimino)-2-pyrrolidinecarboxylic acid, 1-isocyanatopentane, and 9-ethyl-9H-carbazol-3-amine the title compound was obtained in 81% purity by LC/MS. MS(ESI+): m/z=464.2.

Example 201

(2S,4EZ)-4-(ethoxyimino)-$N^1$-pentyl-$N^2$-[2-(1H-pyrrol-1-yl)phenyl]-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1-isocyanatopentane, and 2-(1H-pyrrol-1-yl)phenylamine the title compound was obtained in 83% purity by LC/MS. MS(ESI+): m/z=426.2.

Example 202

(2S,4EZ)-4-[(allyloxy)imino]-N-(2-methoxyethyl)-2-pyrrolidinecarboxamide

Following the general method as outlined in Example 22, starting from (2S,4EZ)-4-[(allyloxy)-imino]-1-(tert-butoxycarbonyl)-2-pyrrolidinecarboxylic acid, and 2-methoxyethylamine the title compound was obtained in 100% purity by LC/MS. MS(ESI+): m/z=242.0.

Example 203

(2S,4EZ)-4-(tert-butoxyimino)-$N^2$-(2-methoxyethyl)-$N^1$-(3-methoxyphenyl)-1,2-pyrrolidinedicarboxamide Following the general method as outlined in Example 22, starting from (2S,4EZ)-1-(tert-butoxycarbonyl)-4-(tert-butoxyimino)-2-pyrrolidinecarboxylic acid, 1-isocyanato-3-methoxybenzene, and 2-methoxyethylamine the title compound was obtained in 76% purity by LC/MS. MS(ESI+): m/z=407.2.

Example 204

(2S,4EZ)-4-[(allyloxy)imino]-$N^2$-(2-methoxyethyl)-$N^1$-(3-methylphenyl)-1,2-pyrrolidinedicarboxamide Following the general method as outlined in Example 22, starting from (2S,4EZ)-4-[(allyloxy)-imino]-1-(tert-butoxycarbonyl)-2-pyrrolidinecarboxylic acid, 1-isocyanato-3-methylben-zene, and 2-methoxyethylamine the title compound was obtained in 85% purity by LC/MS. MS(ESI+): m/z=375.2.

Example 205

(2S,4EZ)-1-benzoyl-4-benzylidene-N-(9-ethyl-9H-carbazol-3-yl)-2-pyrrolidinecarboxamide Following the general method as outlined in Example 22, starting from (2S,4EZ)-4-benzylidene-1-(tert-butoxycarbonyl)-2-pyrrolidinecarboxylic acid, benzoyl chloride, and 9-ethyl-9H-carbazol-3-amine the title compound was obtained in 81% purity by LC/MS. MS(ESI+): m/z=500.4.

Example 206

(2S,4EZ)-$N^2$-benzyl-4-benzylidene-$N^2$-methyl-$N^1$-(3-methylphenyl)-1,2-pyrrolidinedicarboxamide Following the general method as outlined in Example 22, starting from (2S,4EZ)-4-benzylidene-1-(tert-butoxycarbonyl)-2-pyrrolidinecarboxylic acid, 1-isocyanato-3-methylbenzene, and N-benzyl-N-methylamine the title compound was obtained in 68% purity by LC/MS. MS(ESI+): m/z=440.2.

Example 207

(2S,4EZ)-4-(ethoxyimino)-N-(9-ethyl-9H-carbazol-3-yl)-1-(4-phenoxybenzoyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 4-phenoxybenzoyl chloride, and 9-ethyl-9H-carbazol-3-amine the title compound was obtained in 99% purity by LC/MS. MS(ESI+): m/z=561.4.

Example 208

(2S,4EZ)-4-(ethoxyimino)-$N^2$-(9-ethyl-9H-carbazol-3-yl)-$N^1$-(3-methylphenyl)-1,2-pyrrolidinedicarboxamide Following the general method as outlined in Example 22, staring from (2S,4EZ)-1-(tert-butoxycarbonyl)-4-(ethoxyimino)-2-pyrrolidinecarboxylic acid, 1-isocyanato-3-methylben-zene, and 9-ethyl-9H-carbazol-3-amine the title compound was obtained in 80% purity by LC/MS. MS(ESI+): m/z=498.4.

Example 209

(2S,4EZ)-4-(methoxyimino)-1-(phenoxyacetyl)-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, phenoxyacetyl chloride, and 6-quinolinamine the title compound was obtained in 100% purity by LC/MS. MS(ESI+): m/z=419.2.

Example 210

(2S,4EZ)-4-(tert-butoxyimino)-N-(34-dimethoxybenzyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 3,4-dimethoxybenzylamine the title compound was obtained in 63% purity by LC/MS. MS(ESI+): m/z=542.4.

Example 211

(2S,4EZ)-4-(tert-butoxyimino)-N-cyclopropyl-1-(phenoxyacetyl)-2pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, phenoxyacetyl chloride, and cyclopropylamine the title compound was obtained in 73% purity by LC/MS. MS(ESI+): m/z=374.2.

Example 212

(2S,4EZ)-4-[(benzyloxy)imino]-N-(tert-butyl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and tert-butylamine the title compound was obtained in 100% purity by LC/MS. MS(ESI+): m/z=424.2.

Example 213

(2S,4EZ)-N-(4,6-dimethoxy-2-pyrimidinyl)-4-(ethoxyimino-1-(4-phenoxybenzoyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 4-phenoxybenzoyl chloride, and 4,6-dimethoxy-2-pyrimidinamine the title compound was obtained in 79% purity by LC/MS. MS(ESI+): m/z=506.4.

Example 214

(4ZE)-4-[(allyloxy)imino]-N-(9-ethyl-9H-carbazol-3-)yl-1-(phenoxyacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, phenoxyacetyl chloride, and 9-ethyl-9H-carbazol-3-amine the title compound was obtained in 63% purity by LC/MS. MS(ESI+): m/z=511.4.

Example 215

(2S,4EZ)-1-([1,1'-biphenyl]-4-ylcarbonyl)-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 9-ethyl-9H-carbazol-3-amine the title compound was obtained in 66% purity by LC/MS. MS(ESI+): m/z=531.4.

Example 216

(3EZ,5S)-1-[4-(dimethylamino)butanoyl]-5-(1-piperidinylcarbonyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4(dimethylamino)butanoyl chloride, and piperidine the title compound was obtained in 100% purity by LC/MS. MS(ESI+): m/z=339.2.

Example 217

(2S,4EZ)-1-acetoacetyl-N-(9-ethyl-9H-carbazol-3-yl)4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 9-ethyl-9H-carbazol-3-amine the title compound was obtained in 42% purity by LC/MS. MS(ESI+): m/z=435.2.

Example 218

(2S,4EZ)-4-(methoxyimino)-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-oxo-6-pentyl-2H-pyran-3-carbonyl chloride, and 6-quinolinamine the title compound was obtained in 57% purity by LC/MS. MS(ESI+): m/z=477.2.

Example 219

(2S,4EZ)-N-(9-ethyl-9H-carbazol-3-yl)-4-{[(4-methoxybenzyl)oxy]imino}-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 2-oxo-6-pentyl-2H-pyran-3-carbonyl chloride, and 9-ethyl-9H-carbazol-3-amine the title compound was obtained in 57% purity by LC/MS. MS(ESI+): m/z=649.4.

Example 220

(2S,4EZ)-$N^2$-allyl-$N^1$-benzoyl-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, benzoyl isocyanate, and allylamine the title compound was obtained in 49% purity by LC/MS. MS(ESI+): m/z=345.0.

Example 221

(2S,4EZ)-4-[(benzyloxy)imino]-N-(9-ethyl-9H-carbazol-3-yl)-1-(methoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, methoxyacetyl chloride, and 9-ethyl-9H-carbazol-3-amine the title compound was obtained in 46% purity by LC/MS. MS(ESI+): m/z=499.2.

Example 222

(2S,4EZ)-$N^1$-(3,5-dichlorophenyl)-$N^2$-(9-ethyl-9H-carbazol-3-yl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1,3-dichloro-5-isocyanatobenzene, and 9-ethyl-9H-carbazol-3-amine the title compound was obtained in 42% purity by LC/MS. MS(ESI+): m/z=538.2.

Example 223

(2S,4EZ)-N-(9-ethyl-9H-carbazol-3-yl)-4-(methoxyimino)-1-(4-phenoxybenzoyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-phenoxybenzoyl chloride, and 9-ethyl-9H-carbazol-3-amine the title compound was obtained in 43% purity by LC/MS. MS(ESI+): m/z=547.2.

Example 224

(2S,4EZ)-$N^1$-(3,5-dichlorophenyl)-4-(ethoxyimino)-$N^2$-(9-ethyl-9H-carbazol-3-yl)-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1,3-dichloro-5-isocyanatobenzene, and 9-ethyl-9H-carbazol-3-amine the title compound was obtained in 43% purity by LC/MS. MS(ESI+): m/z=552.6.

Example 225

(3EZ,5S)-5-{[4-(1,3-benzodioxol-5-ylmethyl)-1-piperazinyl]carbonyl}-1-[(2-oxo-6-pentyl-2H-pyran-3-yl)carbonyl]-3-pyrrolidinone O-(tert-butyl)oxime Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 1-(1,3-benzodioxol-5-ylmethyl)piperazine the title compound was obtained in 59% purity by LC/MS. MS(ESI+): m/z=595.4.

Example 226

(2S,4EZ)-4-benzylidene-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-benzylidene-1-(tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 47% purity by LC/MS. MS(ESI+): m/z=588.4.

Example 227

(2S,4EZ)-4-[(allyloxy)imino]-1-benzoyl-N-(6-quinolinyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, benzoyl chloride, and 6-quinolinamine the title compound was obtained in 83% purity by LC/MS. MS(ESI+): m/z=415.2.

Example 228

(2S,4EZ)-4-[(allyloxy)imino]-1-(methoxyacetyl)-N-(6-quinolinyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, methoxyacetyl chloride, and 6-quinolinamine the title compound was obtained in 71% purity by LC/MS. MS(ESI+): m/z=383.0.

Example 229

(2S,4EZ)-4-[(allyloxy)imino]-N-ethyl-9H-carbazol-3-yl)-1-(methoxyacetyl)2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, methoxyacetyl chloride, and 9-ethyl-9H-carbazol-3-amine the title compound was obtained in 74% purity by LC/MS. MS(ESI+): m/z=449.2.

Example 230

(2S,4EZ)-4-[(allyloxy)imino]-1-(2-ethoxy-1-naphthoyl)-(9-ethyl-9H-carbazol-3-yl)-2-pyrrolidinecarboxamide Following the general method as outlined in Example 22, starting from (2S,4EZ)-$_4$-[(allyloxy)-imino]-1-(tert-butoxycarbonyl)-2-pyrrolidinecarboxylic acid, 2-ethoxy-1-naphthoyl chlo-ride, and 9-ethyl-9H-carbazol-3-amine the title compound was obtained in 60% purity by LC/MS. MS(ESI+): m/z=575.4.

Example 231

(2S,4EZ)-4-[(allyloxy)imino]-1-[(4-chlorophenoxy)acetyl]-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, (4-chlorophenoxy)acetyl chloride, and 9-ethyl-9H-carbazol-3-amine the title compound was obtained in 78% purity by LC/MS. MS(ESI+): m/z=545.4.

Example 232

(2S,4EZ)-4-[(allyloxy)imino]-1-([1,1'-biphenyl]-4-ylcarbonyl)-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, [1,1'-biphenyl]-4-carbonyl chloride, and 9-ethyl-9H-carbazol-3-amine the title compound was obtained in 51% purity by LC/MS. MS(ESI+): m/z=557.2.

Example 233

(2S,4EZ)-4-[(allyloxy)imino]-1-(diphenylacetyl)-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 9-ethyl-9H-carbazol-3-amine the title compound was obtained in 43% purity by LC/MS. MS(ESI+): m/z=571.2.

Example 234

(2S,4EZ)-1-([1,1'-biphenyl]-4-ylcarbonyl)-N-(tert-butyl)-4-(chloromethylene)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and tert-butylamine the title compound was obtained in 80% purity by LC/MS. MS(ESI+): m/z=397.6.

Example 235 tert-butyl 3-[({4-methylene-1-[(pentylamino)carbonyl]-2-pyrrolidinyl}carbonyl)amino]-1-azetidinecarboxylate Following the general method as outlined in Example 22, starting from 1-(tert-butoxycarbonyl)-4-methyleneproline, 1-isocyanatopentane, and tert-butyl 3-amino-1-azetidinecarboxylate the title compound was obtained in 75% purity by LC/MS. MS(ESI+): m/z=395.2.

Example 236

(3EZ,5S)-1-acetyl-5-[(4-acetyl-1-piperazinyl)carbonyl]-3-pyrrolidinone O-(3,4-dichlorobenzyl)oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and 1-acetylpiperazine the title compound was obtained in 85% purity by LC/MS. MS(ESI+): m/z=455.2.

Example 237

(2S,4EZ)-$N^2$-benzyl-4-(methoxyimino)-$N^1$-pentyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and benzylamine the title compound was obtained in 100% purity by LC/MS. MS(ESI+): m/z=361.0.

Example 238

(2S,4EZ)-1-acetyl-4-{[(3,4-dichlorobenzyl)oxy]
imino}-N-(1-naphthylmethyl)-2-pyrrolidinecarboxamide Following the general method as outlined in Example 22, starting from (2S,4EZ)-1-(tert-butoxycarbonyl)-4-{[(3,4dichlorobenzyl)oxy]imino}-2-pyrrolidinecarboxylic acid, acetyl chloride, and 1-naphthylmethylamine the title compound was obtained in 60% purity by LC/MS. MS(ESI+): m/z=484.2.

Example 239

(2S,4EZ)-4-(tert-butoxyimino)-N-cyclopropyl-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and cyclopropylamine the title compound was obtained in 75% purity by LC/MS. MS(ESI+): m/z=432.2.

Example 240

(2S,4EZ)-4-{[(4-methoxybenzyl)oxy]imino}-1-(4-phenoxybenzoyl)-N-[2-(1H-pyrrol-1-yl)phenyl]-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 4-phenoxybenzoyl chloride, and 2-(1H-pyrrol-1-yl)phenylamine the title compound was obtained in 55% purity by LC/MS. MS(ESI+): m/z=601.4.

Example 241

(2S)-N-(1,3-benzodioxol-5-ylmethyl)-4-oxo-2-pyrrolidinecarboxamide

Following the general method as outlined in Example 22, starting from 1-(tert-butoxycarbonyl)-4-oxoproline, and 1,3-benzodioxol-5-ylmethylamine the title compound was obtained in 71% purity by LC/MS. MS(ESI+): m/z=263.0.

Example 242

(2S,4EZ)-N-(1,3-benzodioxol-5-ylmethyl)-1-([1,1'-biphenyl]-4-ylcarbonyl)-4-(chloromethylene)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and 1,3-benzodioxol-5-ylmethylamine the title compound was obtained in 63% purity by LC/MS. MS(ESI+): m/z=475.6.

Example 243

(2S,4EZ)-N-(3,4-dimethoxybenzyl)-4-(ethoxyimino)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and 3,4-dimethoxybenzylamine the title compound was obtained in 41% purity by LC/MS. MS(ESI+): m/z=514.2.

Example 244

(2S)-2-[(3-hydroxy-1-azetidinyl)carbonyl]-N-(3-methylphenyl)-4-oxo-1-pyrrolidinecarboxamide Following the general method as outlined in Example 22, starting from 1-(tert-butoxycarbonyl)-4-oxoproline, 1-isocyanato-3-methylbenzene, and 3-azetidinol the title compound was obtained in 73% purity by LC/MS. MS(ESI+): m/z=318.0.

Example 245

(2S,4EZ)-4-[(benzyloxy)imino]-N-[(2RS)-2-hydroxy-2-phenethyl]-1-[(2-oxo-6-pentyl-2H-pyran-3-yl)carbonyl]-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and (1RS)-2-amino-1-phenylethanol the title compound was obtained in 55% purity by LC/MS. MS(ESI+): m/z=546.2.

Example 246

(2S,4EZ)-4-[(allyloxy)imino]-$N^2$-(3,4-dimethoxybenzyl)-$N^1$-(3-methoxyphenyl)-1,2-pyrrolidinedicarboxamide Following the general method as outlined in Example 22, starting from (2S,4EZ)-4-[(allyloxy)imino]-1-(tert-butoxycarbonyl)-2-pyrrolidinecarboxylic acid, 1-isocyanato-3-methoxybenzene, and 3,4-dimethoxybenzylamine the title compound was obtained in 97% purity by LC/MS. MS(ESI+): m/z=483.2.

Example 247

(2S,4EZ)-4-[(allyloxy)imino]-1-(4-cyanobenzoyl)-N-(2-methoxyethyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-cyanobenzoyl chloride, and 2-methoxyethylamine the title compound was obtained in 44% purity by LC/MS. MS(ESI+): m/z=371.0.

Example 248

(2S,4EZ)-N-benzyl-1-(methoxyacetyl)-4-{[(4-methoxybenzyl)oxy]imino}-2-pyrrolidine-carboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, methoxyacetyl chloride, and benzylamine the title compound was obtained in 49% purity by LC/MS. MS(ESI+): m/z=426.2.

Example 249

(2S,4EZ)-1-benzoyl-4-(chloromethylene)-N-(2-furylmethyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and 2-furylmethylamine the title compound was obtained in 73% purity by LC/MS. MS(ESI+): m/z=345.6.

Example 250

(2S)-1-acetyl-4-methylene-N-(6-quinolinyl)-2-pyrrolidinecarboxamide

Following the general method as outlined in Example 22, starting from 1-(tert-butoxycarbonyl)-4-methyleneproline, acetyl chloride, and 6-quinolinamine the title compound was obtained in 87% purity by LC/MS. MS(ESI+): m/z=296.0.

Example 251

(2S,4EZ)-1-acetyl-4-{[(3,4-dichlorobenzyl)oxy]imino}-N-(2-furylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and 2-furylmethylamine the title compound was obtained in 199% purity by LC/MS. MS(ESI+): m/z=424.6.

Example 252

(2S)-$N^1$-(3,5-dichlorophenyl)-4-methylene-$N^2$-(6-quinolinyl)-1,2-pyrrolidinedicar-boxamide Following the general method as outlined in Example 22, starting from 1-(tert-butoxy-carbonyl)-4-methyleneproline, 1,3-dichloro-5-isocyanatobenzene, and 6-quinolinamine the title compound was obtained in 65% purity by LC/MS. MS(ESI+): m/z=441.0.

Example 253

(3EZ,5S)-1-(diphenylacetyl)-5-(1-piperidinylcarbonyl)-3-pyrrolidinone O-(4-methoxybenzyl)oxime Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and piperidine the title compound was obtained in 87% purity by LC/MS. MS(ESI+): m/z=526.4.

Example 254

(2S,4EZ)-4-(chloromethylene)-N-(1-naphthylmethyl)-1-(phenoxyacetyl)-2-pyrrolidine-carboxamide Following the general method as outlined in Example 22, starting from (2S,4EZ)-1-(tert-butoxycarbonyl)-4-(chloromethylene)-2-pyrrolidinecarboxylic acid, phenoxyacetyl chloride, and 1-naphthylmethylamine the title compound was obtained in 75% purity by LC/MS. MS(ESI+): m/z=435.6.

Example 255

(2S,4EZ)-4-[(allyloxy)imino]-N-benzoyl-2-(4-morpholinylcarbonyl)-1-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, benzoyl isocyanate, and morpholine the title compound was obtained in 46% purity by LC/MS. MS(ESI+): m/z=401.2.

Example 256

(2S,4EZ)-$N^1$-benzoyl-4-(chloromethylene)-$N^2$-cyclopropyl-1,2-pyrrolidinedicarboxamide Following the general method as outlined in Example 22, starting from (2S,4EZ)-1-(tert-butoxycarbonyl)-4-(chloromethylene)-2-pyrrolidinecarboxylic acid, benzoyl isocyanate, and cyclopropylamine the title compound was obtained in 76% purity by LC/MS. MS(ESI+): m/z=348.6.

Example 257

(2S,4EZ)-4-{[(3,4-dichlorobenzyl)oxy]imino}-1-(methoxyacetyl)-N-(1-naphthylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, methoxyacetyl chloride, and 1-naphthylmethylamine the title compound was obtained in 91% purity by LC/MS. MS(ESI+): m/z=514.8.

Example 258

(2S,4EZ)-1-benzoyl-N-benzyl-4-(chloromethylene)-N-methyl-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and N-benzyl-N-methylamine the title compound was obtained in 62% purity by LC/MS. MS(ESI+): m/z=369.4.

Example 259

(2S)-$N^2$-(2-furylmethyl)-$N^1$-(3-methoxyphenyl-4-methylene-1,2-pyrrolidinedicarboxamide Following the general method as outlined in Example 22, starting from 1-(tert-butoxycarbonyl)-4-methyleneproline, 1-isocyanato-3-methoxybenzene, and 2-furylmethylamine the title compound was obtained in 95% purity by LC/MS. MS(ESI+): m/z=356.0.

Example 260

(3EZ,5S)-5-[(4-benzhydryl-1-piperazinyl)carbonyl]-1-(phenoxyacetyl)-3-pyrrolidinone O-ethyloxime Following the general method as outlined in Example 22, starting from (2S,4EZ)-1-(tert-butoxycarbonyl)-4-(ethoxyimino)-2-pyrrolidinecarboxylic acid, phenoxyacetyl chloride, and 1-benzhydrylpiperazine the title compound was obtained in 67% purity by LC/MS. MS(ESI+): m/z=541.2.

Example 261

(3EZ,5S)-1-benzoyl-5-(4-morpholinylcarbonyl)-3-pyrrolidinone O-(3,4-dichlorobenzyl)-oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, benzoyl chloride, and morpholine the title compound was obtained in 69% purity by LC/MS. MS(ESI+): m/z=476.2.

Example 262

(2S)-$N^1$-(3-methoxyphenyl)-4-methylene-$N^2$-(1-naphthylmethyl-1,2-pyrrolidine-dicarboxamide Following the general method as outlined in Example 22, starting from 1-(tert-butoxycarbonyl)-4-methyleneproline, 1-isocyanato-3-methoxybenzene, and 1-naphthylmethylamine the title compound was obtained in 55% purity by LC/MS. MS(ESI+): m/z=416.3.

Example 263

$N^2$-(2-methoxyethyl)-4-methylene-$N^1$-(3-methylphenyl)-1,2-pyrrolidinedicarboxamide Following the general method as outlined in Example 22, starting from 1-(tert-butoxycarbonyl)-4-methyleneproline, 1-isocyanato-3-methylbenzene, and 2-methoxyethylamine the title compound was obtained in 85% purity by LC/MS. MS(ESI+): m/z=318.0.

Example 264

(2S,4EZ)-N-allyl-4-{[(4-methoxybenzyl)oxy]imino}-1-(phenoxyacetyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, phenoxyacetyl chloride, and allylamine the title compound was obtained in 72% purity by LC/MS.
MS(ESI+): m/z=438.2.

Example 265

(2S,4EZ)-1-benzoyl-4-(cyanomethylene)-N-(1-naphthylmethyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, benzoyl chloride, and 1-naphthylmethylamine the title compound was obtained in 43% purity by LC/MS. MS(ESI+): m/z=396.0.

Example 266

(2S,4EZ)-4-{[(3,4-dichlorobenzyl)oxy]imino}-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2-oxo-6-pentyl-2H-pyran-3-carbonyl chloride, and 6-quinolinamine the title compound was obtained in 70% purity by LC/MS. MS(ESI+): m/z=621.2.

Example 267

(2S,4EZ)-N-[2-(diethylamino)ethyl]-1-[4-(dimethylamino)butanoyl]-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 4-(dimethylamino)butanoyl chloride, and N1,N1-diethyl-1,2-ethanediamine the title compound was obtained in 100% purity by LC/MS. MS(ESI+): m/z=476.2.

Example 268

(2S,4EZ)-4-[(allyloxy)imino]-1-[4-(dimethylamino)butanoyl]-N-(1-naphthylmethyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-(dimethylamino)buta-noyl chloride, and 1-naphthylmethylamine the title compound was obtained in 85% purity by LC/MS. MS(ESI+): m/z=437.2.

Example 269

(2S,4EZ)-N-[2-(diethylamino)ethyl]-4-(ethoxyimino)-2-pyrrolidinecarboxamide

Following the general method as outlined in Example 22, starting from (2S,4EZ)-1-(tert-butoxycarbonyl)-4-(ethoxyimino)-2-pyrrolidinecarboxylic acid, and N1,N1-diethyl-1,2-ethanediamine the title compound was obtained in 70% purity by LC/MS. MS(ESI+): m/z=271.0.

Example 270

(2S)-4-methylene-1-[(2-oxo-6-pentyl-2H-pyran-3-yl)carbonyl]-N-(6-quinolinyl)-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and 6-quinolinamine the title compound was obtained in 48% purity by LC/MS. (ESI+): m/z=446.2.

Example 271

(2S,4EZ)-1-acryloyl-N-allyl-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, acryloyl chloride, and allylamine the title compound was obtained in 81% purity by LC/MS. MS(ESI+): m/z=252.0.

Example 273 tert-butyl 3-({[(2S,4EZ)-1-acetyl-4-benzylidenepyrrolidinyl]carbonyl}amino)-1-azetidinecarboxylate Following the general method as outlined in Example 22, starting from (2S,4EZ)-4-benzylidene-1-(tert-butoxycarbonyl)-2-pyrrolidinecarboxylic acid, acetyl chloride, and tert-butyl 3-amino-1-azetidinecarboxylate the title compound was obtained in 81% purity by LC/MS. MS(ESI+): m/z=400.2.

Example 273

(2S,4EZ)-4-[(allyloxy)imino]-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 2-oxo-6-pentyl-2H-pyran-3-carbonyl chloride, and 6-quinolinamine the title compound was obtained in 67% purity by LC/MS. MS(ESI+): m/z=503.2.

Example 274

(2S,4EZ)-4-(ethoxyimino)-N-(1-naphthylmethyl-1-(phenoxyacetyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, phenoxyacetyl chloride, and 1-naphthylmethylamine the title compound was obtained in 85% purity by LC/MS. MS(ESI+): m/z=446.3.

Example 275

(2S,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1RS)-2-amino-1-phenylethanol, the title compound was obtained in 96.4% purity by HPLC. MS(ESI+): m/z=472.

Example 276

(2S,4EZ)-1-([1,1'-biphenyl]-3-ylcarbonyl)-N-(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-3-carboxylic acid, and (1RS)-2-amino-1-phenylethanol, the title compound was obtained in 72% purity by HPLC. MS(ESI+): m/z=458.

Example 277

(2S,4EZ)-1-(4-benzoylbenzoyl)-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-benzoylbenzoic acid, and (1RS)-2-amino-1-phenylethanol, the title compound was obtained in 93% purity by HPLC. MS(ESI+): m/z=486.

Example 278

(2S,4EZ)-N-[(2RS)-2-hydroxy-2-phenylethyl]-4-(methoxyimino)-1-(3-phenoxybenzoyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3-phenoxybenzoic acid, and (1RS)-2-amino-1-phenylethanol, the title compound was obtained in 94% purity by HPLC. MS(ESI+): m/z=474.

Example 279

(2S,4EZ)-N-(2RS)-2-hydroxy-2-phenylethyl]-4-(methoxyimino)1-(2-phenoxybenzoyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-phenoxybenzoic acid, and (1RS)-2-amino-1-phenylethanol, the title compound was obtained in 92% purity by HPLC. MS(ESI+): m/z=474.

Example 280

(2S,4EZ)-N-[(2S)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S)-2-amino-1-phenylethanol, the title compound was obtained in 98% purity HPLC. MS(ESI+): m/z=472.

Example 281

(2S,4EZ)-N-[(2R)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R)-2-amino-1-phenylethanol, the title compound was obtained in 84% purity by HPLC. MS(ESI+): m/z=472.

Example 282

(2S,4EZ)-N-(2-hydroxyethyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminoethanol, the title compound was obtained in 75% purity by HPLC. MS(ESI+): m/z=396.

Example 283

(2S,4EZ)-N-(2-hydroxyethyl)-4-(methoxyimino)-N-methyl-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-(methylamino)ethanol, the title compound was obtained in 78% purity by HPLC. MS(ESI+): m/z=410.

Example 284

(2S,4EZ)-1-([1,1'-biphenyl]-4sulfonyl)-N-(1S,2S,3R,4R)-3-(hydroxymethyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and [(1R,2R,3S,4S)-3-aminobicyclo[2.2.1]hept-2-yl]methanol, the title compound was obtained in 79% purity by HPLC. MS(ESI+): m/z=498.

Example 285

(2S,4EZ)-1-([1,1'-biphenyl]-4-ylcarbonyl)-N-(trans-4-hydroxycyclohexyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and trans-4-aminocyclohexanol, the title compound was obtained in 62% purity by HPLC. MS(ESI+): m/z=436.

Example 286

(2S,4EZ)-1-([1,1'-biphenyl]-4-ylcarbonyl)-N-[(1R,2R)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and [(1R,2R)-2-aminocyclohexyl]methanol, the title compound was obtained in 65% purity by HPLC. MS(ESI+): m/z=450.

Example 287

(2S,4EZ)-1-([1,1'-biphenyl]-4-ylcarbonyl-N-[(2RS)-2-hydroxy-3-phenoxypropyl]-4-(methoxyimino)-2-pyrrolidinecarboxamide Following the general method as outlined in Example 22, staring from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-3-phenoxy-2-propanol, the title compound was obtained in 68% purity by HPLC. MS(ESI+): m/z=488.

Example 288

(2S,4EZ)-N-[(2RS)-2-hydroxy-3-phenoxypropyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (2RS)-1-amino-3-phenoxy-2-propanol, the title compound was obtained in 76% purity by HPLC. MS(ESI+): m/z=489.

Example 289

(2S,4EZ)-1-([1,1'-biphenyl]-4-ylsulfonyl)-N-[(2RS)-2-hydroxy-3-phenoxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-3-phenoxy-2-propanol, the title compound was obtained in 78% purity by HPLC. MS(ESI+): m/z=524.

Example 290

(2S,4EZ)-1-([1,1'-biphenyl]-4-ylcarbonyl)-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-[(1RS)-2-amino-1-hydroxyethyl]phenol, the title compound was obtained in 63% purity by HPLC. MS (ESI+): m/z=474.4.

Example 291

(2S,4EZ)-1-([1,1'-biphenyl]-4-ylsulfonyl)-N-[(2RS)-2-hydroxy-2-(4-hydroxyphenyl)ethyl]4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4sulfonyl chloride, and 4-[(1RS)-2-amino-1-hydroxyethyl]phenol, the title compound was obtained in 72% purity by HPLC. MS(ESI+): m/z=510.

Example 292

(2S,4EZ)-1-([1,1'-biphenyl]-4-ylcarbonyl)-N-[(1-hydroxycyclohexyl)methyl]-4-(methoxyimino-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 1-(aminomethyl)cyclohexanol, the title compound was obtained in 65% purity by HPLC. MS(ESI+): m/z=450.

Example 293

(2S,4EZ)-N-(1-hydroxycyclohexyl)methyl]-4-(methoxyimino)-1-[4-(3-pyridin)benzoyl]-2pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and 1-(aminomethyl)cyclohexanol, the title compound was obtained in 69% purity by HPLC. MS(ESI+): m/z=451.

Example 294

(2S,4EZ)-1-([1,1'-biphenyl]-4-ylsulfonyl)-N-[(1-hydroxycyclohexyl)methyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and 1-(aminomethyl)cyclohexanol, the title compound was obtained in 66% purity by HPLC. MS(ESI+): m/z=486.

Example 295

(2S,4EZ)-1-([1,1'-biphenyl]-4-ylcarbonyl)-N-[(2RS)-2-(3,4-dihydroxyphenyl)-2-hydroxyethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-carbonyl chloride, and 4-(1RS)-2-amino-1-hydroxyethyl-1,2-benzenediol, the title compound was obtained in 66% purity by HPLC. MS(ESI+): m/z=490.

Example 296

(2S,4EZ)-N-[(2S)-2-hydroxy-2-phenylethyl-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and (1S)-2-amino-1-phenylethanol, the title compound was obtained in 65% purity by HPLC. MS(ESI+): m/z=459.

Example 297

(2S,4EZ)-N-[(2S)-2-hydroxy-2-phenylethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (1S)-2-amino-1-phenylethanol, the title compound was obtained in 73% purity by HPLC. MS(ESI+): m/z=459.

Example 298

(2S,4EZ)-N-[(2S)-2-hydroxy-2-phenylethyl]-4-(methoxyimino-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl)benzoic acid, and (1S)-2-amino-1-phenylethanol, the title compound was obtained in 69% purity by HPLC. MS(ESI+): m/z=459.

Example 299

(2S,4EZ)-1-([1,1'-biphenyl]-4-ylcarbonyl)-N-[(2RS)-2,3-dihydroxypropyl]-4-(methoxyimino)-2-pyrrolidinecarboxamide Following the general method as outlined in Example 22, starting from (2S,4EZ)-1(tert-butoxycarbonyl)-4-(methoxyimino)-2-pyrrolidinecarboxylic acid, [1,1'-biphenyl]-4-carbonyl chloride, and (2RS)-3-amino-1,2-propanediol, the title compound was obtained in 73% purity by HPLC. MS(ESI+): m/z=412.

Example 300

(2S,4EZ)-1-([1,1'-biphenyl]-4-ylsulfonyl)-N-[(2RS)-2,3-dihdroxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and (2RS)-3-amino-1,2-propanediol, the title compound was obtained in 64% purity by HPLC. MS(ESI+): m/z=448.

Example 301

(2S,4EZ)-1-([1,1'-biphenyl]-4-ylcarbonyl)-N-[(2RS)-2-hydroxy-3-(4-methoxyphenoxy)propyl]-4-(methoxyimino)-27pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-3-(4-methoxyphenoxy)-2-propanol, the title compound was obtained in 81% purity by HPLC. MS(ESI+): m/z=518.

Example 302

(2S,4EZ)-N-[(2RS)-2-hydroxy-3-(4-methoxyphenoxy)propyl]-4(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (2RS)-1-amino-3-(4-methoxyphenoxy)-2-propanol, the title compound was obtained in 63% purity by HPLC. MS(ESI+): m/z=519.

Example 303

(2S,4EZ)-1-([1,1'-biphenyl]-4-ylsulfonyl)-N-[(2RS)-2-hydroxy-3-(4-methoxyphenoxy)propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-3-(4-methoxyphenoxy)-2-propanol, the title compound was obtained in 69% purity by HPLC. MS(ESI+): m/z=554.

Example 304

(2S,4EZ)-1-([1,1'-biphenyl]-4-ylcarbonyl)-N-[(2RS)-2-hydroxypropyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-2-propanol, the title compound was obtained in 82% purity by HPLC. MS(ESI+): m/z=396.

Example 305

(2S,4EZ)-1-([1,1'-biphenyl]-4-ylsulfonyl)-N-[(2RS)-2-hydroxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-2-propanol, the title compound was obtained in 75% purity by HPLC. MS(ESI+): m/z=432.

Example 306

(2S,4EZ)-1-([1,1'-biphenyl]-4-ylsulfonyl)-N-[(2RS)-2-hydroxy-2-(2-naphthyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1RS)-2-amino-1-(2-naphthyl)ethanol, the title compound was obtained in 77% purity by HPLC. MS(ESI+): m/z=544.

Example 307

(2S,4EZ)-1-([1,1'-biphenyl]-4-ylcarbonyl)-N-L(2RS)-2-hydroxy-2-(4-nitrophenyl)ethyl]-4-(methoxyimino)-2-pyrrolidinecarboxamide Following the general method as outlined in Example 22, starting from (2S,4E2)-1-(tert-butoxycarbonyl)-4-(methoxyimino)-2-pyrrolidinecarboxylic acid, [1,1'-biphenyl]-4-carbonyl chloride, and (1RS)-2-amino-1-(4-nitrophenyl)ethanol, the title compound was obtained in 84% purity by HPLC. MS(ESI+): m/z=503.

Example 308

(2S,4EZ)-N-[(2RS)-2-hydroxy-2-(4-nitrophenylethyl]-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and (1RS)-2-amino-1-(4-nitrophenyl)ethanol, the title compound was obtained in 89% purity by HPLC. MS(ESI+): m/z=504.

Example 309

(2S,4EZ)-N-[(2RS)-2-hydroxy-2-(4-nitrophenyl)ethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (1RS)-2-amino-1-(4-nitrophenyl)ethanol, the title compound was obtained in 72% purity by HPLC. MS(ESI+): m/z=504.

Example 310

(2S,4EZ)-N-[(2RS)-2-hydroxy-2-(4-nitrophenyl)ethyl]-4-(methoxyimino)-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl)benzoic acid, and (1RS)-2-amino-1-(4-nitrophenyl)ethanol, the title compound was obtained in 63% purity by HPLC. MS(ESI+): m/z=504.

Example 311

(2S,4EZ)-1-([1,1'-biphenyl]-4-ylsulfonyl)-N-[(2RS)-2-hydroxy-2-(4-nitrophenyl)ethyl]-4-(methoxyimino-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1RS)-2-amino-1-(4-nitrophenyl) ethanol, the title compound was obtained in 79% purity by HPLC. MS(ESI+): m/z=539.

Example 312

(2S,4E2)-N-{(2RS)-3-[4-(acetylamino)phenoxy]-2-hydroxypropyl}-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and N-(4-{[(2RS)-3-amino-2-hydroxypropyl]oxy}phenyl)acetamide, the title compound was obtained in 79% purity by HPLC. MS(ESI+): m/z=545.

Example 313

(2S,4EZ)-N-{(2RS)-3-[4-(acetylamino)phenoxy]-2-hydroxypropyl}-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and N-(4-{[(2RS)-3-amino-2-hydroxypropyl]oxy}phenyl) acetamide, the title compound was obtained in 62% purity by HPLC. MS(ESI+): m/z=546.

Example 314

(2S,4EZ)-N-{(2RS)-3-[4-(acetylamino)phenoxy]-2-hydroxypropyl}-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and N-(4-{[(2RS)-3-amino-2-hydroxypropyl]oxy}phenyl) acetamide, the title compound was obtained in 66% purity by HPLC. MS(ESI+): m/z=546.

Example 315

(2S,4EZ)-N-{(2RS)-3-[4-(acetylamino)phenoxy]-2-hydroxypropyl}-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and N-(4-{[(2RS)-3-amino-2-hydroxypropyl]oxy}phenyl) acetamide, the title compound was obtained in 62% purity by HPLC. MS(ESI+): m/z=581.

Example 316

(2S,4EZ)-1-([1,1'-biphenyl]-4-ylcarbonyl)-N-[(2R)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R)-2-amino-1-phenylethanol, the title compound was obtained in 84% purity by HPLC. MS(ESI+): m/z=458.

Example 317

(2S,4EZ)-N-[(2R)-2-hydroxy-2-phenylethyl]-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and (1R)-2-amino-1-phenylethanol, the title compound was obtained in 66% purity by HPLC. MS(ESI+): m/z=459.

Example 318

(2S,4EZ)-N-[(2R)-2-hydroxy-2-phenylethyl]-4-(methoxyimino-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (1R)-2-amino-1-phenylethanol, the title compound was obtained in 76% purity by HPLC. MS(ESI+): m/z=459.

Example 319

(2S,4EZ)-N-[(2R)-2-hydroxy-2-phenylethyl]-4-(methoxyimino)-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl)benzoic acid, and (1R)-2-amino-1-phenylethanol, the title compound was obtained in 65% purity by HPLC. MS(ESI+): m/z=459.

Example 320

(2S,4EZ)-1-([1,1'-biphenyl]-4-ylsulfonyl)-N-[(2R)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R)-2-amino-1-phenylethanol, the title compound was obtained in 87% purity by HPLC. MS(ESI+): m/z=494.

Example 321

(2S,4EZ)-1-([1,1'-biphenyl]-4-ylcarbonyl)-N-(3-hydroxypropyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3-amino-1-propanol, the title compound was obtained in 81% purity by HPLC. MS(ESI+): m/z=395.

Example 322

(2S,4EZ)-1-([1,1'-biphenyl]-4-ylsulfonyl)-N-(3-hydroxypropyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and 3amino-1-propanol, the title compound was obtained in 64% purity by HPLC. MS(ESI+): m/z=432.

Example 323

(3EZ,5S)-1-([1,1'-biphenyl]-4-ylcarbonyl)-5-[(4-hydroxyphenyl-1-piperidinyl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-phenyl-4-piperidinol, the title compound was obtained in 74% purity by HPLC. MS(ESI+): m/z=498.

Example 324

(3EZ,5S)-5-[(4-hydroxy-4-phenyl-1-piperdinyl]carbonyl]-1-[4-(4-pyridinyl)benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and 4-phenyl-4-piperidinol, the title compound was obtained in 78% purity by HPLC. MS(ESI+): m/z=499.

Example 325

(3EZ,5S)-5-[(4-hydroxy-4-phenyl-1-piperidinyl)carbonyl-1-[4-(3-pyridinyl)benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and 4-phenyl-4-piperidinol, the title compound was obtained in 79% purity by HPLC. MS(ESI+): m/z=499.

Example 326

(3EZ,5s)-1-([1,1'-biphenyl]-4-ylsulfonyl)-5-[(4hydroxy-4-phenyl-1-piperidinyl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 4-phenyl-4-piperidinol, the title compound was obtained in 84% purity by HPLC. MS(ESI+): m/z=534.

Example 327

(2S,4EZ)-1-([1,1'-biphenyl]-4-ylcarbonyl)-N[(1S,2EZ)-2-hydroxycyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and,(1S,2S)-2-aminocyclohexanol, the title compound was obtained in 84% purity by HPLC. MS(ESI+): m/z=436.

Example 328

(2S,4EZ)-1-([1,1'-biphenyl]-4-ylsulfonyl)-N-[(1S,2S)-2-hydroxycyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1S,2S)-2-aminocyclohexanol, the title compound was obtained in 61% purity by HPLC. MS(ESI+): m/z=472.

Example 329

(2S,4EZ)-N-benzyl-1-([1,1'-biphenyl]-4-ylcarbonyl)-N-(2-hydroxyethyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-(benzylamino)ethanol, the title compound was obtained in 74% purity by HPLC. MS(ESI+): m/z=472.

Example 330

(2S,4EZ)-N-b[1-N-(2 hydroxyethyl)-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and 2-(benzylamino)ethanol, the title compound was obtained in 82% purity by HPLC. MS(ESI+): m/z=473.

Example 331

(3EZ,5S)-1-([1,1'-biphenyl]-4-ylcarbonyl)-5-{[(3RS)-3-hydroxypiperidinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (3RS)-3-piperidinol, the title compound was obtained in 78% purity by HPLC. MS(ESI+): m/z=422.

Example 332

(3EZ,5S)-5-{[(3RS)-3-hydroxypiperidinyl]carbonyl}-1-[4-(4-pyridinyl)benzol]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and (3RS)-3-piperidinol, the title compound was obtained in 91% purity by HPLC. MS(ESI+): m/z=423.

Example 333

(3EZ,5S)-5-{[(3RS)-3-hydroxypiperidinyl]carbonyl}-1-4-(3-pyridinyl)benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (3RS)-3-piperidinol, the title compound was obtained in 84% purity by HPLC. MS(ESI+): m/z=423.

Example 334

(3EZ,5S)-1-([1,1'-biphenyl]-4-ylsulfonyl)-5-{[(3RS)-3-hydroxypiperidinyl]carbonyl}3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (3RS)-3-piperidinol, the title compound was obtained in 79% purity by HPLC. MS(ESI+): m/z=458.

Example 335

(2S,4EZ)-1-([1,1'-biphenyl]-4-ylcarbonyl)-N-[(1S,2S)-2-hydroxy-1-(hydroxymethyl)-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2S)-2-amino-1-phenyl-1,3-propanediol, the title compound was obtained in 88% purity by HPLC. MS(ESI+): m/z=488.

Example 336

(2S,4EZ)-N-[(1S,2S)-2-hydroxy-1-(hydroxymethyl)-2-phenylethyl]-4-(methoxyimino)-1-(4-pyridinyl)benzoyl]-2pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and (1S,2S)-2-amino-1-phenyl-1,3-propanediol, the title compound was obtained in 64% purity by HPLC. MS(ESI+): m/z=489.

Example 337

(2S,4EZ)-N-[(1S,2S)-2-hydroxy-1-(hydroxymethyl-2-phenylethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (1S,2S)-2-amino-1-phenyl-1,3-propanediol, the title compound was obtained in 93% purity by HPLC. MS(ESI+): m/z=489.

Example 338

(2S,4EZ)-1-([1,1'-biphenyl]-4-ylsulfonyl)-N-[(1S,2S)-2-hydroxy-1-(hydroxymethyl)-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1S,2S)-2-amino-1-phenyl-1,3-propanediol, the title compound was obtained in 82% purity by HPLC. MS(ESI+): m/z=524.

Example 339

(2S,4EZ)-N-(2-anilinoethyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and $N^2$-phenyl-1,2-ethanediamine, the title compound was obtained in 93% purity by HPLC. MS(ESI+): m/z=457.

Example 340

(2S,4EZ)-N-(2-anilinoethyl)-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and $N^1$-phenyl-1,2-ethanediamine, the title compound was obtained in 85% purity by HPLC. MS(ESI+): m/z=458.

Example 341

(2S,4EZ)-N-(2-anilinoethyl)-4-(methoxyimino)-1-
[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and $N^1$-phenyl-1,2-ethanediamine, the title compound was obtained in 85% purity by HPLC. MS(ESI+): m/Z=458.

Example 342

(2S,4EZ)-N-(2-anilinoethyl)-4-(methoxyimino)-1-
[4-(2-pyridin)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl) benzoic acid, and $N^1$-phenyl-1,2-ethanediamine, the title compound was obtained in 67% purity by HPLC. MS(ESI+): m/Z=458.

Example 343

(2S,4EZ)-N-(2-anilinoethyl)-1-([1,1'-biphenyl]-4-
ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and $N^1$-phenyl-1,2-ethanediamine, the title compound was obtained in 73% purity by HPLC. MS(ESI+): m/z=493.

Example 344

(3EZ,5S)-1-([1,1'-biphenyl]-4-ylcarbonyl)-5-[(4-
hydroxy-1-piperidinyl)carbonyl]-3-pyrrolidinone
O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-piperidinol, the title compound was obtained in 86% purity by HPLC. MS(ESI+): m/z=422.

Example 345

(3EZ,56)-1-([1,1'-biphenyl]-4-ylsulfonyl-5-[(4-hydroxy-1-piperidinyl)carbonyl]-3-pyrrolidinone
O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]4-sulfonyl chloride, and 4-piperidinol, the title compound was obtained in 68% purity by HPLC. MS(ESI+): m/z=458.

Example 346

(2S,4EZ)-N-[(1S,2R,3S,4R)-3-(aminocarbonyl)bicyclo[2.2.1]hept-5-en-2-yl]-1-([1,1'-biphenyl]-4-ylsulfonyl)-4(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R,2S,3,R,4S)-3-aminobicyclo[2.2.1]hept-5-ene-2-carboxamide, the title compound was obtained in 79% purity by HPLC. MS(ESI+): m/z=509.

Example 347

(2S,4EZ)-N-(3-amino-3-oxopropyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]carbonyl chloride, and 3-aminopropanamide, the title compound was obtained in 71% purity by HPLC. MS(ESI+): m/z=409.

Example 348

(2S,4EZ)-N-[(1S,2S,3R,4R)-3-(aminocarbonyl)bicyclo[2.2.1]hept-5-en-2-yl-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R,2R,3S,4S)-3-aminobicyclo[2.2.1]hept-5-ene-2-carboxamide, the title compound was obtained in 83% purity by HPLC. MS(ESI+): m/z=509.

Example 349

(2S,4EZ)-1-([1,1'-biphenyl]-4-ylcarbonyl-N-(4-hydroxybutyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-amino-1-butanol, the title compound was obtained in 68% purity by HPLC. MS(ESI+): m/z=410.

Example 350

(2S,4EZ)-([1,1'-biphenyl]-4-ylsulfonyl)-N-(4-hydroxybutyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 4-amino-1-butanol, the title compound was obtained in 78% purity by HPLC. MS(ESI+): m/z=446.

Example 351

(2S,4EZ)-1-([1,1'-biphenyl]-4-ylsulfonyl)-N-[(1R, 2R)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4sulfonyl chloride, and [(1R,2R)-2-aminocyclohexyl]methanol, the title compound was obtained in 40% purity by HPLC. MS(ESI+): m/z=486.

Example 352

(2S,4EZ)-1-([1,1'-biphenyl]-4ylsulfonyl)-N-[(1R,2S, 3R,4S)-3-(hydroxymethyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyly]4-sulfonyl chloride, and [(1S,2R,3S,4R)-3-aminobicyclo[2.2.1]hept-2-yl]methanol, the title compound was obtained in 58% purity by HPLC. MS(ESI+): m/z=498.

Example 353

(2S,4EZ)-1-([1,1'-biphenyl]-4-ylsulfonyl)-N-[(1R, 2S)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and [(1S,2R)-2-aminocyclohexyl]methanol, the title compound was obtained in 41% purity by HPLC. MS(ESI+): m/z=486.

Example 354

(2S,4E and 4Z)-N-[(2RS)-2-hydroxy-2-phenylethyl]-4-(methoxyimino-1-(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'biphenyl]-4-carboxylic acid, and (1RS)-2-amino-1-phenylethanol, the title compounds were obtained as a mixture of E/Z-isomers of the oxime functionality. Separation of the isomers by flash chromatography yielded (2S,4E)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide in 98.9% purity and (2S,4Z)-N-[(2RS)-2-hydroxy-2-phenylethyl]4-(methoxyimino)-1-[(2'-methyl[1,1'-biphenyl]-4-yl)carbonyl]-2-pyrrolidinecarboxamide in 99.9% purity by HPLC. MS(ESI+): m/z=472.

Example 355

(2S,4E and 4Z)-N-[(2S)-2-hydroxy-2-phenylethyl]-4-(methoxyimino)-1-[2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S)-2-amino-1-phenylethanol, the title compounds were obtained as a mixture of E/Z-isomers of the oxime functionality. Separation of the isomers by flash chromatography yielded (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide in 98.9% parity and (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide in 99.8% purity by HPLC. MS(ESI+): m/z=472.

Example 356

(2S,4E and 4Z)-N-[(2R)-2-hydroxy-2-phenylethyl-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R)-2-amino-1-phenylethanol, the title compounds were obtained as a mixture of E/Z-isomers of the oxime functionality. Separation of the isomers by flash chromatography yielded (2S,4E)-N-[(2R)-2-hydroxy-2-phenylethyl]-4-(methoxyimino)-1-[(2'-methyl[1,1'-biphenyl]-4-yl)carbonyl]-2-pyrrolidinecarboxamide in 99.7% purity and (2S,4Z)-N-[(2R)-2-hydroxy-2-phenylethyl]-4-(methoxyimino)-1-[(2'-methyl[1,1'-biphenyl]-4-yl)carbonyl]-2-pyrrolidinecarboxamide in 99.7% purity by HPLC. MS(ESI+): m/z=472.

Example 357

(2S,4EZ)-1-([1,1'-biphenyl]-4-ylcarbonyl)-N-(1R, 2S)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-carbonyl chloride, and [(1S,2R)-2-aminocyclohexyl]methanol, the title compound was obtained in 63% purity by HPLC. MS(ESI+): m/z=450.

Example 358

(2S,4EZ)-1-([1,1'-biphenyl]-4-ylcarbonyl)-N-[2-hydroxy-1-(hydroxymethyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-carbonyl chloride, and 2-amino-1,3-propanediol, the title compound was obtained in 61% purity by HPLC. MS(ESI+): m/z=412.

Example 359

(2S,4EZ)-N-[(1S,2R,3S,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4-

Example 360

(2S,4EZ)-N-[(1S,2S,3R,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R,2R,3S,4S)-3-aminobicyclo[2.2.1]hept-5-ene-2-carboxamide, the title compound was obtained in 78% purity by HPLC. MS(ESI+): m/z=473.

Example 361

(2S,4EZ)-1-([1,1'-biphenyl]-4-ylcarbonyl)-N-[(2S)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S)-2-amino-1-phenylethanol, the title compound was obtained in 87% purity by HPLC. MS(ESI+): m/z=458.

Example 362

(2RS)-3-({[(2S,4EZ)-1-([1,1'-biphenyl]-4-ylcarbonyl)-4-(methoxyimino)pyrrolidinyl]carbonyl}amino)-2-hydroxypropanoic acid Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-3-amino-2-hydroxypropanoic acid, the title compound was obtained in 44% purity by HPLC. MS(ESI+): m/z=426.

Example 363

(2S,4EZ)-N-[(1R,2S)-2-(aminocarbonyl)cyclohexyl]-1-([1,1'-biphenyl]-4-ylcarbonyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2R)-2-aminocyclohexanecarboxamide, the title compound was obtained in 89% purity by HPLC. MS(ESI+): m/z=463.

Example 364

(2S,4EZ)-1-([1,1'-biphenyl]-4-ylcarbonyl)-N-[(1RS)-2-hydroxy-1-methylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-2-amino-1-propanol, the title compound was obtained in 81% purity by HPLC. MS(ESI+): m/z=396.

Example 365

(2S,4EZ)-1-([1,1'-biphenyl]-4-ylcarbonyl)-N-[(1S,2S)-2-hydroxy-1-(hydroxymethyl)-2-(4-nitrophenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2S)-2-amino-1-(4-nitrophenyl)-1,3-propanediol, the title compound was obtained in 70% purity by HPLC. MS(ESI+): m/z=533.

Example 366

4-({[(2S,4EZ)-1-([1,1'-biphenyl]-ylcarbonyl)-4(methoxyimino)pyrolidinyl]carbonyl}amino)butanoic acid Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-aminobutanoic acid, the title compound was obtained in 57% purity by HPLC. MS(ESI+): m/z=424.

Example 367

(2S,4EZ)-N-[(2S)-2-hydroxy-2-phenylethyl]-1-[(2'-methoxy[1,1'-biphenyl]-4-yl)carbonyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1S)-2-amino-1-phenylethanol, the title compound was obtained in 90% purity by HPLC. MS(ESI+): m/z=488.

Example 368

(2S,4EZ)-N-[(2RS)-2-hydroxy-2-(2-naphthyl)ethyl]-1-[(2'-methoxy[1,1'-biphenyl]-4-ylcarbonyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1RS)-2-amino-1-(2-naphthyl)ethanol, the title compound was obtained in 67% purity by HPLC. MS(ESI+): m/z=538.

Example 369

(2S,4EZ)-N-[(1RS)-2-hydroxy-1-methylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-2-amino-1-propanol, the title compound was obtained in 88% purity by HPLC. MS(ESI+): m/z=410.

Example 370

(2S,4EZ)-N-[(1S,2S)-2-hydroxy-1-(hydroxymethyl)-
2-(4-nitrophenyl)ethyl]-4-(methoxyimino)-1-[(2'-
methyl[1,1'-biphenyl]-4yl)carbonyl]-2-pyrrolidin-
ecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S,2S)-2-amino-1-(4-nitrophenyl)-1,3-propanediol, the title compound was obtained in 74% purity by HPLC. MS(ESI+): m/z=547.

Example 371

(2S,4EZ)-N-[(1S,2S)-2-hydroxy-1-(hydroxymethyl)-
2-(4-nitrophenyl)ethyl]-4-(methoxyimino)-1-[(2'-
methoxy[1,1'-biphenyl]-4-yl)carbonyl]-2-pyrrolidin-
ecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1S,2S)-2-amino-1-(4-nitrophenyl)-1,3-propanediol, the title compound was obtained in 61% purity by HPLC. MS(ESI+): m/z=563.

Example 372

(3EZ,5S)-5-[(4-hydroxy-1-piperidinyl)carbonyl]-1-
[(2'-methyl]-1,1'-biphenyl]-4-ylcarbonyl]-3-pyrroli-
dinone O-methyloxime Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-piperidinol, the title compound was obtained in 86% purity by HPLC. MS(ESI+): m/z=436.

Example 373

(2S,4EZ)-N-[(1S,2S,3R,4R)-3-(aminocarbonyl)bicy-
clo[2.2.1]hept-5-en-2-yl]-4-(methoxyimino)-1-(2'-
methyl[1,1'-biphenyl]-4-yl)carbonyl]-2-pyrrolidin-
ecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R,2R,3S,4S)-3-aminobicyclo[2.2.1]hept-5-ene-2-carboxamide, the title compound was obtained in 55% purity by HPLC. MS(ESI+): m/z=487.

Example 374

(2S,4EZ)-N-[(2RS)-2-hydroxy-2-phenylethyl]-1-
[(2'-methoxy[1,1'-biphenyl]-4-yl)carbonyl]-4-(meth-
oxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1RS)-2-amino-1-phenylethanol, the title compound was obtained in 82% purity by HPLC. MS(ESI+): m/z=488.

Example 375

(2S,4EZ)-N-[(2RS)-2-hydroxypropyl]-4-(methoxy-
imino)-1-[(2'-methyl[1,1'-biphenyl]-4-yl)carbonyl]-
2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-1-amino-2-propanol, the title compound was obtained in 90% purity by HPLC. MS(ESI+): m/z=410.

Example 376

(2S,4EZ)-N-[(2RS)-2,3-dihydroxypropyl]-4-(meth-
oxyimino)-1-[(2'-methyl[1,1'-biphenyl]-4-yl)carbo-
nyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]4-carboxylic acid, and (2RS)-3-amino-1,2-propanediol, the title compound was obtained in 67% purity by HPLC. MS(ESI+): m/z=426.

Example 377

(2S,4EZ)-N-(3-hydroxypropyl)-4-methoxyimino)-1-
[(2'-methyl[1,1'-biphenyl]-4-yl)carbonyl]-2-pyrro-
lidinecarboxamide Following the general method as outlined in Example 22, starting from (2S,4EZ)-1-(tert-butoxycarbonyl)-4-(methoxyimino)-2-pyrrolidinecarboxylic acid, 2-methyl[1,1'-biphenyl]-4 -carboxylic acid, and 3-amino-1-propanol, the title compound was obtained in 90% purity by HPLC. MS(ESI+): m/z=410.

Example 378

(2S,4EZ)-N-(2-amino-2-oxoethyl)-1-([1,1'-biphe-
nyl]-4-ylcarbonyl)-4-(methoxyimino)-2-pyrrolidin-
ecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-aminoacetamide, the title compound was obtained in 82% purity by HPLC. MS(ESI+): m/z=395.

Example 379

(2S,4EZ)-N-(2-amino-2-oxoethyl)-4-(methoxy-
imino)-1-[(2'-methyl[1,1'-biphenyl]-4-yl)carbonyl]-
2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminoacetamide, the title compound was obtained in 92% purity by HPLC. MS(ESI+): m/z=409.

Example 380

(2S,4EZ)-1-([1,1'-biphenyl]-4-ylcarbonyl)-N-[(2RS)-2-hydroxy-2-(3-hydroxyphenyl)ethyl]4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3-[(1RS)-2-amino-1-hydroxyethyl] phenol, the title compound was obtained in 88% purity by HPLC. MS(ESI+): m/z=504.

Example 381

(2S,4E)-1-([1,1'-biphenyl]-4-ylcarbonyl)-N-[(1S,2R,3S,4R)-3-(hydroxymethyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and [(1R,2S,3R,4S)-3-aminobicyclo[2.2.1]hept-2-yl]methanol, the title compound was obtained in 64% purity by HPLC. MS(ESI+): m/z=462.

Example 382

(2S,4EZ)-N-[(1R,2S,3R,4S)-3-hydroxymethyl)bicyclo[2.2.1]hept-2-yl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and [(1S,2R,3S,4R)-3-aminobicyclo[2.2.1]hept-2-yl]methanol, the title compound was obtained in 56% purity by HPLC. MS(ESI+): m/z=492.

Example 383

(2S,4EZ)-N-(trans-4-hydroxycyclohexyl)-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4carboxylic acid, and trans-4-aminocyclohexanol, the title compound was obtained in 61% purity by HPLC. MS(ESI+): m/z=466.

Example 384

(2S,4EZ)-N-[(1R,2R)-2-hydroxymethyl)cyclohexyl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and [(1R,2R)-2-aminocyclobexyl]methanol, the title compound was obtained in 68% purity by HPLC. MS(ESI+): m/z=480.

Example 385

(2S,4EZ)-N-[(2RS)-2-hydroxy-3-phenoxypropyl]-4-(methoxyimino)-1-(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4 -carboxylic acid, and (2RS)-1-amino-3-phenoxy-2-propanol, the title compound was obtained in 80% purity by HPLC. MS(ESI+): m/z=502.

Example 386

(2-N-[(2RS)-2-hydroxy-2-(4-hydroxyphenylethyl]-4-methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-[(1RS)-2-amino-1-hydroxyethyl]phenol, the title compound was obtained in 76% purity by HPLC. MS(ESI+): m/z=488.

Example 387

(2S,4EZ)-N-[(2RS)-2-hydroxy-2-(4-hydroxyphenyl)ethyl]-4-(methoxyimino)-1-[(2'-methoxy[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and 4-[(1RS)-2-amino-1-hydroxyethylphenol, the title compound was obtained in 90% purity by HPLC. MS(ESI+): m/z=504.

Example 388

(2S,4EZ)-N-[(2R)-2-hydroxy-2-(4-hydroxy-3-methoxyphenyl)ethyl]-1-[(2'-methyl]-[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-[(1RS)-2-amino-1-hydroxyethyl]-2-methoxyphenol, the title compound was obtained in 67% purity by HPLC. MS(ESI+): m/z=518.

Example 389

(2S,4EZ)-N-[(2RS)-2-hydroxy-2-(4-hydroxy-3-methoxyphenyl)ethyl-1-[(2-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl] -4-carboxylic acid, and 4-[(1RS)-2-amino-1-hydroxyethyl]-2-methoxyphenol, the title compound was obtained in 87% purity by HPLC. MS(ESI+): m/z=534.

Example 390

(2S,4EZ)-N-[(2RS)-2-(3,4-dihydroxyphenyl)-2-hydroxyethyl]-1-[2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and 4-[(1RS)-2-amino-1-hydroxyethyl]-1,2-benzenediol, the title compound was obtained in 69% purity by HPLC. MS(ESI+): m/z=520.

Example 391

(2R,4EZ)-1-([1,1'-biphenyl]-4-ylcarbonyl)-N-[(2RS)-2-hydroxy-2-phenylethyl]-4-(methoxyimino)-2-pyrrolidinecarboxamide Following the general method as outlined in Example 22, starting from (2R,4EZ)-1-(tert-butoxycarbonyl)-4-(methoxyimino)-2-pyrrolidinecarboxylic acid, [1,1'-biphenyl]-4-carbonyl chloride, and (1RS)-2-amino-1-phenylethanol, the title compound was obtained in 90% purity by HPLC. MS(ESI+): m/z=456.

Example 392

(2R,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2R,4EZ)-1-(tert-butoxycarbonyl)-4-(methoxyimino)-2-pyrrolidinecarboxylic acid, 2'-methyl[1,1'-biphenyl]-4-carboxylic acid, and (1RS)-2-amino-1-phenylethanol, the title compound was obtained in 94% purity by HPLC. MS(ESI+): m/z=472.

Example 393

(2S,4EZ)-1-[(2'-cyano[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and (1RS)-2-amino-1-phenylethanol, the title compound was obtained in 86% purity by HPLC. MS(ESI+): m/z=483.

Example 394

(2S,4EZ)-1-[(3',4'-dichloro[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1-biphenyl]-4-carboxylic acid, and (1RS)-2-amino-1-phenylethanol, the title compound was obtained in 89% purity by HPLC. MS(ESI+): m/z=527.

Example 395

(2S,4EZ)-1-[(2',6'-dimethyl[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and (1RS)-2-amino-1-phenylethanol, the title compound was obtained in 95% purity by HPLC. MS(ESI+): m/z=486.

Example 396

(2S,4EZ)-1-[(2',3-dimethyl[1,1'-biphenyl]-4-yl)carbonyl]-N-[(2RS)-2hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]4carboxylic acid, and (1RS)-2-amino-1-phenylethanol, the title compound was obtained in 83% purity by HPLC. MS(ESI+): m/z=486.

Example 397

(2S,4EZ)-N-[(2RS)-2-hydroxy-2-(3-hydroxyphenyl ethyl-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4 -carboxylic acid, and 3-[(1RS)-2-amino-1-hydroxyethyl]phenol, the title compound was obtained in 70% purity by HPLC. MS(ESI+): m/z=488.

Example 398

(2S,4EZ)-N-[(2RS)-2-hydroxy-2-(3-hydroxyphenyl) ethyl]-4-(methoxyimino)-1-[(2'-cyano[1,1'-biphenyl]-4-ylcarbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]4carboxylic acid, and 3-[(1RS)-2-amino-1-hydroxyethyl]phenol, the title compound was obtained in 86% purity by HPLC. MS(ESI+): m/z=499.

Example 399

(2S,4EZ)-N-[(2RS)-2-hydroxy-2-(3-hydroxyphenyl) ethyl]-4-(methoxyimino)-1-[(3',4'-dichloro[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1-biphenyl]-4-carboxylic acid, and 3-[(1RS)-2-amino-1-hydroxyethyl]phenol, the title compound was obtained in 91% purity by HPLC. MS(ESI+): m/z=543.

Example 400

(2S,4EZ)-N-[(2RS)-2 hydroxy-2-(3-hydroxyphenyl)ethyl]-4(methoxyimino)-1-[(2',6'-dimethyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-[(1RS)-2-amino-1-hydroxyethyl]phenol, the title compound was obtained in 87% purity by HPLC. MS(ESI+): m/z=502.

Example 401

(2S,4EZ)-N-[(2S)-2-hydroxy-2-(3-hydroxyphenyl)ethyl]-4(methoxyimino)-1-[(2',3-dimethyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 3-[(1RS)-2-amino-1-hydroxyethyl]phenol, the title compound was obtained in 91% purity by HPLC. MS(ESI+): m/z=502.

Example 402

(2S,4EZ)-1-[(3',4'-dichloro[1,1'-biphenyl]-4-yl)carbonyl]-N-[(2RS)-2-hydroxy-2-(4-hydroxyphenyl)ethyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and 4-[(1RS)-2-amino-1-hydroxyethyl]phenol, the title compound was obtained in 86% purity by HPLC. MS(ESI+): m/z=543.

Example 403

(2S,4EZ)-1-[(2',6'-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]4-carboxylic acid, and 4-[(1RS)-2-amino-1-hydroxyethyl]phenol, the title compound was obtained in 89% purity by HPLC. MS(ESI+): m/z=502.

Example 404

(2S,4EZ)-1-[(2',3-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 4-[(1RS)-2-amino-1-hydroxyethyl]phenol, the title compound was obtained in 90% purity by HPLC. MS(ESI+): m/z=502.

Example 405

(2S,4EZ)-1-[(2',6'-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and (2RS)-1-amino-3-(4-methoxyphenoxy)-2-propanol, the title compound was obtained in 87% purity by HPLC. MS(ESI+): m/z=546.

Example 406

(2S,4EZ)-1-(2',3-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and (2RS)-1-amino-3-(4-methoxyphenoxy)-2-propanol, the title compound was obtained in 77% purity by HPLC. MS(ESI+): m/z=546.

Example 407

(2S,4EZ)-N-(2-amino-2-oxoethyl)-1-(2',6'-dimethyl[1,1'-biphenyl]-4-yl)carbonyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]4-carboxylic acid, and 2-aminoacetamide, the title compound was obtained in 88% purity by HPLC. MS(ESI+): m/z=423.

Example 408

(2S,4EZ)-N-(2-amino-2-oxoethyl)-1-[(2',3-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 2-aminoacetamide, the title compound was obtained in 85% purity by HPLC. MS(ESI+): m/z=423.

Example 409

(2S,4EZ)-N-(3-amino-3-oxopropyl)-1-[(2',6'-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-aminopropionamide, the title compound was obtained in 87% purity by HPLC. MS(ESI+): m/z=437.

Example 410

(2S,4EZ)-N-(3-amino-3-oxopropyl)-1-[(2',3-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]4-carboxylic acid, and 3-aminopropionamide, the title compound was obtained in 87% purity by HPLC. MS(ESI+): m/z=437.

Example 411

(2S,4EZ)-1-[(2',6'-dimethyl[1,1'-biphenyl]-4-yl)carbonyl]-N-[2-hydroxy-1-(hydroxymethyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 2-amino-1,3-propanediol, the title compound was obtained in 70% purity by HPLC. MS(ESI+): m/z=440.

Example 412

(2S,4EZ)-1-[(2',3'-dimethyl[1,1'-biphenyl]-4-yl)carbonyl]-N-[2-hydroxy-1-(hydroxymethyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 2-amino-1,3-propanediol, the title compound was obtained in 68% purity by HPLC. MS(ESI+): m/z=440.

Example 413

(2,4EZ)-1-[(2'-cyano[1,1'-biphenyl]-4-yl)carbonyl]-N-[(1R,2R)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4 -carboxylic acid, and [(1R,2R)-2-aminocyclohexyl]methanol, the title compound was obtained in 78% purity by HPLC. MS(ESI+): n/z=475.

Example 414

(3EZ,5S)-5-(3,4-dihydro-2(1H)-isoquinolinylcarbonyl)-1-[(2',3-dimethyl[1,1'-biphenyl]-4-yl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 1,2,3,4-tetrahydroisoquinoline, the title compound was obtained in 77% purity by HPLC. MS(ESI+): m/z=482.

Example 415

(2S,4EZ)-N-[(1R)-2-hydroxy-1-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2R)-2-amino-2-phenylethanol, the title compound was obtained in 91% purity by HPLC. MS (ESI+): m/z=472.

Example 416

(2S,4EZ)-1-[(2',6'-dimethyl[1,1'-biphenyl]-4-yl)carbonyl]-N-[2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 4-(2-aminoethyl)phenol, the title compound was obtained in 87% purity by HPLC. MS(ESI+): m/z=486.

Example 417

(2S,4EZ)-1-[(2',3-dimethyl[1,1'-biphenyl]4-yl)carbonyl]-N-[2-(4-hydroxyphenyl)ethyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 4-(2-aminoethyl)phenol, the title compound was obtained in 83% purity by HPLC. MS(ESI+): m/z 486.

Example 418

(2S,4EZ)-1-[(2',6'-dimethyl[1,1'-biphenyl]-4-yl)carbonyl]-N-[2-(3-hydroxyphenyl)ethyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-(2-aminoethyl)phenol, the title compound was obtained in 81% purity by HPLC. MS(ESI+): m/z=486.

Example 419

(2S,4EZ)-1-[(2',3-dimethyl[1,1'-biphenyl]-4-yl)carbonyl]-N-[2-(3-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1-biphenyl]-4carboxylic acid, and 3-(2-aminoethyl)phenol, the title compound was obtained in 89% purity by HPLC. MS(ESI+): m/z=486.

Example 420

(2S,4EZ)-1-[(2',3-dimethyl[1,1'-biphenyl]-4-yl)carbonyl]-N-[(1R,2S)-2-hydroxy-1,2-diphenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1-biphenyl]-4carboxylic acid, and (1S,2R)-2-amino-1,2-diphenylethanol, the title compound was obtained in 73% purity by HPLC. MS(ESI+): m/z=562.

Example 421

(2RS)-2-[({(2S,4EZ)-4-(methoxyimino)-1-[(2'-methyl[1,1'-biphenyl]-4-yl)carbonyl]pyrrolidinyl}carbonyl)amino]-3-phenylpropanoic acid Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and DL-phenylalanine, the title compound was obtained in 62% purity by HPLC. MS(ESI+): m/z=500.

Example 422

(2S,4EZ)-N-[(1R,2S)-2-(aminocarbonyl)cyclohexyl]-1-[(2',6'-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and (1S,2R)-2-aminocyclohexanecarboxamide, the title compound was obtained in 92% purity by HPLC. MS(ESI+): m/z=491.

Example 423

(2S,4EZ)-N-[(1R,2S)-2-(aminocarbonyl)cyclohexyl]-1-[(2',3-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]4-carboxylic acid, and (1S,2R)-2-aminocyclohexanecarboxamide, the title compound was obtained in 91% purity by HPLC. MS(ESI+): m/z=491.

Example 424

4'-{[(2S,4EZ)-2-{[4-(2-hydroxyethyl)-1-piperazinyl]carbonyl}-4-(methoxyimino)pyrrolidinyl]carbonyl}[1,1'-biphenyl]-2-carbonitrile Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and 2-(1-piperazinyl)ethanol, the title compound was obtained in 89% purity by HPLC. MS(ESI+): m/z=476.

Example 425

(3EZ,5S)-1-(3',4'-dichloro[1,1'-biphenyl]-4-yl)carbonyl]-5-{[4-(2-hydroxyethyl)-1-piperazinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and 2-(1-piperazinyl)ethanol, the title compound was obtained in 86% purity by HPLC. MS(ESI+): m/z=520.

Example 426

(3EZ,5S)-1-[(2',6'-dimethyl[1,1'-biphenyl]-4-yl)carbonyl]-5-{4-(2hydroxyethyl)-1-piperazinyl]carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 2-(1-piperazinyl)ethanol, the title compound was obtained in 79% purity by HPLC. MS(ESI+): m/z=479.

Example 427

(3EZ,5S)-1-[(2',3-dimethyl [1,1'-biphenyl]-4-yl)carbonyl]-5-{[4-(2-hydroxyethyl)-1-piperazinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]4-carboxylic acid, and 2-(1-piperazinyl)ethanol, the title compound was obtained in 86% purity by HPLC. MS(ESI+): m/z=479.

Example 428

(3EZ,5S)-1-[(2'-methyl[1,1'-biphenyl]-4-yl)carbonyl]-5-({4-[4-(trifluoromethyl)phenyl]-1-piperazinyl}carbonyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]4-carboxylic acid, and 1-[4-(trifluoromethyl)phenyl]piperazine, the title compound was obtained in 89% purity by HPLC. MS(ESI+): m/z=565.

Example 429

(3EZ,5S)-1-[(2'-methyl[1,1'-biphenyl]-4-yl)carbonyl]-5-({4-[3-(trifluoromethyl)phenyl]-1piperazinyl}carbonyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 1-[3-(trifluoromethyl)phenyl]piperazine, the title compound was obtained in 88% purity by HPLC. MS(ESI+): m/z=565.

Example 430

(2S,4EZ)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]carboxylic acid, and ammonia (0.5M in dioxane), the title compound was obtained in 88% purity by HPLC. MS(ESI+): m/z=352.

Example 431

(2S,4EZ)-4-(methoxyimino)-N-methyl-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and methylamine (2M in methanol), the title compound was obtained in 96% purity by HPLC. MS(ESI+): m/z=366.

Example 432

(2S,4EZ)-4-(methoxyimino)-N,N-dimethyl-1[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and dimethylamine (5.6M in ethanol), the title compound was obtained in 94% purity by HPLC. MS(ESI+): m/z=380.

Example 433

(2S,4EZ)-N-[(3R)-3-hydroxy-3-phenylpropyl]-4-(methoxyimino)-1-[(2'-methyl[1,1'-biphenyl]-4yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R)-3-amino-1-phenyl-1-propanol, the title compound was obtained in 94% purity by HPLC. MS(ESI+): m/z=486.

Example 434

(2S,4EZ)-N-[(3S)-3-hydroxy-3-phenylpropyl]-4-(methoxyimino)-1-(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S)-3-amino-1-phenyl-1-propanol, the title compound was obtained in 91% purity by HPLC. MS(ESI+): m/z=486.

Example 435

(2S,4EZ)-1-([1,1'-biphenyl]4-ylcarbonyl)-N-[(3R)-3-hydroxy-3-phenylpropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]4carbonyl chloride, and (1R)-3-amino-1-phenyl-1-propanol, the title compound was obtained in 94% purity by HPLC. MS(ESI+): m/z=472.

Example 436

(2S,4EZ)-1-([1,1'-biphenyl]-4-ylcarbonyl)-N-(3S)-3-hydroxy-3-phenylpropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S)-3-amino-1-phenyl-1-propanol, the title compound was obtained in 93% purity by HPLC. MS(ESI+): m/z=472.

Example 437

(2S,4EZ)-N-[(2S)-2-hydroxy-2-phenylethyl]-4-(methoxyimino)-1-{[2'-(trifluoromethyl)[1,1'-biphenyl]-yl]carbonyl}-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-(trifluoromethyl)[1,1'-biphenyl]-4-carboxylic acid, and (1S)-2-amino-1-phenylethanol, the title compound was obtained in 87% purity by HPLC. MS(ESI+): m/z=526.

Example 438

(2S,4EZ)-N-[(2S)-2-hydroxy-2-phenylethyl]-4-(methoxyimino)-1-{[2'-chloro[1,1'-biphenyl]-4-yl]carbonyl}-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-chloro[1,1'-biphenyl]-4-carboxylic acid, and (1S)2-amino-1-phenylethanol, the title compound was obtained in 89% purity by HPLC. MS(ESI+): m/z=492.

Example 439

(2S,4EZ)-N-(2-hydroxyphenyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminophenol, the title compound was obtained in 88% purity by HPLC. MS(ESI+): m/z=444.

Example 440

(2S,4EZ)-N-[2-hydroxymethyl)phenyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2-aminophenyl)methanol, the title compound was obtained in 86% purity by HPLC. MS(ESI+): m/z=458.

Example 441

(2S,4EZ)-N-[(2S)-2-hydroxy-2-[phenylethyl]-4-(methoxyimino)-1-[(2-methyl[1,1'-biphenyl]-4-yl)carbonyl]-2pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-methyl[1,1'-biphenyl]-4 -carboxylic acid, and (1S)-2-amino-1-phenylethanol, the title compound was obtained in 95% purity by HPLC. MS(ESI+): m/z=472.

Example 442

(2S,4E and 4Z)-1-([1,1'-biphenyl]-4-ylcarbonyl)-N-[(2S)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S)-2-amino-1-phenylethanol, the title compounds were obtained as a mixture of E/Z-isomers of the oxime functionality. Separation of the isomers by flash chromatography yielded (2S,4E)-1-([1,1'biphenyl]-4-ylcarbonyl)-N-[(2S)-2-hydroxy-2-phenyl]-4-(methoxyimino)-2-pyrrolidinecarboxamide in 98.8% purity and (2S,4Z)-1-([1,1'-biphenyl]-4-ylcarbonyl)-N-[(2S)-2-hydroxy-2phenylethyl]-4-(methoxyimino)-2pyrrolidinecarboxamide in 97.4% purity by HPLC. MS(ESI+): m/z=458.

Example 443

(2S,4EZ)-4-(methoxyimino)-1-[(2'-methyl[1,1'-biphenyl]-4-yl)carbonyl]-N-(2-phenylethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-methyl[1,1'-biphenyl]-4-carboxylic acid, and 2-phenylethanamine, the title compound was obtained in 89% purity by HPLC. MS(ESI+): m/z=456.

Example 444

(2S,4EZ)-N-(2-hydroxyethyl)-4-(methoxyimino)-1-nonanoyl-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, nonanoic acid, and 2-aminoethanol, the title compound was obtained in 93% purity by HPLC. MS(ESI+): m/z=342.

Example 445

Preparation of a Pharmaceutical Formulation

The following formulation examples illustrate representative pharmaceutical compositions of this invention containing pyrrolidine derivatives according to formula I. The present invention, however, is not limited to the following pharmaceutical compositions.

Formulation 1—Tablets

A compound of formula I is admixed as a dry powder with a dry gelatin binder in an approximate 1:2 weight ration. A minor amount of magnesium stearate is added as a lubricant. The mixture is formed into 240–270 mg tablets (80–90 mg of active pyrrolidine derivatives according to formula I per tablet) in a tablet press.

Formulation 2—Capsules

A compound of formula I is admixed as a dry powder with a starch diluent in an approximate 1:1 weight ratio. The mixture is filled into 250 mg capsules (125 mg of active pyrrolidine derivatives according to formula I per capsule).

Formulation 3—Liquid

A compound of formula I (1250 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active pyrrolidine derivatives according to formula I) in a tablet press.

Formulation 5—Injection

The compound of formula I is dissolved in a buffered sterile saline injectable aqueous medium to a concentration of approximately 5 mg/ml.

The compounds of the present invention may be subjected to the following biological assays:

Example 446

Biological Assays a) Production of Recombinant Bax

Human Bax-α lacking 20 amino acids at the COOH-terminus is expressed as a GST fusion protein or a His-tagged protein in *Escherichia coli*, and the protein is purified from the soluble cell fraction. In brief, the GST-Bax fusion protein is applied to a glutathione-Sepharose column, and Bax was released by cleavage with thrombin (0.6 U/mL). Bax is subsequently purified on heparin-Sepharose, followed by fast protein liquid chromatography (FPLC) Mono Q. His-tagged Bax is purified on a Ni-nitriloacetic acid-agarose column followed by FPLC MonoQ:

b) Isolation of Mitochondria

Mitochondria are isolated from mouse liver cells by differential centrifugation. Cells are broken with a dounce homogenizer and the suspension is centrifuged at 2,000 g in an Eppendorf centrifuge at 4° C. This procedure is repeated until almost all the cells are broken. Supernatants from each step are pooled before centrifugation at 13,000 g at 4° C. for 10 min. The pellet is resuspended in 40 mL MB buffer and centrifuged at 2000 g for 2 min. The supernatant is removed and centrifuged at 13 kg for 4 min. The mitochondria are recovered in the 13 k pellet and resuspended in MB buffer at a density of 30 OD600 nm/mL.

c) In Vitro Assay for Cytochrome c Release

Mitochondria (30 µg) from mouse liver are incubated with 200 nM recombinant Bax in the presence of various compounds (5 µM) in 200 mL of KCl buffer for 20 min at 30° C. and are then centrifuged for 4 min at 13,000 g at 4° C. Mitochondrial pellets corresponding to 1.5 µg proteins are separated by SDS-PAGE using 4–20% Tris-Gly gels (NOVEX) and their respective contents of cytochrome c are estimated by Western blotting using polyclonal anti-cytochrome c antibody (dilution 1:2,500). Antigen-antibody complexes are detected using horseradish peroxidase-conjugated goat anti-rabbit IgG and enhance chemiluminescence detection reagents. The cytochrome c bands are scanned and quantified using a Bio-Rad (GS-700 Imaging Densitometer).

d) Effect of Compounds according to formula I onto the Release of Cytochrome c Trig-gered by Bid-Induced Bax Activation (In Vitro Assay)

Concerning the Bid-induced activation of Bax leading to mitochondrial Cytochrome C release, it is referred to the description of Martinou et al. in *The Journal of Cell Biology*, Vol. 144, No. 5, Mar. 8, 1999, pages 891–901. Mitochondria isolated from HeLa cells are incubated for 15 min at 30° C. in 100 µl of KCl buffer in the presence or absence of 10 nM recombinant Bid. The various compounds (10 µM) are pre-incubated for 5 min prior to addition of Bid. Following incubation, mitochondria were centrifuged for 5 min at 13000 g at 4° C. and the supernatant is collected for cytochrome c analysis. Cytochrome c is detected by Western blotting. The cytochrome c bands are scanned and quantified using a Bio-Rad (GS-700 Imaging Densitometer).

The above set out 2 in vitro assays c) and d) involving the determination of mitochondrial cytochrome c release are based on immunochemical methods using the Western blot analysis. Alternatively, said quantitative cytochrome c determinations may be performed by using spectrophotometric means:

I. by recording the difference between reduced and oxidised cytochrome c by dual wavelength double beam spectrophotometry;
II. by measuring the rather intensive γ or Soret peak in the spectrum of cytochrome c ($\epsilon$=100 mM$^{-1}$cm$^{-1}$) is used for rapid and quantitative determination of the release of cytochrome c from isolated mitochondria This technique allows a highly convenient, fast and reliable quantitative determination of the release of cytochrome c.

e) Sympathetic Neuron Culture and Survival Assay (in vivo assay)

Sympathetic neurons from superior cervical ganglia (SCG) of newborn rats (p4) are dis-sociated in dispase, plated at a density of 104 cells/cm² in 48 well MTT plates coated with rat tail collagen, and cultured in Leibowitz medium containing 5% rat serum, 0.75 g/ml NGF 7S (Boehringer Mannheim Corp., Indianapolis, Ind.) and ara- binosine 105M. Cell death is induced at day 4 after plating by exposing the culture to medium containing 10 g/ml of anti NGF antibody (Boehringer Mannheim Corp., Indianapolis, Ind.) and no NGF or arabinosine, in the presence or absence of pyrrolidine derivatives inhibitors according to formula I. 24 hours after cell death induction, determination of cell viability is performed by incubation of the culture for 1 hour, at 37° C. in 0.5 mg/ml of 3-(4,5-dimethyl-thiazol-2-yl)-2,5 diphenyl tetrazolium bromide (MTT). After incubation in MTT cells are re-suspended in DMSO, transferred to a 96 MTT plate and cell viability is evaluated by measuring optical density at 590 nm.

f) Biological Results—Discussion

By using for instance compounds
(4EZ)-N²-(2-hydroxyethyl)-4-(methoxyimino)-N¹-pentyl-1,2-pyrrolidinedicarboxamide or
(2S,4EZ)-2-{[4(1,3-benzodioxol-5-ylmethyl)-1-piperazinyl]carbonyl}-4-(methoxyimino)-N-pentyl-1-pyrrolidinecarboxamide (compound of Example 28)
at a concentration of 10 µM in the above assay d) (Effect of Compounds according to formula I onto the Release of Cytochrome c Triggered by Bid-Induced Bax Activation), an inhibition of about 79% and 59% respectively was determined.

According to a preferred embodiment the tested compounds of formula I display an inhibition of the cytochrome c release of at least 40%, more preferred of at least 60% when tested at a concentration of between 2–50 µM, preferably between 5–20 µM and most preferred at 5–10 µM.

The invention claimed is:

1. Pyrrolidine derivatives according to formula I

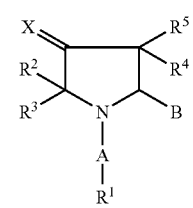

as well as its geometrical isomers, its optically active forms as enantiomers, diastereomers and its racemate forms, as well as pharmaceutically acceptable salts thereof, wherein X is selected from the group consisting of O, S, CR⁶R⁷,;
A is selected from the group consisting of —(C=O)—, —C(=NH)—, —(C=O)—NH—, —(C=S)—NH, and —CH₂—,
B is a group —(C=O)—NR⁸R⁹
R¹ is selected from the group consisting of unsubstituted or substituted C₁–C₆-alkyl, unsubstituted or substituted C₂–C₆-alkenyl, unsubstituted or substituted C₂–C₆-alkynyl, unsubstituted or substituted aryl, unsubstituted or substituted heteroaryl, unsubstituted or substituted saturated or unsaturated 3–8-membered cycloalkyl, acyl, unsubstituted or substituted C₁–C₆-alkyl aryl, and unsubstituted or substituted C₁–C₆-alkyl heteroaryl, wherein said cycloalkyl or aryl or heteroaryl groups may be fused with 1–2 further cycloalkyl or aryl or heteroaryl group;
R², R³, R⁴ and R⁵ are independently selected from each other from the group consisting of hydrogen, halogen, C₁–C₆-alkyl, and C₁–C₆-alkoxy;

$R^6$ and $R^7$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, and unsubstituted or substituted $C_1$–$C_6$-alkyl heteroaryl;

$R^8$, $R^9$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl which may contain 1 to 3 heteroatoms selected of N, O, S, unsubstituted or substituted aryl, and unsubstituted or substituted heteroaryl, or each pair $R^6$, $R^7$ and/or $R^8$, $R^9$ may form together with the N atom to which they are attached a 3–8 membered substituted or unsubstituted, saturated or unsaturated hetero-cyclic ring which may contain 1–2 further heteroatoms selected from N, S and O and which is optionally fused with an aryl, heteroaryl or 3–8 membered saturated or unsaturated cycloalkyl ring;

with the proviso that the following compounds are excluded:

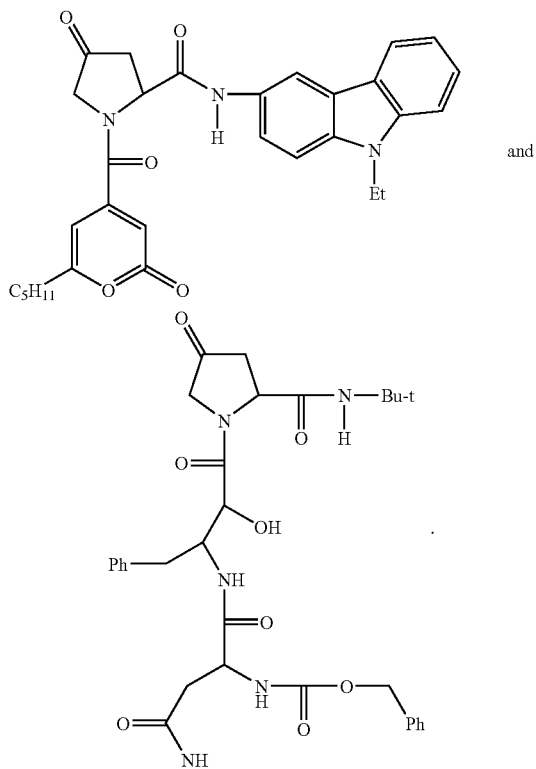

and

2. A pyrrolidine derivative according to claim 1, wherein B is a group —(C═O)—NHR$^9$, in which R$^9$ is selected from the group consisting of unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–6-membered cycloalkyl which optionally contains a N atom, unsubstituted or substituted aryl, unsubstituted or substituted heteroaryl, unsubstituted or substituted $C_1$–$C_2$-alkyl aryl, and unsubstituted or substituted $C_1$–$C_2$-alkyl heteroaryl.

3. A pyrrolidine derivative according to claim 2, wherein R$^9$ is a heteroaryl selected from the group consisting of pyridyl, pyrrolyl, furyl, thienyl, imidazolyl, oxazolyl, isoxazolyl, thiazolyl, isothia-zolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzo-thienyl, 2,1,3-benzothiadiazolyl, 2,1,3-benzoxadiazolyl, benzodioxolyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, acridinyl and benzoquinolyl and whereby said heteroaryl can be fused with a 3–8-membered cycloalkyl containing optionally 1–3 heteroatoms selected from N, O, S.

4. A pyrrolidine derivative according to any of claim 1, 2 or 3, wherein X is CHR$^6$, R$^6$ is selected from the group consisting of halogen, cyano, unsubstituted or substituted $C_3$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, nitro, acyl, alkoxycarbonyl, aminocarbonyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-alkyl aryl, and unsubstituted or substituted $C_1$–$C_6$-alkyl heteroaryl, wherein said cycloalkyl or aryl or heteroaryl groups may be fused with 1–2 further cycloalkyl or aryl or heteroaryl groups.

5. A pyrrolidine derivative according to claim 4, wherein R$^6$ is selected from the group consisting of halogen, cyano, and $C_3$–$C_6$ alkyl or an unsubstituted or substituted phenyl group.

6. A pyrrolidine derivative according to any of claim 1, 2 or 3, wherein X is O.

7. A pyrrolidine derivative according to claim 1, wherein A is —(C═O)—, or —(C═O)—NH—.

8. A pyrrolidine derivative according to claim 7, wherein A is —(C═O)—.

9. A pyrrolidine derivative according to claim 1, wherein R$^1$ is selected from the group consisting of an $C_6$–$C_6$-alkyl, $C_2$–$C_6$-alkenyl, unsubstituted or substituted $C_2$–$C_6$-alkynyl, aryl, heteroaryl, saturated or unsaturated 3–8-mastered cycloalkyl, $C_1$–$C_6$-alkyl aryl, and $C_1$–$C_6$-alkyl heteroaryl.

10. A pyrrolidine derivative according to claim 9, wherein R$^1$ is an $C_1$–$C_6$-alkyl or aryl group.

11. A pyrrolidine derivative according to claim 10, wherein R$^1$ is biphenyl.

12. A pyrrolidine derivative according to claim 1, wherein X is ═CHCl, B is an amido group of the formula —(C═O)NHR$^9$), wherein R$^9$ is as above defined, A is C═O and R$^1$ is a $C_1$–$C_6$-alkyl-aryl, an aryl or a $C_1$–$C_6$-alkyl group.

13. A pyrrolidine derivative according to claim 12, wherein X is either ═CH—Cl, B is an amido group of the formula —(C═O)NHR$^9$), wherein a R$^9$ is a $C_1$–$C_6$-alkyl-aryl, an aryl, a $C_1$–$C_6$-alkyl which is substituted by a primary, secondary or tertiary amine, A is C=O and $R^1$ is a diphenyl methyl or a phenyl group.

14. A pyrrolidine derivative according to claim 1 selected from the group consisting of:

(2S,4EZ)-1-([1,1'-biphenyl]-4-ylcarbonyl)-4-(chloromethylene)-N-(2-hydroxy-2-phenyl-ethyl)-2-pyrrolidinecarboxamide;

(2S,4EZ)-1-([1,1'-biphenyl]-4-ylcarbonyl)-4-(chloromethylene)-N-(2-furylmethyl)-2-pyrrolidinecarboxamide;

(2S,4EZ)-1-[(4-chlorophenoxy)acetyl]-4-{[(3,4-dichlorobenzyl)oxy]imino}-N-[(2RS)-2-hydroxy-2-phenethyl]-2-pyrrolidinecarboxamide;

(2S,4EZ)-4-(cyanomethylene)-N-(2-furylmethyl)-1-[(2-oxo-6-pentyl-2H-pyran-3-yl)carbonyl]-2-pyrrolidinecarboxamide;

(2S,4EZ)-N-(2,1,3-benzothiadiazol-4-yl)-4-(cyanomethylene)-1-(diphenylacetyl)-2-pyrrolidinecarboxamide;

(2S)-2-[1-([1,1'-biphenyl]-4-ylcarbonyl)-4-methylene-2-pyrrolidinyl]-1H-benzimidazole;

(2S,4EZ)-1-([1,1'-biphenyl]-4-ylcarbonyl)-4-(chloromethylene)-N-((2-methoxyethyl)-2-pyrrolidinecarboxamide;

(2S,4EZ)-4-(chloromethylene)-1-(diphenylacetyl)-N-[(2RS)-2-hydroxy-2-phenethyl]-2-pyrrolidinecarboxamide;

(2S)1([1,1'-biphenyl]-4-ylcarbonyl)-N-[(2RS)-2-hydroxy-2-phenethyl]-4-methylene-2-pyrrolidinecarboxamide;

(2S,4EZ)-1-([1,1'-biphenyl]-4-ylcarbonyl)-4-(chloromethylene)-N-(6-quinolinyl)-2-pyrrolidinecarboxamide;

(2S,4EZ)-4-benzylidene-N-[2-(diethylamino)ethyl]-1-(diphenylacetyl)-2-pyrrolidinecarboxamide;

(2S,4EZ)-4-(chloromethylene)-N-(3,4-dimethoxybenzyl)-1-[(2-oxo-6-pentyl-2H-pyran-3-yl)carbonyl]-2-pyrrolidinecarboxamide;

(2S)-N-(2-furylmethyl)-4-methylene-1-[(2-oxo-6-pentyl-2H-pyran-3-yl)carbonyl]-2-pyrrolidinecarboxamide;

(2S)-1-(1,1'-biphenyl]-4-ylcarbonyl)-N-(2-furylmethyl)-4-methylene-2-pyrrolidinecarboxamide;

(2S,4EZ)-4-(cyanomethylene)-N-(3,4-dimethoxybenzyl)-1-[(2-oxo-6-pentyl-2H-pyran-3-yl)carbonyl]-2-pyrrolidinecarboxamide;

(2S)-1-(diphenylacetyl)-N-(1-naphthylmethyl)-4-oxo-2-pyrrolidinecarboxamide;

(2S)-N1-(3,5-dichlorophenyl)-N2-(3,4-dimethoxybenzyl)-4-oxo-1,2-pyrrolidine-dicarboxamide; and (2S)-4-oxo-1-(phenoxyacetyl)-N-[2-(1H-pyrrol-1-yl)phenyl]-2-pyrrolidinecarboxamide.

15. A composition comprising a carrier and a pyrrolidine derivative according to claim 1, with the proviso that the following compounds are excluded from the composition

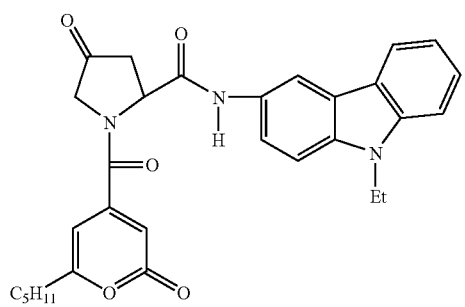

and

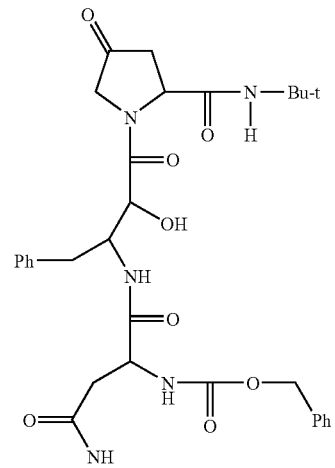

16. A pharmaceutical composition containing at least one pyrrolidine derivative according to claim 1 and a pharmaceutically acceptable carrier, diluent or excipient thereof.

17. A process for the preparation of a pyrrolidine derivative according to claim 1, wherein the following reaction is performed:

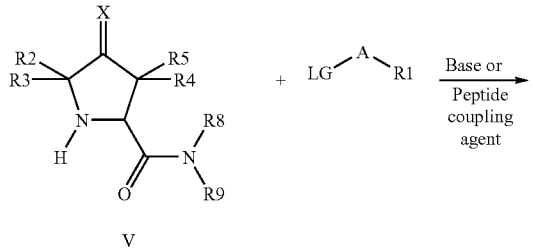

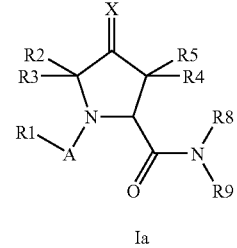

whereby LG is a leaving group and the substituents $R^1$–$R^9$, A and X are as above defined.

18. A method for treating a neuronal disorder, comprising administering to a patient in need thereof a pyrrolidine derivative according to formula IA

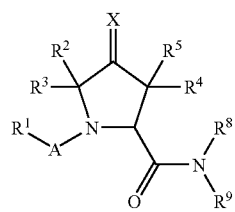

as well as its geometrical isomers, its optically active forms as enantiomers, diastereomers and its racemate forms, as well as pharmaceutically acceptable salts thereof, wherein X is selected from the group consisting of O, S, $CR^6R^7$, $NOR^6$, and $NNR^6R^7$;

A is selected from the group consisting of —(C=O)—, —(C=O)—O—, —C(=NH)—, —(C=O)—NH—, —(C=S)—NH, —SO$_2$—, —SO$_2$NH—, and —CH$_2$—, $R^1$ is selected from the group consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, and unsubstituted or substituted $C_1$–$C_6$-alkyl heteroaryl, wherein said cycloalkyl or aryl or heteroaryl groups may be fused with 1–2 further cycloalkyl or aryl or heteroaryl group;

$R^2$, $R^3$, $R^4$ and $R^5$ are independently selected from each other from the group consisting of hydrogen, halogen, $C_1$–$C_6$-alkyl, and $C_1$–$C_6$-alkoxy;

$R^6$ and $R^7$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, and unsubstituted or substituted $C_1$–$C_6$-alkyl heteroaryl;

$R^8$, $R^9$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl which may contain 1 to 3 heteroatoms selected of N, O, S, unsubstituted or substituted aryl, and unsubstituted or substituted heteroaryl, or each pair $R^6$, $R^7$ and/or $R^8$, $R^9$ can form together with the N atom to which they are attached a 3–8 membered substituted or unsubstituted, saturated or unsaturated hetero-cyclic ring which may contain 1–2 further heteroatoms selected from N, S and O and which is optionally fused with an aryl, heteroaryl or 3–8 membered saturated or unsaturated cycloalkyl ring;

$R^{11}$ is selected from the group consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quarternary ammonium moieties, and unsubstituted or substituted saturated or unsaturated 3–8-membered cycloalkyl.

19. A method according to claim 18, wherein the neuronal disorder is selected from the group consisting of epilepsy, Alzheimer's disease, Huntington's disease, Parkinson's disease, retinal diseases, spinal cord injury, Crohn's disease, head trauma, spinocerebellar ataxias, and dentatorubralpallidoluysian atrophy.

20. A method according to claim 18, wherein said administering step administers the pharmaceutical composition orally to the patient.

21. A method for treating an autoimmune disease, comprising administering to a patient in need thereof a pyrrolidine derivative according to Formula IA

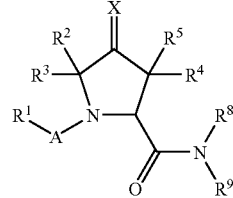

IA as well as its geometrical isomers, its optically active forms as enantiomers, diastereomers and its racemate forms, as well as pharmaceutically acceptable salts thereof, wherein X is selected from the group consisting of O, S, $CR^6R^7$, $NOR^6$, and $NNR^6R^7$;

A is selected from the group consisting of —(C=O)—, —(C=O)—O—, —C(=NH)—, —(C=O)—NH—, —(C=S)—NH, —SO$_2$—, —SO$_2$NH—, and —CH$_2$—, $R^1$ is selected from the group consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, and unsubstituted or substituted $C_1$–$C_6$-alkyl heteroaryl, said cycloalkyl or aryl or heteroaryl groups may be fused with 1–2 further cycloalkyl or aryl or heteroaryl group;

$R^2$, $R^3$, $R^4$ and are $R^5$ independently selected from each other from the group consisting of hydrogen, halogen, $C_1$–$C_6$-alkyl, and $C_1$–$C_6$-alkoxy;

$R^6$ and $R^7$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, and unsubstituted or substituted $C_1$–$C_6$-alkyl heteroaryl;

$R^8$, $R^9$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl which may contain 1 to 3 heteroatoms selected of N, O, S, unsubstituted or substituted aryl, and unsubstituted or substituted heteroaryl, or each pair $R^6$, $R^7$ and/or $R^8$, $R^9$ can form together with the N atom to which they are attached a 3–8 membered substituted or unsubstituted, saturated or unsaturated heterocyclic ring which may contain 1–2 further heteroatoms selected from N, S and O and which is optionally fused with an aryl, heteroaryl or 3–8 membered saturated or unsaturated cycloalkyl ring;

R¹¹ is selected from the group consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quarternary ammonium moieties, and unsubstituted or substituted saturated or unsaturated 3–8-membered cycloalkyl.

22. A method according to claim 21, wherein the autoimmune disease is selected from the group consisting of Multiple Sclerosis, amyotrophic lateral sclerosis, retinitis pigmentosa, inflammatory bowel disease (IBD), rheumatoid arthritis, asthma, septic shock, transplant rejection, and AIDS.

23. A method according to claim 21, wherein said administering step administers the pharmaceutical composition orally to the patient.

24. A method for treating ischemia, comprising administering to a patient in need thereof a pyrrolidine derivative according to formula I

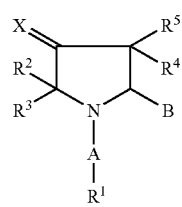

as well as its geometrical isomers, its optically active forms as enantiomers, diastereomers and its racemate forms, as well as pharmaceutically acceptable salts thereof, wherein X is selected from the group consisting of O, S, $CR^6R^7$, $NOR^6$, and $NNR^6R^7$;

A is selected from the group consisting of —(C=O)—, —(C=O)—O—, —C(=NH)—, —(C=O)—NH—, —(C=S)—NH, —SO₂—, —SO₂NH—, and —CH₂—, B is a group —(C=O)—$NR^8R^9$;

R¹ is selected from the group consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, and unsubstituted or substituted $C_1$–$C_6$-alkyl heteroaryl, wherein said cycloalkyl or aryl or heteroaryl groups may be fused with 1–2 further cycloalkyl or aryl or heteroaryl group;

R², R³, R⁴ and R⁵ are independently selected from each other from the group consisting of hydrogen, halogen, $C_1$–$C_6$-alkyl, and $C_1$–$C_6$-alkoxy;

R⁶ and R⁷ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, and unsubstituted or substituted $C_1$–$C_6$-alkyl heteroaryl;

R⁸, R⁹ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, and unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, or each pair R⁶, R⁷ and/or R⁸, R⁹ can form together with the N atom to which they are attached a 3–8 membered substituted or unsubstituted, saturated or unsaturated hetero-cyclic ring which may contain 1–2 further heteroatoms selected from N, S and O and which is optionally fused with an aryl, heteroaryl or 3–8 membered saturated or unsaturated cycloalkyl ring;

R¹¹ is selected from the group consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quarternary ammonium moieties, and unsubstituted or substituted saturated or unsaturated 3–8-membered cycloalkyl.

25. A method according to claim 24, wherein ischemia is caused by an event selected from the group consisting of stroke, myocardial infarction and reperfusion injury, cardiovascular disorders, arteriosclerosis, heart failure, heart transplantation, renal hypoxia, and hepatitis.

26. A method according to claim 24, wherein said administering step administers the pharmaceutical composition orally to the patient.

27. A method for treating an infertility related disorder, comprising administering to a patient in need thereof a pyrrolidine derivative according to formula I

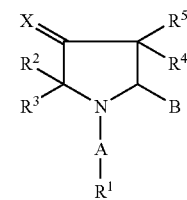

as well as its geometrical isomers, its optically active forms as enantiomers, diastereo-mers and its racemate forms, as well as pharmaceutically acceptable salts thereof, wherein X is selected from the group consisting of O, S, $CR^6R^7$, $NOR^6$, and $NNR^6R^7$;

A is selected from the group consisting of —(C=O)—, —(C=O)—O—, —C(=NH)—, —(C=O)—NH—, —(C=S)—NH, —SO₂—, —SO₂NH—, and —CH₂—, B is a group —(C=O)—$NR^8R^9$;

R¹ is selected from the group consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, and unsubstituted or substituted $C_1$–$C_6$-alkyl heteroaryl, wherein said cycloalkyl or aryl or heteroaryl groups may be fused with 1–2 further cycloalkyl or aryl or heteroaryl group;

$R^2$, $R^3$, $R^4$ and $R^5$ are independently selected from each other from the group consisting of hydrogen, halogen, $C_1$–$C_6$-alkyl, and $C_1$–$C_6$-alkoxy;

$R^6$ and $R^7$ are independently selected from the group consisting of hydrogen, unsubstituted or substituted $C_2$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, and unsubstituted or substituted $C_1$–$C_6$-alkyl heteroaryl;

$R^8$, $R^9$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl which may contain 1 to 3 heteroatoms selected of N, O, S, unsubstituted or substituted aryl, and unsubstituted or substituted heteroaryl, or each pair $R^6$, $R^7$ and/or $R^8$, $R^9$ can form together with the N atom to which they are attached a 3–8 membered substituted or unsubstituted, saturated or unsaturated hetero-cyclic ring which may contain 1–2 further heteroatoms selected from N, S and O and which is optionally fused with an aryl, heteroaryl or 3–8 membered saturated or unsaturated cycloalkyl ring;

$R^{11}$ is selected from the group consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quarternary ammonium moieties, and unsubstituted or substituted saturated or unsaturated 3–8-membered cycloalkyl.

28. A method according to claim 27, wherein the infertility related disorder is selected from the group consisting of premature menopause, ovarian failure, and follicular atresia.

29. A method according to claim 27, wherein said administering step administers the pharmaceutical composition orally to the patient.

* * * * *